United States Patent
Liu et al.

(10) Patent No.: US 11,992,535 B2
(45) Date of Patent: May 28, 2024

(54) COMPOUNDS AND PROBES FOR IMAGING HUNTINGTIN PROTEIN

(71) Applicant: CHDI Foundation, Inc., New York, NY (US)

(72) Inventors: Longbin Liu, Thousand Oaks, CA (US); Matthew Lee, San Diego, CA (US); Celia Dominguez, Los Angeles, CA (US); Peter David Johnson, Oxfordshire (GB); Christopher John Brown, Abingdon (GB); Sarah Hayes, Oxfordshire (GB); Adrian Kotey, Didcot (GB); Matthew Robert Mills, Wantage (GB); Michael Edward Prime, Abingdon (GB)

(73) Assignee: CHDI Foundation, Inc., New York, NY (US)

( * ) Notice: Subject to any disclaimer, the term of this patent is extended or adjusted under 35 U.S.C. 154(b) by 99 days.

(21) Appl. No.: 17/125,905

(22) Filed: Dec. 17, 2020

(65) Prior Publication Data

US 2021/0236663 A1    Aug. 5, 2021

Related U.S. Application Data

(60) Provisional application No. 62/950,020, filed on Dec. 18, 2019.

(51) Int. Cl.
| | | |
|---|---|---|
| *A61K 51/04* | (2006.01) | |
| *C07B 59/00* | (2006.01) | |
| *C07D 401/06* | (2006.01) | |
| *C07D 401/12* | (2006.01) | |
| *C07D 401/14* | (2006.01) | |
| *C07D 413/14* | (2006.01) | |
| *C07D 471/04* | (2006.01) | |
| *C07D 487/04* | (2006.01) | |
| *C07D 491/107* | (2006.01) | |

(52) U.S. Cl.
CPC ...... *A61K 51/0455* (2013.01); *A61K 51/0459* (2013.01); *A61K 51/0468* (2013.01); *C07B 59/00* (2013.01); *C07D 401/06* (2013.01); *C07D 401/12* (2013.01); *C07D 401/14* (2013.01); *C07D 413/14* (2013.01); *C07D 471/04* (2013.01); *C07D 487/04* (2013.01); *C07D 491/107* (2013.01); *C07B 2200/05* (2013.01)

(58) Field of Classification Search
CPC ........... A61K 51/0455; A61K 51/0459; A61K 51/0468; C07B 59/00; C07B 2200/05; C07D 401/06; C07D 401/12; C07D 401/14; C07D 413/14; C07D 471/04; C07D 487/04; C07D 491/107
USPC .......................................................... 424/1.89
See application file for complete search history.

(56) References Cited

U.S. PATENT DOCUMENTS

| | | | | |
|---|---|---|---|---|
| 5,331,573 A | * | 7/1994 | Balaji | G16B 15/00 703/11 |
| 5,700,809 A | | 12/1997 | Leeson et al. | |
| 11,071,793 B2 | * | 7/2021 | Dominguez | C07D 513/04 |
| 2005/0182079 A1 | | 8/2005 | Allen et al. | |
| 2007/0027164 A1 | * | 2/2007 | Stockwell | A61K 31/472 514/254.11 |

FOREIGN PATENT DOCUMENTS

| | | | |
|---|---|---|---|
| WO | WO 2005/105759 A1 | 11/2005 | |
| WO | WO 2013/001088 A1 | 1/2013 | |
| WO | WO 2016/033436 A1 | 3/2016 | |
| WO | WO-2016033445 A1 * | 3/2016 | ........... A61K 51/041 |

OTHER PUBLICATIONS

Tu et al. Expert Opin. Ther. Patents 2015, 25(4), 413-423. (Year: 2015).*
International Search Report and Written Opinion for PCT/US2020/065737, dated Mar. 16, 2021, 18 pages.
Turlington, et al., "Tetrahydronaphthyridine and Dihydronaphthyridinone Ethers As Positive Allosteric Modulators of the Metabotropic Glutamate Receptor 5 (mGlu 5 )", Journal Of Medicinal Chemistry, vol. 57, No. 13, Jul. 10, 2014, pp. 5620-5637, XP055265536.
Olsson et al., "Benzoxazepines Achieve Potent Suppression of IL-17 Release in Human T-Helper 17 ($T_H17$) Cells through an Induced-Fit Binding Mode to the Nuclear Receptor RORγ" , ChemMedChem, vol. 11, No. 2, Nov. 10, 2015, pp. 207-216, XP055782047.
Pagano et al., "Current status of PET imaging in Huntington's disease", European Journal Of Nuclear Medicine, Springer Verlag, Heidelberg, De, vol. 43, No. 6, Feb. 22, 2016 (Feb. 22, 2016), pp. 1171-1182, XP035871102.

* cited by examiner

*Primary Examiner* — Michael G. Hartley
*Assistant Examiner* — Sean R Donohue
(74) *Attorney, Agent, or Firm* — Sheppard Mullin Richter & Hampton LLP

(57) ABSTRACT

Provided herein are certain compounds and imaging agents useful for detecting a condition or disorder associated with protein aggregation, compositions thereof, and methods of their use.

39 Claims, No Drawings

COMPOUNDS AND PROBES FOR IMAGING HUNTINGTIN PROTEIN

CROSS-REFERENCE TO RELATED PATENT APPLICATIONS

This application claims the benefit under 35 U.S.C. § 119(e) of U.S. Provisional Application No. 62/950,020 filed Dec. 18, 2019, which is hereby incorporated by reference in its entirety.

FIELD

Provided herein are compounds and imaging agents useful for detecting a condition or disorder associated with protein aggregation, compositions thereof, and methods of their use.

BACKGROUND

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The introduction of high-resolution molecular imaging technology is considered by many experts as a major breakthrough.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Molecular probes labeled with positron-emitting radionuclides and associated PET imaging assays are under development to target, detect, visualize, and quantify various extracellular and intracellular molecules and processes associated with various diseases.

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It is believed that poly glutamate domain expansion may induce conformational changes in the huntingtin (HTT) protein, which may lead to formation of aggregates. HD has a prevalence of 5-10 cases per 100,000 worldwide, which makes it the most common inherited neurodegenerative disorder.

Consistent with other medical conditions, treatments for HD are ideally initiated at or before early signs of disease. Thus, early indicators of disease are highly desirable.

In view of the central role of the accumulation of aggregated forms of proteins in the pathogenesis of neurodegenerative conditions including HD, there is a need for molecules that bind to such proteins with high sensitivity and specificity and that permit molecular imaging.

SUMMARY

The present disclosure relates to compounds useful for imaging Huntingtin protein. Some embodiments provide for a compound of Formula (I):

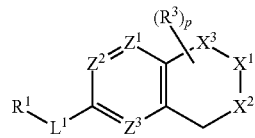

or an isotopically labeled analog, pharmaceutically acceptable salt, solvate, prodrug, stereoisomer, or mixture of stereoisomers thereof, wherein:
$Z^1$ and $Z^2$ are each independently CH, or one of $Z^1$ and $Z^2$ is N and the other is CH;
$Z^3$ is N or CH;
$L^1$ is —O—$C_{1-4}$alkylene, —O—$C_{1-4}$alkylene-O—, or —N($R^4$)C(=O)—;
one of $X^1$ and $X^2$ is N-$L^2$-$R^2$ and the other is $CH_2$;
$X^3$ is $CH_2$ or —O—$CH_2$—;
$L^2$ is —$(CH_2)_n$—, —C(=O)—, —C(=O)NH—, —C(=O)(O)—$(CH_2)_n$, or —S(=O)$_2$;
n is 0, 1, or 2;
$R^1$ is aryl or heteroaryl, each of which is optionally substituted with one or two substituents independently selected from halogen, haloalkyl, hydroxy, alkyl, alkoxy, haloalkoxy, and —N($R^4$)$_2$;
$R^2$ is aryl, alkyl, heteroaryl, heterocycloalkyl, or heterocycloalkenyl, each of which is optionally substituted with one or two substituents independently selected from halogen, haloalkyl, hydroxy, alkyl optionally substituted with alkenyl or alkoxy, alkoxy optionally substituted with alkenyl or alkoxy, haloalkoxy, heteroaryl, and —N($R^4$)$_2$;
p is 0, 1, or 2;
each $R^3$ is independently $C_{1-4}$alkyl, or two $R^3$ on the same carbon form oxo, where $R^3$ may substitute one or more ring carbon atoms of

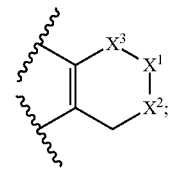

and
each $R^4$ is independently H or $C_{1-4}$alkyl.

Also provided are additional compounds as described herein. In some embodiments, provided is a compound selected from Table 1, or an isotopically labeled analog, pharmaceutically acceptable salt, solvate, prodrug, stereoisomer, or mixture of stereoisomers thereof.

Also provided is a pharmaceutical composition comprising a compound, or an isotopically labeled analog, pharmaceutically acceptable salt, solvate, prodrug, stereoisomer, or mixture of stereoisomers thereof, described herein and a pharmaceutically acceptable carrier.

Also provided is an imaging agent comprising a compound described herein, wherein the compound is labeled with one or more positron-emitting radionuclides. In some embodiments, provided is an imaging agent comprising a compound described herein, wherein the compound is labeled with one or more positron-emitting radionuclides. In some embodiments, provided is an imaging agent comprising a compound described herein, wherein the compound is labeled with one or more positron-emitting radionuclides selected from $^{11}C$, $^{13}N$, $^{15}O$, and $^{18}F$. In some embodiments, the compound contains one or more positron-emitting radionuclides selected from $^{11}C$, $^{13}N$, $^{15}O$, and $^{18}F$.

Also provided is a method of generating diagnostic images, for example positron emission tomography (PET) images, in an individual comprising administering an effective amount of a compound described herein or an imaging agent comprising a compound described herein, and generating an image of a body part or body area of the individual.

Also provided is a method of detecting the presence or absence of a protein susceptible to aggregation, for example huntingtin protein (HTT protein), in a diagnostic image, and detecting the presence or absence of a pathologic process. In some embodiments, the pathologic process may be a neurodegenerative disease selected from Alzheimer's disease, amyotrophic lateral sclerosis, Huntington's disease, Parkinson's disease, Prion disease and spinocerebellar ataxias. In some embodiments, the neurodegenerative disease is Huntington's disease.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash that is not between two letters or symbols is used to indicate a point of attachment for a substituent. For example, —C(O)NH$_2$ is attached through the carbon atom.

By "optional" or "optionally" is meant that the subsequently described event or circumstance may or may not occur, and that the description includes instances where the event or circumstance occurs and instances in which it does not. An "optionally substituted" group is one that may be unsubstituted or may be substituted with the indicated or defined groups. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical and/or inherently unstable.

"Alkyl" encompasses straight chain and branched chain hydrocarbon groups having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkylene" encompasses straight chain and branched chain di-radical hydrocarbon groups having the indicated number of carbon atoms, usually from 1 to 20 carbon atoms, for example 1 to 8 carbon atoms, such as 1 to 6 carbon atoms, or 1 to 4 carbon atoms. For example, a $C_1$ alkylene is a methylene group. Additional examples of $C_1$-$C_4$ alkylene include 1,1-ethylene, 1,2-ethylene, 1,1-propylene, 1,2-propylene, 1,3-propylene, 1,1-butylene, 1,2-butylene, 1,3-butylene, 1,4-butylene, 2-methyl-1,2-propylene, and 2-methyl-1,3-propylene.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic carbon ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a saturated or partially unsaturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged, spirocyclic, and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom)

is not considered a cycloalkyl group, i.e., it is considered an aryl group. "Cycloalkenyl" indicates a partially unsaturated carbocyclic ring that is not an aryl as defined herein.

The term "halo" includes fluoro, chloro, bromo, and iodo, and the term "halogen" includes fluorine, chlorine, bromine, and iodine.

The term "haloalkyl" denotes an alkyl group wherein the alkyl is substituted with one halogen up to a fully substituted ("perhaloalkyl") group. A fully substituted haloalkyl can be represented by the formula $C_nL_{2n+1}$ wherein L is a halogen and "n" is 1 to 6, for example 1, 2, 3 or 4; when more than one halogen is present then they may be the same or different and selected from the group consisting of F, Cl, Br and I, such as F. In some embodiments, a haloalkyl is a $C_{1-4}$ haloalkyl or a $C_{1-6}$ haloalkyl. Examples of $C_{1-4}$ haloalkyl groups include, but are not limited to, fluoromethyl, difluoromethyl, trifluoromethyl, chlorodifluoromethyl, 2,2,2-trifluoroethyl, pentafluoroethyl and the like.

The term "hydroxyalkyl" denotes an alkyl group as defined herein wherein the alkyl is substituted with one, two, three, or four hydroxy groups, with one hydroxy group on each carbon atom. Examples of hydroxyalkyl groups include, but are not limited to, hydroxymethyl, 3-hydroxypropyl, 2-hydroxy-sec-butyl, 3,4-dihydroxybutyl and the like.

The term "haloalkoxy" denotes a haloalkyl which is bonded to the parent structure through an oxygen atom. Examples include, but not limited to, difluoromethoxy, trifluoromethoxy, 2,2,2-trifluoroethoxy, pentafluoroethoxy and the like.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$-0). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, all rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, saturated or partially unsaturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. The term "heterocycloalkyl" includes heterocycloalkenyl groups (i.e. the heterocycloalkyl group having at least one double bond) and may comprise one or more oxo (=O) or N-oxide (—$O^-$) moieties, whether or not oxo is named as a substituent. Heterocycloalkyl groups may be monocyclic (i.e., heteromonocyclic) or polycyclic (e.g., bicyclic (i.e., heterobicyclic), including spirocyclic and bridged ring systems). That is, the definition of heterobicyclic encompasses a heteromonocyclic ring 1,1-disubstituted with a cycloalkyl or heteromonocyclic group, as well as a ring system wherein a heteromonocyclic ring is 1,2- or 1,3-fused to another cycloalkyl or heteromonocyclic ring (where a carbon or nitrogen atom can form the ring junction (where the structure is chemically feasible)), as well as a ring system wherein a heteromonocyclic ring has a $C_1$-$C_2$ alkyl bridge, as well as a ring system wherein a heteromonocyclic ring is 1,2-fused to an aromatic or heteroaromatic ring, provided that the moiety is bound to the parent structure via a non-aromatic carbon or nitrogen atom.

Examples of monocyclic heterocycloalkyl (i.e., heteromonocyclic) groups include oxiranyl, aziridinyl, azetidinyl, oxetanyl, pyrrolidinyl, imidazolidinyl, pyrazolidinyl, piperidinyl, piperazinyl, morpholinyl, piperdin-2-on-1-yl, and thiomorpholinyl.

Examples of a $C_6$ heterobicyclyl group include 3-azabicyclo[3.1.0]hexan-3-yl.

Examples of a $C_8$-$C_{10}$ heterobicyclyl group having an aromatic ring include indolin-1-yl, isoindolin-2-yl, 1,2,3,4-tetrahydroquinolin-2-yl, 3,4-dihydroquinolin-(2H)-yl, and 7,8-dihydro-1,6-naphthyridin-6(5/f)-yl.

Examples of heterobicyclyl ring systems including a spirocycle include: 1-oxa-5-azaspiro[3.3]heptan-5-yl, 1-oxa-6-azaspiro[3.3]heptan-6-yl, 6-oxa-1-azaspiro[3.3]heptan-1-yl, 2-oxa-6-azaspiro[3.3]heptan-6-yl, 1,5-diazaspiro[3.3]heptan-1-yl, 1,6-diazaspiro[3.3]heptan-6-yl, 1,6-diazaspiro[3.3]heptan-1-yl, 2,6-diazaspiro[3.3]heptan-2-yl, 1-oxa-5-azaspiro[3.4]octan-5-yl, 1-oxa-6-azaspiro[3.4]octan-6-yl, 2-oxa-5-azaspiro[3.4]octan-5-yl, 2-oxa-6-azaspiro[3.4]octan-6-yl, 1,5-diazaspiro[3.4]octan-5-yl, 1,6-diazaspiro[3.4]octan-6-yl, 2,5-diazaspiro[3.4]octan-5-yl, 2,6-diazaspiro[3.4]octan-6-yl, 1-oxa-5-azaspiro[3.5]nonan-5-yl, 1-oxa-6-azaspiro[3.5]nonan-6-yl, 1-oxa-7-azaspiro[3.5]nonan-7-yl, 2-oxa-5-azaspiro[3.5]nonan-5-yl, 2-oxa-6-azaspiro[3.5]nonan-6-yl, 2-oxa-7-azaspiro[3.5]nonan-7-yl, 1,5-diazaspiro[3.5]nonan-5-yl, 1,6-diazaspiro[3.5]nonan-6-yl, 1,7-diazaspiro[3.5]nonan-7-yl, 2,5-diazaspiro[3.5]nonan-5-yl, 2,6-diazaspiro[3.5]nonan-6-yl, 2,7-diazaspiro[3.5]nonan-7-yl, 1-oxa-5-azaspiro[3.6]decan-5-yl, 1-oxa-6-azaspiro[3.6]decan-6-yl, 1-oxa-7-azaspiro[3.6]decan-7-yl, 2-oxa-5-azaspiro[3.6]decan-5-yl, 2-oxa-6-azaspiro[3.6]decan-6-yl, 2-oxa-7-azaspiro[3.6]decan-7-yl, 1,5-diazaspiro[3.6]decan-5-yl, 1,6-diazaspiro[3.6]decan-6-yl, 1,7-diazaspiro[3.6]decan-7-yl 2,5-diazaspiro[3.6]decan-5-yl, 2,6-diazaspiro[3.6]decan-6-yl, 2,7-diazaspiro[3.6]decan-7-yl.

Examples of heterobicyclyl ring systems including a $C_1$-$C_4$ bridged-alkylene include 2-azabicyclo[2.2.1]heptan-2-yl, 2-azabicyclo[3.2.1]octan-2-yl, 3-azabicyclo[3.2.1]octan-3-yl, and 6-azabicyclo[3.2.1]octan-6-yl.

When nitrogen is present in a heterocycloalkyl ring, it may, where the nature of the adjacent atoms and groups permits, exist in an oxidized state (i.e., $N^+$-0). Examples include piperidinyl N-oxide and morpholinyl-A-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine 5-oxide and thiomorpholine 5,5-dioxide.

A "solvate" refers to an association or complex of one or more solvent molecules and a compound described herein. Examples of solvents that form solvates include, but are not limited to, water, isopropanol, ethanol, methanol, dimethylsulfoxide, ethyl acetate, acetic acid and ethanolamine.

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives at a hydroxy group), amides (e.g., at an amino group), guanidines (e.g., at an amino group), carbamates (e.g., N,N-dimethylaminocarbonyl at a hydroxy group) derived from functional groups in compounds described herein, and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term "substituted," as used herein, means that any one or more hydrogens on the designated atom or group is replaced with a selected moiety from the indicated group, provided that the designated atom's normal valence is not exceeded. When a substituent is oxo (i.e., =O) then 2 hydrogen atoms on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl groups wherein one or more (such as up to 5, for example, up to 3) hydrogen atoms are replaced by a substituent independently chosen from —$R^a$, —$OR^b$, —$SR^b$, guanidine (—NHC(=NH)$NH_2$), guanidine wherein one or more of the guanidine hydrogens are replaced with a $C_1$-$C_4$ alkyl group, —$NR^bR^c$, halo, cyano, oxo, nitro, —$COR^b$, —$CO_2R^b$, —$CONR^bR^c$, —$OC(O)R^b$, —$OCO_2R^a$, —$OC(O)NR^bR^c$, —$N(R^c)C(O)R^b$, —$N(R^c)CO_2R^a$, —$N(R^c)CONR^bR^c$, —$S(O)R^a$, —$SO_2R^a$, —$SO_2NR^bR^c$, and —$N(R^c)SO_2R^a$, where $R^a$ is chosen from CVO, alkyl, cycloalkyl, aryl, heterocycloalkyl, and heteroaryl;

$R^b$ is chosen from H, CVO, alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group;

and where, in some embodiments, each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

A "stereoisomer" refers to one of a set of compounds made up of the same atoms bonded by the same bonds but having different three-dimensional structures, which are not interchangeable. The term "enantiomer" refers to one of a pair of stereoisomers that are nonsuperimposeable mirror images of one another. It is intended that a compound drawn as a single stereoisomer encompasses a mixture of stereoisomers. In particular, an asymmetric ("chiral") carbon center, with respect to each such center in a compound, may be an enriched mixture or may be a racemic mixture.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) or supercritical fluid chromatograph (SFC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include solid forms. Similarly, the term "salt" is intended to include all tautomeric forms and solid forms of the salt of the compound.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_q-COOH$ where q is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The disclosure also embraces an "isotopically labeled analog" which is identical to a compound described herein, but for the fact that one or more atoms are replaced by an atom having an atomic mass or mass number, or distribution thereof, different from the atomic mass or mass number found in nature. The disclosure also embraces imaging agents comprising the isotopically labeled analog. All isotopically labeled variations of the compounds described herein, whether radioactive or not, are intended to be encompassed within the scope of the present disclosure. Examples of isotopes that can be incorporated into compounds of the disclosure include isotopes of hydrogen, carbon, nitrogen, oxygen, phosphorous, fluorine, and chlorine, such as, but not limited to $^2H$ (deuterium, D), $^3H$ (tritium, T), $^{11}C$, $^{13}C$, $^{14}C$, $^{15}N$, $^{18}F$, $^{31}P$, $^{32}P$, $^{35}S$, $^{36}Cl$, and $^{125}I$, as well as positron-emitting isotopes as described herein. Substitution with heavier isotopes such as deuterium may afford certain therapeutic advantages resulting from greater metabolic stability (e.g., increased in vivo half-life). Isotopically labeled compounds of the present disclosure can generally be prepared by following procedures analogous to those described in the Schemes and Examples, for example, by substituting an isotopically labeled reagent for a non-isotopically labeled reagent. An isotopically labeled compound (including a deuterated or tritiated compound as described herein) generally has an isotopic abundance at the labeled atom that is greater than that found in nature (e.g., found on Earth). In some embodiments, an isotopically labeled analog described herein is a deuterated or tritiated analog. In some embodiments, provided is a deuterated analog of a compound described herein. In some embodiments, provided is a tritiated analog of a compound described herein.

The term "deuterated" as used herein alone or as part of a group, means that one or more hydrogen atom(s) in a compound or imaging agent is replaced by deuterium atom(s) and the term "deuterated analog" as used herein alone or as part of a group, means a compound incorporating such replacement. The term "tritiated" as used herein alone or as part of a group, means that one or more hydrogen atom(s) in a compound or imaging agent is replaced by tritium atom(s) and the term "tritiated analog" as used herein alone or as part of a group, means a compound incorporating such replacement. The deuterated or tritiated analog may be a fully or partially substituted analog. In some embodiments, the deuterated or tritiated analog includes a fully or partially deuterium substituted alkyl, aryl or heteroaryl group.

As used herein the terms "group," "moiety," "radical," "substituent," and "fragment" are synonymous and are intended to indicate portions of molecules attachable to other portions of molecules, e.g., through the indicated attachment point or bond.

The term "active agent" is used to indicate a compound which has biological activity. In some embodiments, an "active agent" is a compound or an isotopically labeled analog, pharmaceutically acceptable salt, solvate, prodrug, stereoisomer, or mixture of stereoisomers thereof, having pharmaceutical utility. For example an active agent may be an anti-neurodegenerative therapeutic.

The term "effective amount" means an amount sufficient to bring about the desired response in the individual or patient. In the context of use of an imaging agent, an effective amount may be an amount needed to produce an image having diagnostic or therapeutic utility. The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease described herein.

The term "huntingtin protein" or "HTT protein" as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "protein aggregate," as used herein refers to an aggregation of protein which may be, for example, an insoluble fibrous amyloid comprising mis-folded HTT protein molecules ("HTT protein aggregate") or mis-folded β-amyloid protein molecules ("β-amyloid aggregate").

The term "imaging agent," as used herein, refers to a compound as described herein labeled with one or more positron-emitting isotopes or radionuclides, or a composition comprising the labeled compound. A positron-emitter labeled compound need only be enriched with a detectable isotope to a degree that permits detection with a technique suitable for the particular application.

The term "PET imaging" (as referred to as positron emission tomography imaging), as used herein, refers to the use of a positron-emitter labeled compound to produce images of internal structures of the human or animal body.

The term "positron-emitting radionuclide," as used herein, refers to a radioactive isotope that exhibits particular type of radioactive decay referred to as β+ decay, in which a proton inside a radionuclide nucleus is converted into a neutron while releasing a positron and an electron neutrino ($v_e$). Some examples of positron-emitting radionuclides include $^{15}O$, $^{13}N$, $^{11}C$, $^{18}F$, $^{76}Br$, and $^{124}I$.

The term "labeled," as used herein, refers to a compound which is associated with one or more positron-emitting radionuclides. For example, a labeled compound described herein may contain one or more positron-emitting radionuclides, wherein an atom in the molecule (including any indicated substituent) is present as a positron-emitting isotope.

The term "tomography," as used herein, refers to a process of imaging by sections. The images may be looked at individually, as a series of two-dimensional slices or together, as a computer-generated three-dimensional representation.

"Treatment" or "treating" means any treatment of a disease state in a patient, including
 a) preventing the disease, that is, causing the clinical symptoms of the disease not to develop;
 b) inhibiting the disease;
 c) slowing or arresting the development of clinical symptoms; and/or
 d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

The term "Curie" (Ci) is a unit of measurement of radioactivity and has its customary meaning to those of skill in the art.

The term "diagnostic imaging," as used herein, refers to the use of electromagnetic radiation to produce images of internal structures of the human or animal body for the purpose of diagnosis.

A compound described herein refers to a compound, or an isotopically labeled analog, pharmaceutically acceptable salt, solvate, prodrug, stereoisomer, or mixture of stereoisomers thereof, of any of Formula (I), Formula (IIa), Formula (IIb), Formula (IIIa), Formula (IIIb), or Formula (IIIc), or a compound of the Examples, or a compound of Table 1 or a labeled isomer of such compound as defined herein, or an imaging agent comprising such compound or labeled compound.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I are specifically embraced herein just as if each and every combination was individually and explicitly recited, to the extent that such combinations result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

LIST OF ABBREVIATIONS AND ACRONYMS

| | |
|---|---|
| δ | chemical shift |
| addn. | addition |
| approx. | approximately |
| aq. | aqueous |
| Ar | aryl |
| atm | atmosphere |
| BINAP | (2,2'-Bis(diphenylphosphino)-1,1'-binaphthyl) |
| Boc | tert-butyloxycarbonyl |
| Bn | benzyl |
| br | broad |
| BrettPhos | 2-(Dicyclohexylphosphino)-3,6-dimethoxy-2',4',6'-triisopropyl-1,1'-biphenyl |
| BuLi | Butyl lithium |
| calcd | calculated |
| Cbz | Benzyloxycarbonyl |
| CMBP | Cyanomethyltributylphosphorane |
| conc. | Concentrated |
| CyJohnPhos | (2-Biphenyl)dicyclohexylphosphine, 2-(Dicyclohexylphosphino)biphenyl |
| dba | Dibenzylideneacetone |
| DCM | Dichloromethane |
| DIPEA | Diisopropylethylamine |
| DMF | Dimethylformamide |
| DMSO | Dimethylsulfoxide |
| dppf | Bisdiphenylphosphonyl ferrocene |
| EDCI | 1-(3-dimethylaminopropyl)-3-ethylcarbodiimide hydrochloride |
| ELS | Evaporative light scattering |
| eq | equivalent |
| ES+ | Electrospray Positive Ionization |
| EtOAc | ethyl acetate |
| EtOH | Ethanol |
| FCC | Flash column chromatography |
| h | Hour(s) |
| HATU | N-[(Dimethylamino)-1H-1,2,3-triazolo-[4,5-b]pyridin-1-ylmethylene]-N-ethylmethanaminium hexafluorophosphate N-oxide |
| HCl | Hydrochloric acid |
| HOBt | 1-Hydroxybenzotriazole |
| HPLC | High Performance Liquid Chromatography |
| IPA | Isopropyl alcohol |
| J | Coupling constant |
| $K_2CO_3$ | Potassium carbonate |
| KOtBu | Potassium tert-butoxide |
| LCMS | Liquid Chromatography Mass Spectrometry |
| LIHMDS | Lithium hexamethyldisilazide |
| M | Molarity |
| MeCN | Acetonitrile |
| MeOH | Methanol |
| min | Minute(s) |
| MS | Mass Spectrometry |
| m/z | Mass to charge ratio |
| $N_2$ | nitrogen |
| NMR | Nuclear Magnetic Resonance |
| Pd/C | Palladium on carbon |
| Pd2(dba)$_3$ | Tris(dibenzylideneacetone)dipalladium(0) |

-continued

| | |
|---|---|
| PdCl$_2$(tBu$_2$Pferrocene)$_2$ | [1,1'-Bis(di-tert-butylphosphino)ferrocene]dichloropalladium(II) |
| Ph | phenyl |
| PPh3 | Triphenyl phosphine |
| prep | Preparative |
| quant. | quantitative |
| rt | Room temperature |
| Tr | Retention time |
| RuPhos | 2-Dicyclohexylphosphino-2',6'-diisopropoxybiphenyl |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |
| sat. | saturated |
| SCX | Propylsulfonic acid (non-endcapped) functionalized silica |
| SFC | Supercritical Fluid Chromatography |
| TBAF | Tetrabutylammonium fluoride |
| TFA | Trifluoroacetic acid |
| THF | Tetrahydrofuran |
| Ts | p-toluenesulfonyl |
| UV | ultraviolet |

Compounds

The present disclosure relates to compounds useful for imaging Huntingtin protein. Some embodiments provide for a compound of Formula (I):

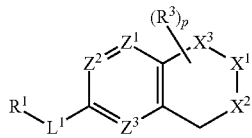
(I)

or an isotopically labeled analog, pharmaceutically acceptable salt, solvate, prodrug, stereoisomer, or mixture of stereoisomers thereof,
wherein:
    $Z^1$ and $Z^2$ are each independently CH, or one of $Z^1$ and $Z^2$ is N and the other is CH;
    $Z^3$ is N or CH;
    $L^1$ is —O—$C_{1-4}$alkylene, —O—$C_{1-4}$alkylene-O—, or —N($R^4$)C(=O)—;
    one of $X^1$ and $X^2$ is N-$L^2$-$R^2$ and the other is CH$_2$;
    $X^3$ is CH$_2$ or —O—CH$_2$—;
    $L^2$ is —(CH$_2$)$_n$—, —C(=O)—, —C(=O)NH—, —C(=O)(O)—(CH$_2$)$_n$, or —S(=O)$_2$;
    n is 0, 1, or 2;
    $R^1$ is aryl or heteroaryl, each of which is optionally substituted with one or two substituents independently selected from halogen, haloalkyl, hydroxy, alkyl, alkoxy, haloalkoxy, and —N($R^4$)$_2$;
    $R^2$ is aryl, alkyl, heteroaryl, heterocycloalkyl, or heterocycloalkenyl, each of which is optionally substituted with one or two substituents independently selected from halogen, haloalkyl, hydroxy, alkyl optionally substituted with alkenyl or alkoxy, alkoxy optionally substituted with alkenyl or alkoxy, haloalkoxy, heteroaryl, and —N($R^4$)$_2$;
    p is 0, 1, or 2;
    each $R^3$ is independently $C_{1-4}$alkyl, or two $R^3$ on the same carbon form oxo, where $R^3$ may substitute one or more ring carbon atoms of

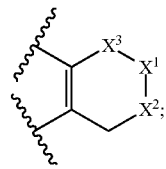

and
    each $R^4$ is independently H or $C_{1-4}$alkyl.
In some embodiments, the compound of Formula (I) is a compound of Formula (IIa):

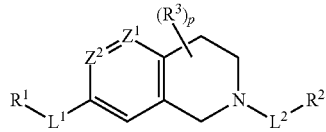
(IIa)

or an isotopically labeled analog, pharmaceutically acceptable salt, solvate, prodrug, stereoisomer, or mixture of stereoisomers thereof.
In some embodiments, the compound of Formula (I) is a compound of Formula (IIb):

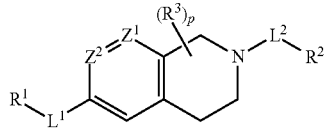
(IIb)

or an isotopically labeled analog, pharmaceutically acceptable salt, solvate, prodrug, stereoisomer, or mixture of stereoisomers thereof.
In some embodiments, the compound of Formula (I) is a compound of Formula (IIIa):

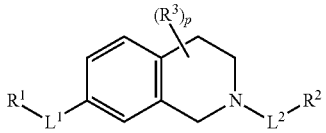
(IIIa)

or an isotopically labeled analog, pharmaceutically acceptable salt, solvate, prodrug, stereoisomer, or mixture of stereoisomers thereof.
In some embodiments, the compound of Formula (I) is a compound of Formula (IIIb):

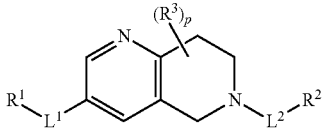
(IIIb)

or an isotopically labeled analog, pharmaceutically acceptable salt, solvate, prodrug, stereoisomer, or mixture of stereoisomers thereof.

In some embodiments, the compound of Formula (I) is a compound of Formula (IIIc):

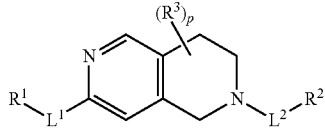

(IIIc)

or an isotopically labeled analog, pharmaceutically acceptable salt, solvate, prodrug, stereoisomer, or mixture of stereoisomers thereof.

In some embodiments, $L^1$ is —O—$C_{1-4}$alkylene and $R^1$ is heteroaryl optionally substituted with one or two substituents independently selected from hydroxy, alkyl, alkoxy, haloalkoxy, and —$N(R^4)_2$.

In some embodiments, $L^1$ is —O—$C_{1-4}$alkylene, and $R^1$ is pyridinyl optionally substituted with one or two substituents independently selected from hydroxy, alkyl, alkoxy, and haloalkoxy.

In some embodiments, $L^1$ is —O—$C_{1-4}$alkylene and $R^1$ is pyridinyl optionally substituted with methoxy.

In some embodiments, $R^1$ is

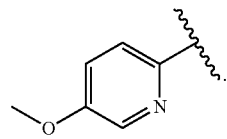 [SMILES: *c1ccc(OC)cn1]

In some embodiments, -$L^1$-$R^1$ is

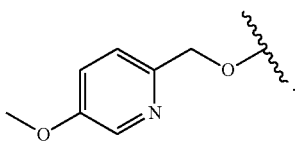 [SMILES: *OCc1ccc(OC)cn1]

In some embodiments, $L^2$ is —C(=O)—.
In some embodiments, $L^2$ is —$(CH_2)_n$— and n is 0.
In some embodiments, $Z^1$ and $Z^2$ are each independently CH.
In some embodiments, one of $Z^1$ and $Z^2$ is N and the other is CH.
In some embodiments, $Z^1$ is N and $Z^2$ is CH.
In some embodiments, $Z^2$ is N and $Z^1$ is CH.
In some embodiments, $R^2$ is heteroaryl.
In some embodiments, $R^2$ is a 6-membered heteroaryl ring containing one or two N.
In some embodiments, $R^2$ is selected from

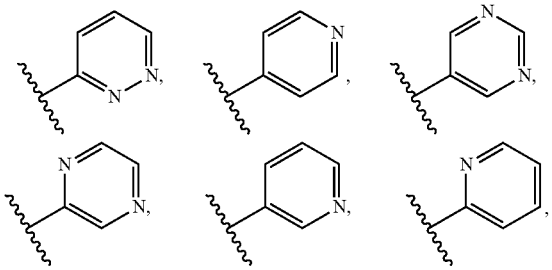

-continued

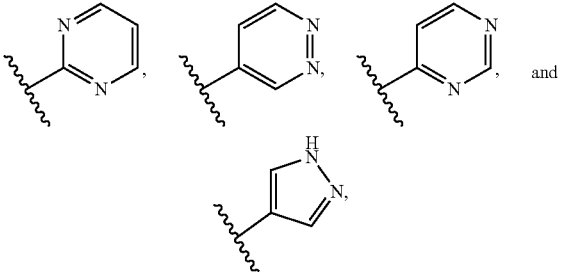

each of which is optionally substituted with one or two substituents independently selected from hydroxy, alkyl optionally substituted with alkoxy, haloalkyl, alkoxy optionally substituted with alkenyl or alkoxy, haloalkoxy, —$N(R^4)_2$, and heteroaryl.

In some embodiments, $R^2$ is heterocycloalkyl or heterocycloalkenyl.

In some embodiments, $R^2$ is selected from

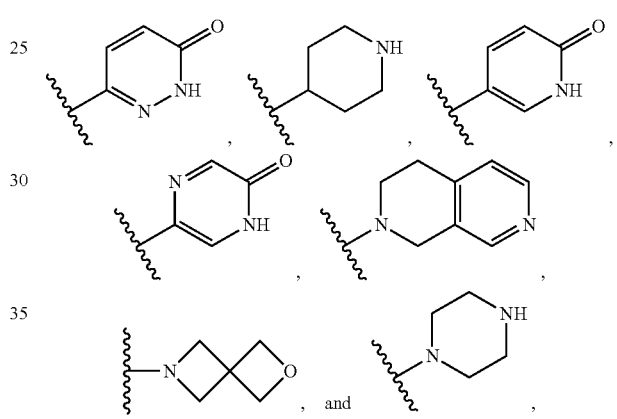

, and each of which is optionally substituted with one or two substituents independently selected from hydroxy, alkyl optionally substituted with alkoxy, haloalkyl, alkoxy optionally substituted with alkenyl or alkoxy, haloalkoxy, —$N(R^4)_2$, and heteroaryl.

In some embodiments, $Z^3$ is CH.
In some embodiments, $X^3$ is $CH_2$.
In some embodiments, n is 0. In some embodiments, n is 1. In some embodiments, n is 2.
In some embodiments, p is 0. In some embodiments, p is 1. In some embodiments, p is 2.
In some embodiments of Formula (I), one of $X^1$ and $X^2$ is N-$L^2$-$R^2$ and the other is $CH_2$, $CHR^3$, or $C(R^3)_2$. In some embodiments of Formula (I), one of $X^1$ and $X^2$ is N-$L^2$-$R^2$ and the other is $CH_2$. In some embodiments of Formula (I), one of $X^1$ and $X^2$ is N-$L^2$-$R^2$ and the other is $CHR^3$. In some embodiments of Formula (I), one of $X^1$ and $X^2$ is N-$L^2$-$R^2$ and the other is $C(R^3)_2$. In some embodiments of Formula (I), $X^3$ is $CH_2$, $C(R^3)_2$ or $CHR^3$.

In some embodiments, provided is a compound selected from those in Table 1, or an isotopically labeled analog, pharmaceutically acceptable salt, solvate, prodrug, stereoisomer, or mixture of stereoisomers thereof.

In some embodiments, provided is a compound of any one of the preceding claims, wherein the compound is labeled with one or more positron-emitting radionuclides.

In some embodiments, provided is an imaging agent comprising a compound described herein, or an isotopically labeled analog, pharmaceutically acceptable salt, solvate, prodrug, stereoisomer, or mixture of stereoisomers thereof. Also provided is an imaging agent comprising a compound described herein, wherein the compound is labeled with one or more positron-emitting radionuclides.

In some embodiments, provided is a compound described herein containing one or more positron-emitting radionuclides selected from $^{11}$C, $^{13}$N, $^{15}$O, and $^{18}$F.

In some embodiments, provided is a method of generating diagnostic images in an individual comprising administering an effective amount of a compound or an imaging agent described herein to an individual, and generating an image of a body part or body area of the individual.

In some embodiments, generating an image of a body part or body area of the individual comprises generating an image to detect the presence or absence of huntingtin protein (HTT protein) in the image; and detecting the presence or absence of a pathologic process.

In some embodiments, the HTT protein is found in basal ganglia.

In some embodiments, the pathologic process is a neurodegenerative disease.

In some embodiments, the neurodegenerative disease is selected from Alzheimer's disease, amyotrophic lateral sclerosis, Huntington's disease, Parkinson's disease, Prion disease and spinocerebellar ataxias.

In some embodiments, the neurodegenerative disease is Huntington's disease (HD).

In some embodiments, the effective amount of the compound or imaging agent described herein comprises from about 0.1 to about 20 mCi.

In some embodiments, the effective amount of the compound or imaging agent described herein comprises about 10 mCi.

In some embodiments, generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof.

In some embodiments, generating an image comprises PET imaging.

In some embodiments, the HTT protein is present as monomers, oligomers, or aggregates, or a combination thereof. In some embodiments, the HTT protein is present as aggregates thereof.

In some embodiments, the HTT protein is mutant.

In some embodiments, the body part or body area is selected from head, spinal cord, limb, thorax, or abdomen.

In some embodiments, the body part or body area is brain.

In some embodiments, a compound described herein may be labeled with one or more positron-emitting radionuclides.

In some embodiments, a compound described herein includes one or more constituent atoms that have been replaced with a positron-emitting radionuclide, wherein each positron-emitting radionuclide is an isotope of the atom that is replaced. Suitable positron-emitting radionuclides that may be incorporated in the compounds of described herein, but are not limited to, $^{11}$C, $^{13}$N, $^{15}$O, $^{18}$F, $^{52}$Fe, $^{62}$Cu, $^{64}$Cu, $^{68}$Ga, $^{74}$As, $^{82}$Rb, $^{89}$Zr, $^{122}$I, and $^{124}$I. In some embodiments, the one or more positron-emitting radionuclides are selected from: $^{11}$C, $^{13}$N, $^{15}$O, $^{18}$F, $^{76}$Br, and $^{124}$I. In some embodiments the one or more positron-emitting radionuclides are selected from $^{11}$C, $^{13}$N, $^{15}$O, and $^{18}$F.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

In some embodiments, provided is a compound selected from those in described in the Examples section provided herein. In some embodiments, provided is a compound selected from Table 1, or an isotopically labeled analog, pharmaceutically acceptable salt, solvate, prodrug, stereoisomer, or mixture of stereoisomers thereof. In some embodiments, provided is a compound of Table 1 labeled with one or more positron-emitting radionuclides.

TABLE 1

| Example | Structure |
|---------|-----------|
| 1 | 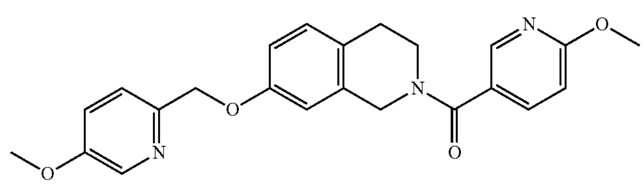 |
| 1.1 | 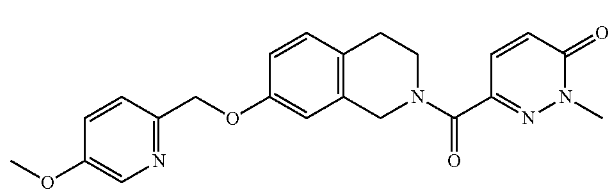 |

TABLE 1-continued
| Example | Structure |
|---|---|
| 1.2 | 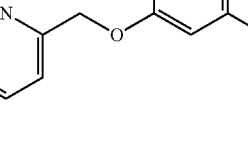 |
| 1.3 | 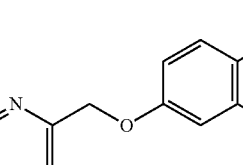 |
| 1.4 | 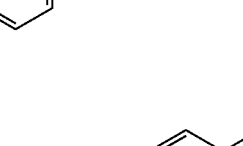 |
| 1.5 | 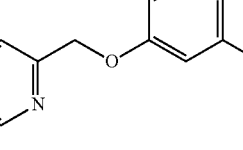 |
| 1.6 | 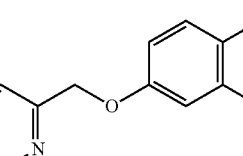 |
| 1.7 | 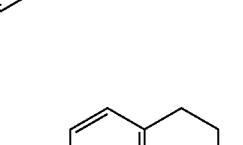 |
| 1.8 | 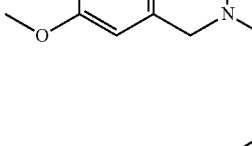 |

TABLE 1-continued

| Example | Structure |
|---|---|
| 1.9 | 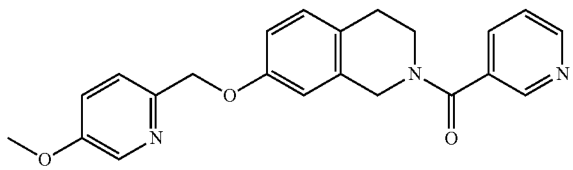 [SMILES: COc1ccc(COc2ccc3c(c2)CN(C(=O)c2cccnc2)CC3)nc1] |
| 1.10 | 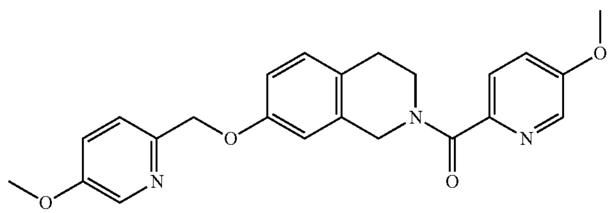 |
| 1.11 | 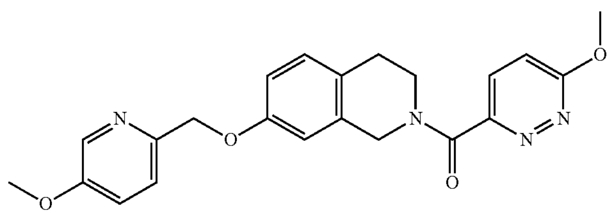 |
| 1.12 | 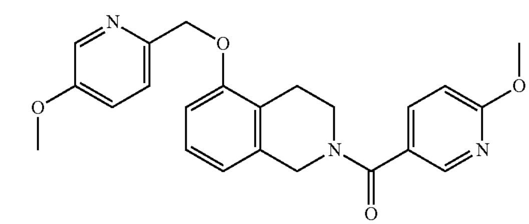 [SMILES: COc1ccc(COc2cccc3c2CCN(C(=O)c2ccc(OC)nc2)C3)nc1] |
| 1.13 | 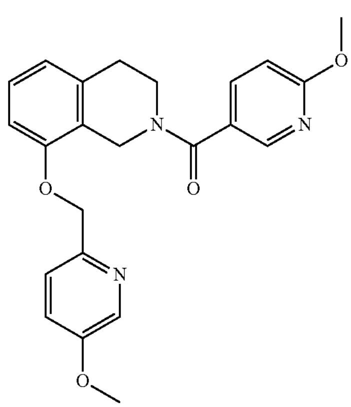 [SMILES: COc1ccc(COc2cccc3c2CN(C(=O)c2ccc(OC)nc2)CC3)nc1] |
| 1.14 | 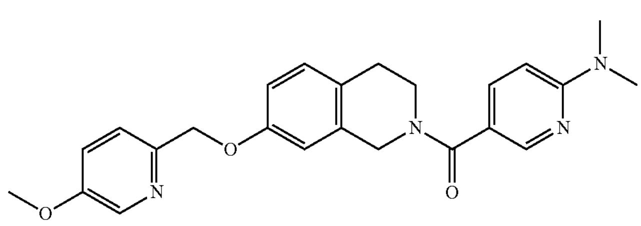 |

TABLE 1-continued

| Example | Structure |
|---|---|
| 1.15 | 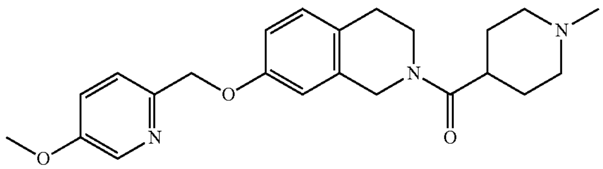 |
| 1.16 | 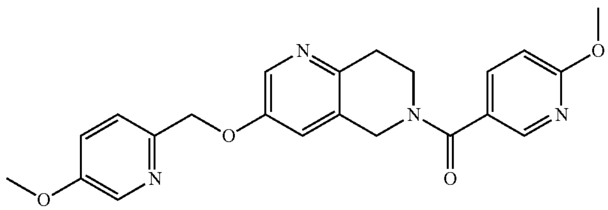 |
| 1.17 | 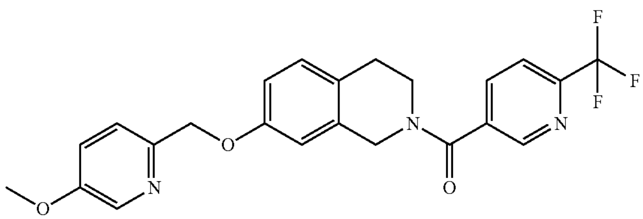 [SMILES: COc1ccc(COc2ccc3c(c2)CN(C(=O)c2ccc(C(F)(F)F)nc2)CC3)nc1] |
| 1.18 | 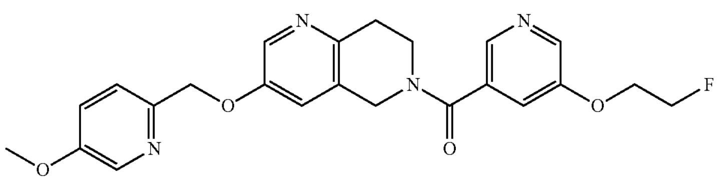 [SMILES: COc1ccc(COc2cnc3c(c2)CN(C(=O)c2cncc(OCCF)c2)CC3)nc1] |
| 1.19 | 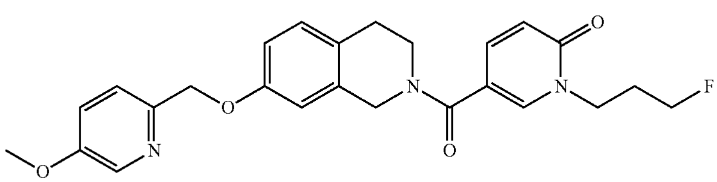 [SMILES: COc1ccc(COc2ccc3c(c2)CN(C(=O)c2ccc(=O)n(CCCF)c2)CC3)nc1] |
| 1.20 | 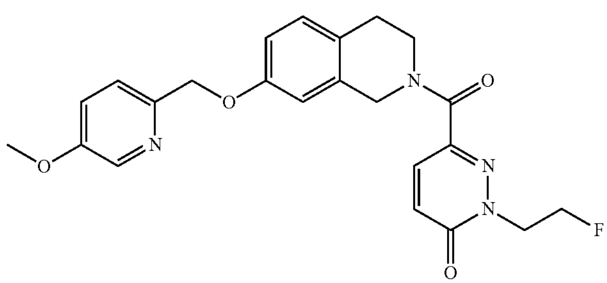 [SMILES: COc1ccc(COc2ccc3c(c2)CN(C(=O)c2ccc(=O)n(CCF)n2)CC3)nc1] |
| 1.21 | 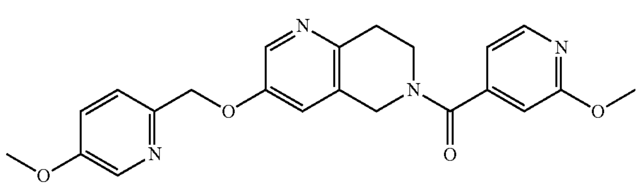 |

TABLE 1-continued

| Example | Structure |
|---|---|
| 1.22 | 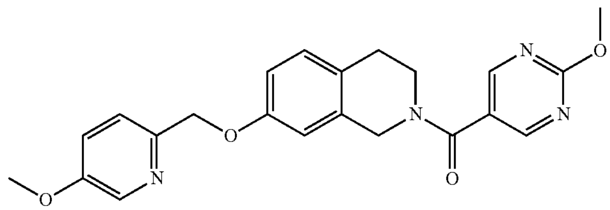 |
| 1.23 | 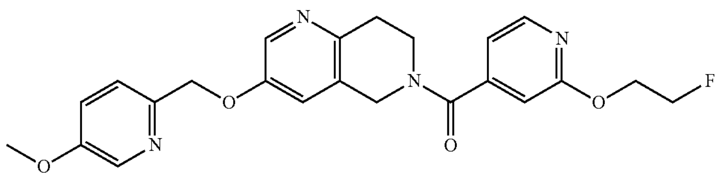 [SMILES: COc1ccc(COc2cnc3c(c2)CN(C(=O)c2ccnc(OCCF)c2)CC3)nc1] |
| 1.24 | 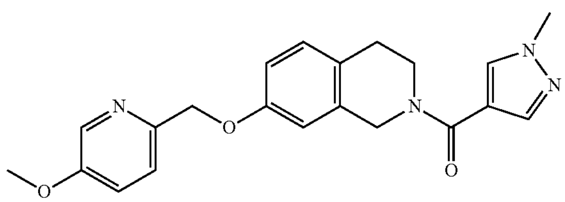 [SMILES: COc1ccc(COc2ccc3c(c2)CN(C(=O)c2cnn(C)c2)CC3)nc1] |
| 1.25 | 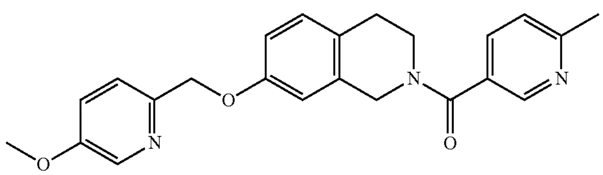 |
| 1.26 | 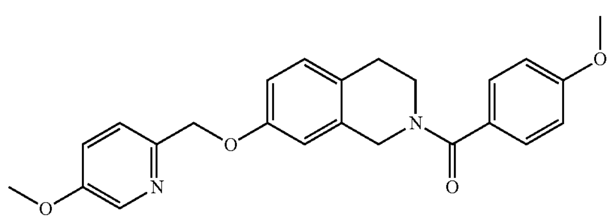 |
| 1.27 | 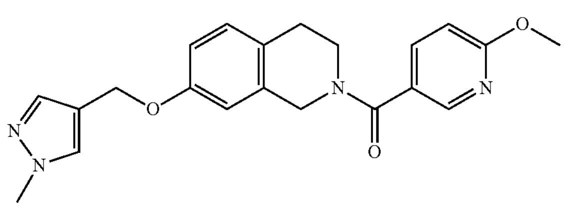 [SMILES: COc1ccc(C(=O)N2CCc3ccc(OCc4cnn(C)c4)cc3C2)cn1] |
| 1.28 | 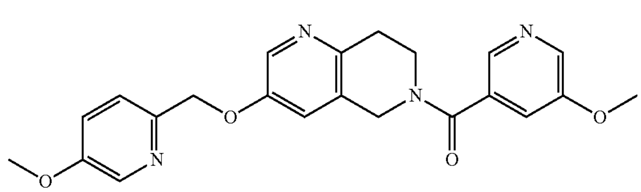 |

TABLE 1-continued

| Example | Structure |
|---|---|
| 1.29 | 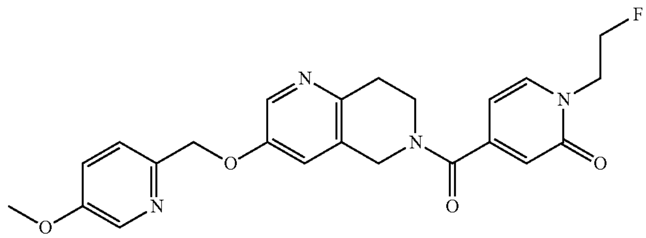 [SMILES: COc1ccc(COc2cnc3c(c2)CN(C(=O)c2ccn(CCF)c(=O)c2)CC3)nc1] |
| 1.30 | 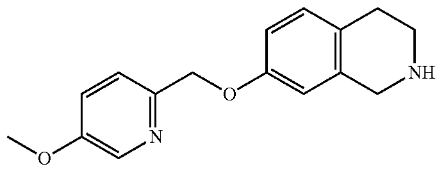 [SMILES: COc1ccc(COc2ccc3c(c2)CNCC3)nc1] |
| 2 | 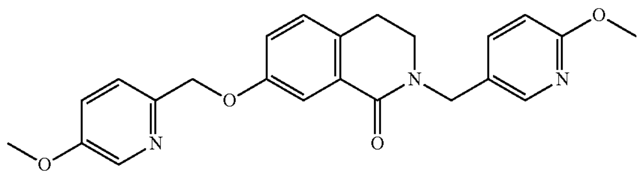 |
| 3 | 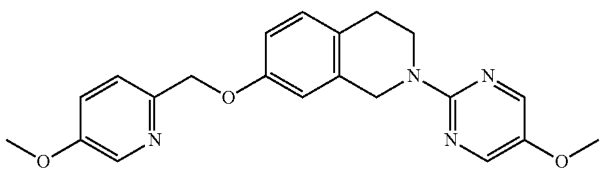 |
| 4 | 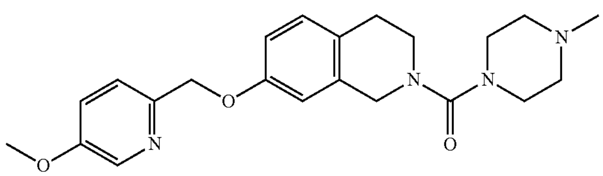 |
| 4.1 | 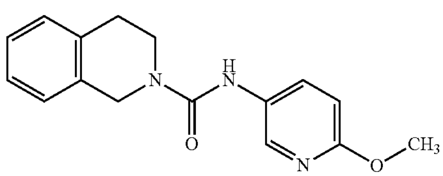 [SMILES: COc1ccc(NC(=O)N2CCc3ccccc3C2)cn1] |
| 4.2 | 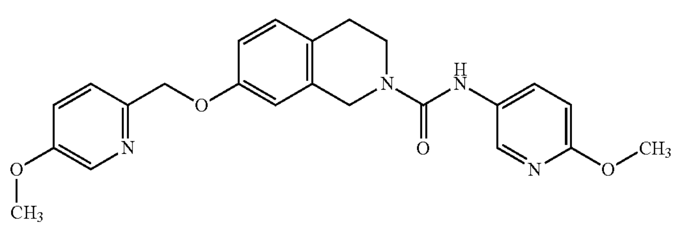 [SMILES: COc1ccc(COc2ccc3c(c2)CN(C(=O)Nc2ccc(OC)nc2)CC3)nc1] |
| 4.3 | 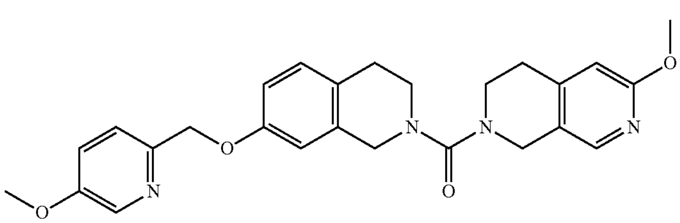 |

TABLE 1-continued
| Example | Structure |
|---|---|
| 4.4 | 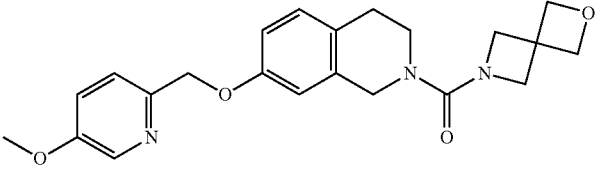 [SMILES: COc1ccc(COc2ccc3c(c2)CN(C(=O)N2CC4(COC4)C2)CC3)nc1] |
| 5 | 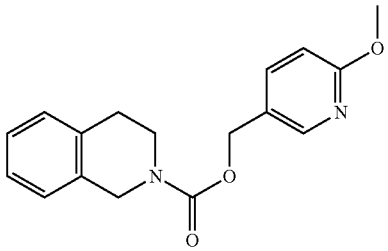 [SMILES: COc1ccc(COC(=O)N2CCc3ccccc3C2)cn1] |
| 5.1 | 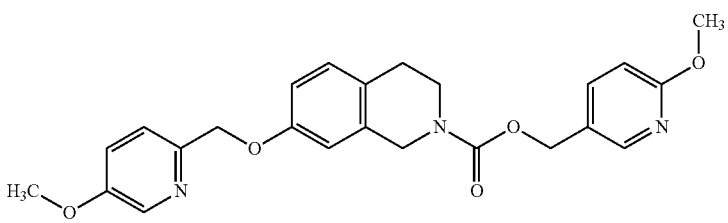 |
| 6 | 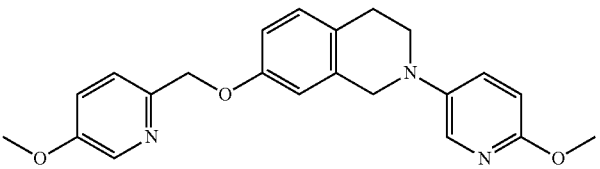 |
| 6.1 | 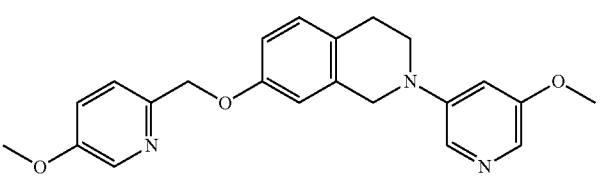 |
| 6.2 | 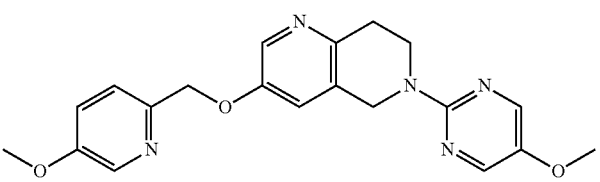 |
| 6.3 | 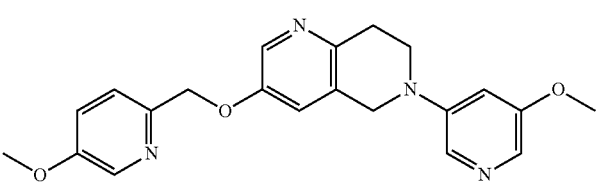 |
| 7 | 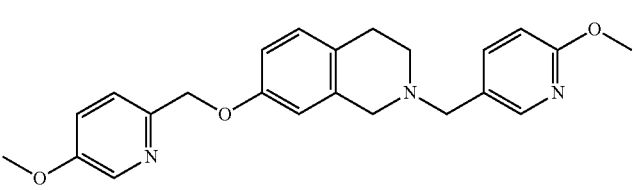 |

TABLE 1-continued

| Example | Structure |
|---|---|
| 8 | 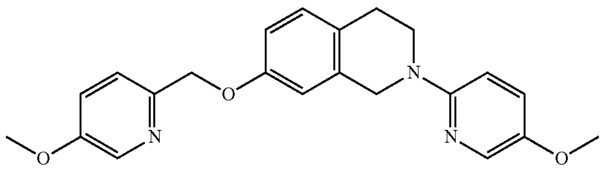 |
| 8.1 | 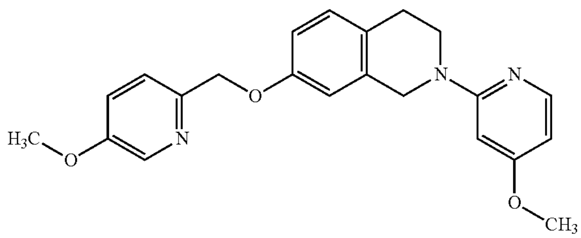 |
| 8.2 | 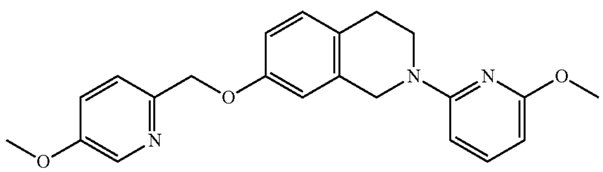 |
| 9 | 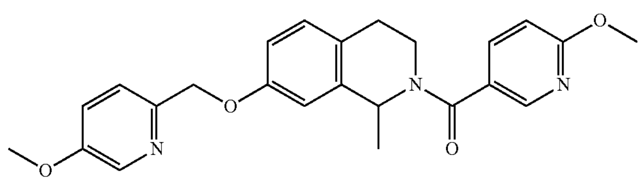 |
| 10 | 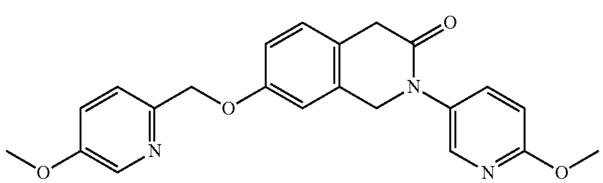 |
| 11 | 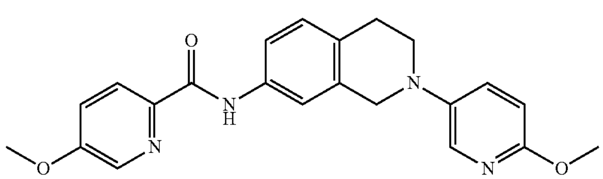 |
| 12 | 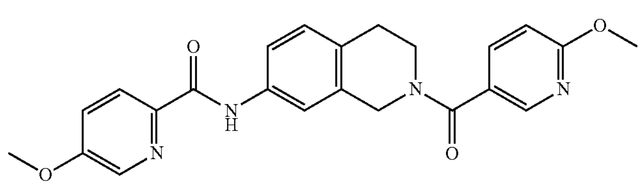 |
| 13 | 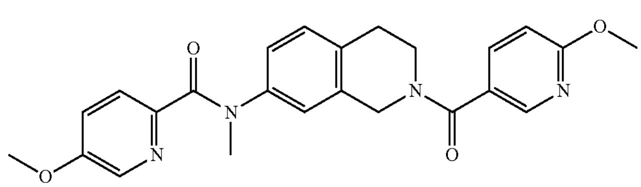 |

TABLE 1-continued

| Example | Structure |
|---------|-----------|
| 15 | 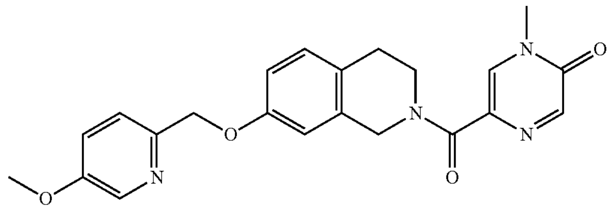 [SMILES: COc1ccc(COc2ccc3c(c2)CN(C(=O)c2cn(C)c(=O)cn2)CC3)nc1] |
| 16 | 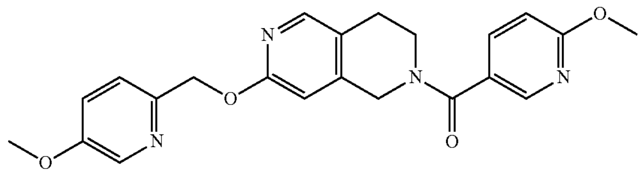 |
| 17 | 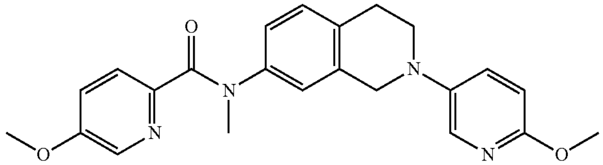 |
| 18 | 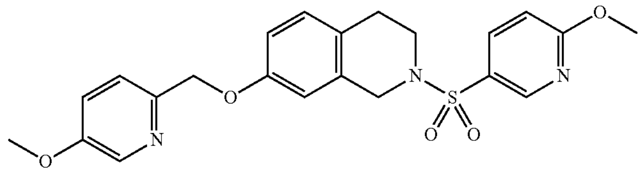 |
| 19 | 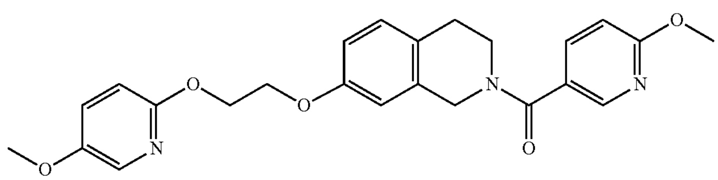 |
| 20 | 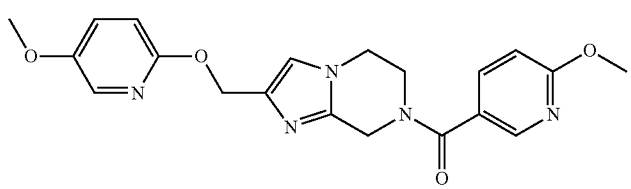 |
| 24 | 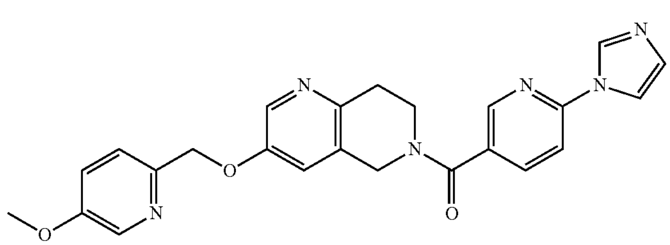 [SMILES: COc1ccc(COc2cnc3c(c2)CN(C(=O)c2ccc(-n4ccnc4)nc2)CC3)nc1] |
| 24.1 | 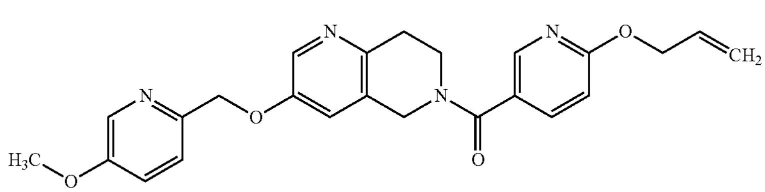 [SMILES: C=CCOc1ccc(C(=O)N2CCc3ncc(OCc4ccc(OC)cn4)cc3C2)cn1] |

TABLE 1-continued

| Example | Structure |
|---|---|
| 24.2 | 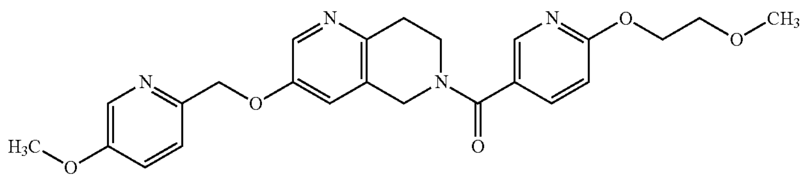 |
| 24.3 | 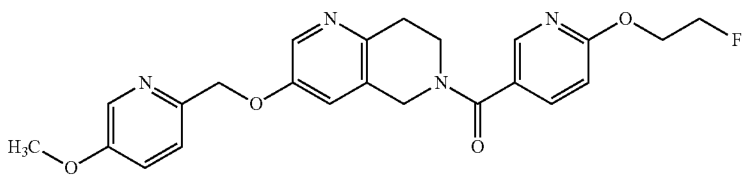 [SMILES: COc1ccc(COc2cnc3c(c2)CN(C(=O)c2ccc(OCCF)nc2)CC3)nc1] |
| 24.4 | 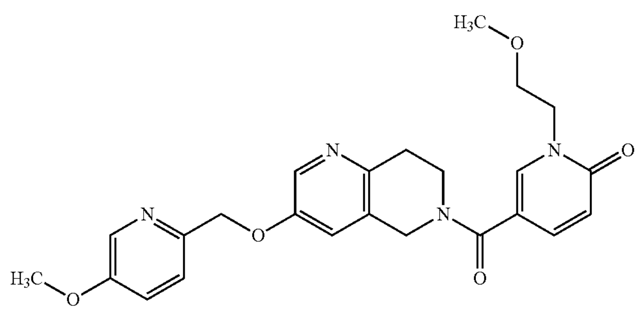 [SMILES: COCCn1cc(C(=O)N2CCc3ncc(OCc4ccc(OC)cn4)cc3C2)ccc1=O] |
| 25 | 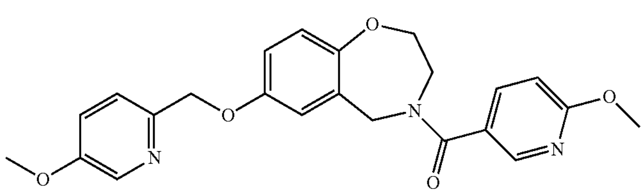 |
| 26 | 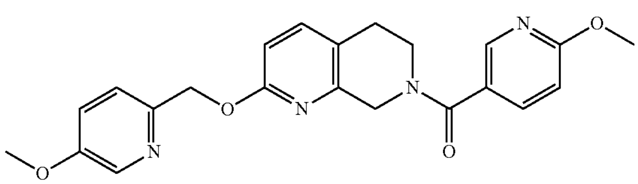 |
| 26.1 | 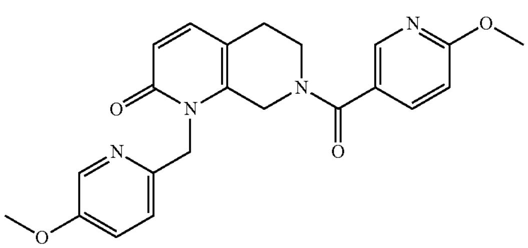 |
| 27 | 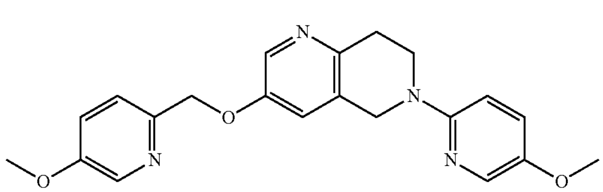 |

TABLE 1-continued

| Example | Structure |
|---|---|
| 27.1 | 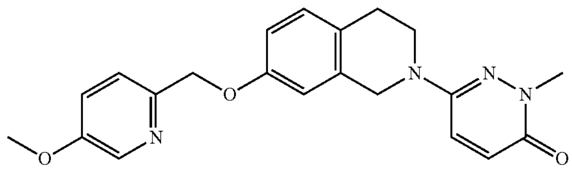 [SMILES: COc1ccc(COc2ccc3c(c2)CN(c2ccc(=O)n(C)n2)CC3)nc1] |
| 27.2 | 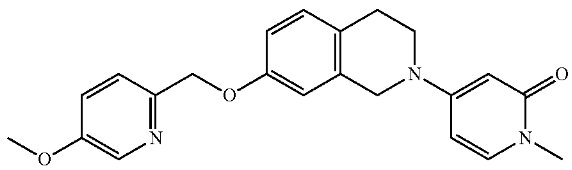 [SMILES: COc1ccc(COc2ccc3c(c2)CN(c2ccn(C)c(=O)c2)CC3)nc1] |
| 28 | 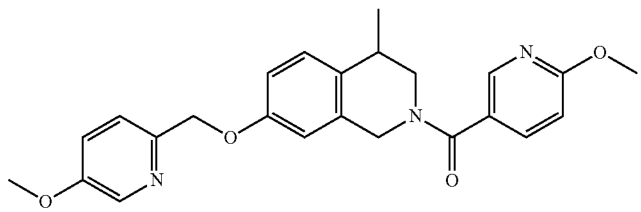 |
| 29 | 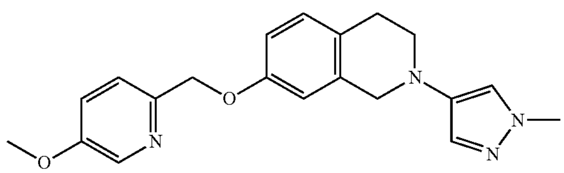 |
| 29.1 | 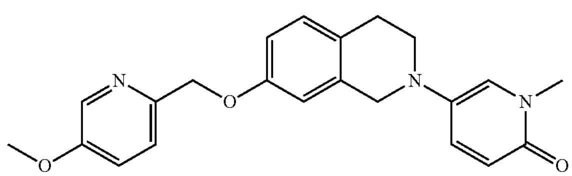 [SMILES: COc1ccc(COc2ccc3c(c2)CN(c2ccc(=O)n(C)c2)CC3)nc1] |
| 30 | 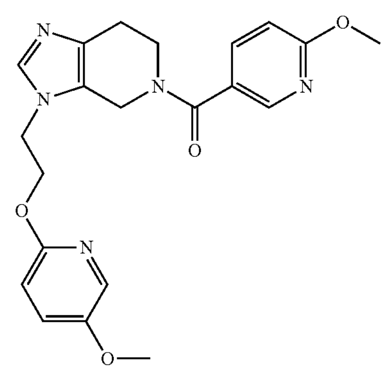 [SMILES: COc1ccc(OCCn2cnc3c2CN(C(=O)c2ccc(OC)nc2)CC3)nc1] |
| 31 | 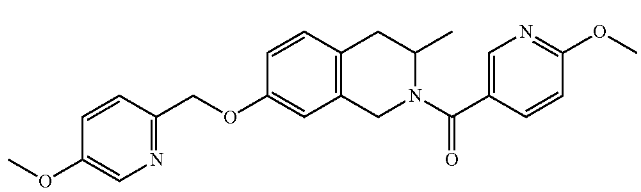 |

TABLE 1-continued
| Example | Structure |
|---|---|
| 32 | 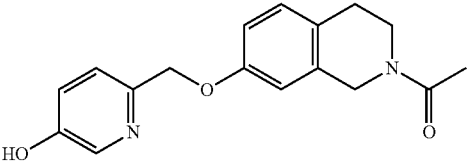 [SMILES: CC(=O)N1CCc2ccc(OCc3ccc(O)cn3)cc2C1] |
| 33 | 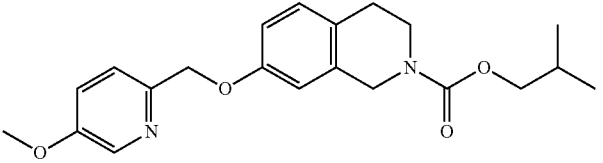 [SMILES: COc1ccc(COc2ccc3c(c2)CN(C(=O)OCC(C)C)CC3)nc1] |
| 34 | 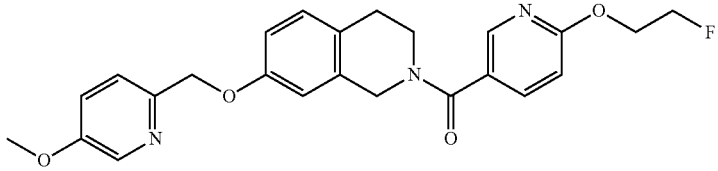 [SMILES: COc1ccc(COc2ccc3c(c2)CN(C(=O)c2ccc(OCCF)nc2)CC3)nc1] |
| 34.1 | 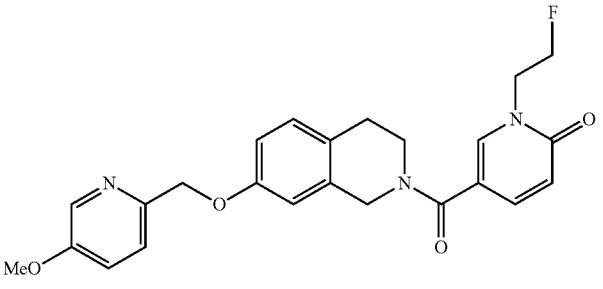 [SMILES: COc1ccc(COc2ccc3c(c2)CN(C(=O)c2ccc(=O)n(CCF)c2)CC3)nc1] |
| 35 | 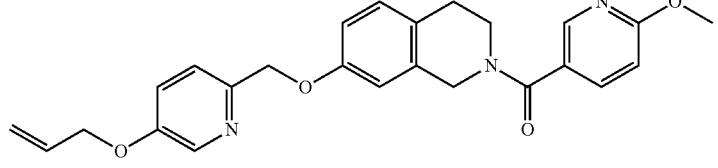 |
| 35.1 | 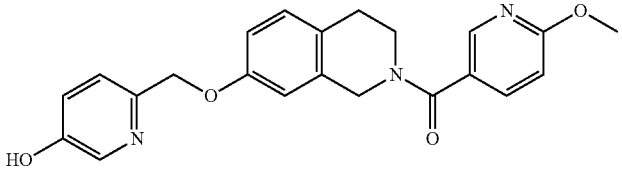 [SMILES: COc1ccc(C(=O)N2CCc3ccc(OCc4ccc(O)cn4)cc3C2)cn1] |
| 36 | 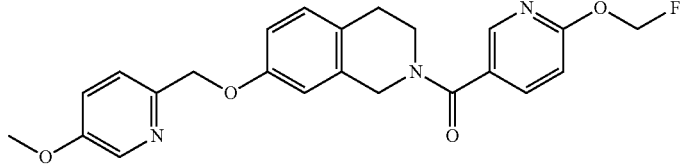 [SMILES: COc1ccc(COc2ccc3c(c2)CN(C(=O)c2ccc(OCF)nc2)CC3)nc1] |
| 37 | 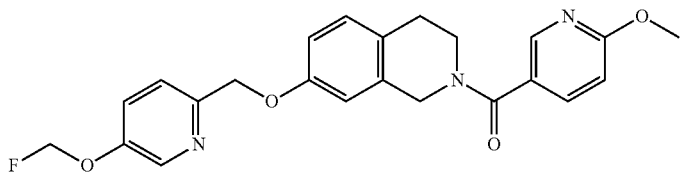 [SMILES: COc1ccc(C(=O)N2CCc3ccc(OCc4ccc(OCF)cn4)cc3C2)cn1] |

TABLE 1-continued

| Example | Structure |
|---------|-----------|
| 38 | 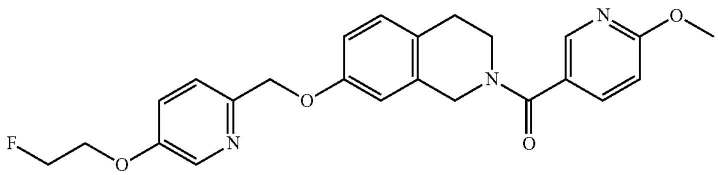 [SMILES: COc1ccc(C(=O)N2CCc3ccc(OCc4ccc(OCCF)cn4)cc3C2)cn1] |
| 39 | 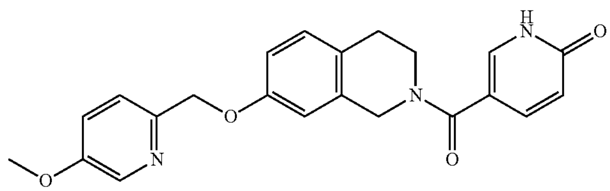 [SMILES: COc1ccc(COc2ccc3c(c2)CN(C(=O)c2ccc(=O)[nH]c2)CC3)nc1] |
| 40 | 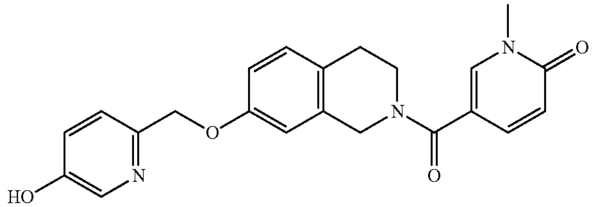 [SMILES: Cn1cc(C(=O)N2CCc3ccc(OCc4ccc(O)cn4)cc3C2)ccc1=O] |
| 41 | 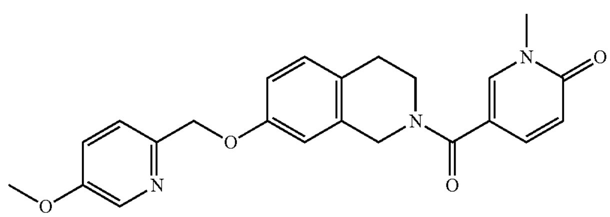 [SMILES: COc1ccc(COc2ccc3c(c2)CN(C(=O)c2ccc(=O)n(C)c2)CC3)nc1] |

In some embodiments, provided is a pharmaceutical composition comprising a compound described herein and a pharmaceutically acceptable carrier.

Diagnostic Methods and Uses

The compounds disclosed herein are useful for detecting a condition or disorder mediated, at least in part, by a protein susceptible to protein aggregation. Also provided is a method of generating diagnostic images, for example positron emission tomography (PET) images, in an individual comprising administering an effective amount of a compound described herein or an imaging agent comprising a compound described herein, and generating an image of a body part or body area of the individual. In some embodiments, a compound described herein is useful for detecting the presence or absence of huntingtin protein (HTT protein), or aggregates thereof, in a diagnostic image.

Also provided are methods of generating diagnostic images in a biological sample comprising contacting the biological sample with an effective amount of a compound or an imaging agent described herein and generating an image associated with the biological sample. In some embodiments, the contacting and the generating may be conducted in vitro. In some embodiments the contacting is in vivo and the generating is in vitro.

Also provided are methods for detecting the presence or absence of a pathologic process associated with a protein susceptible to protein aggregation, for example huntingtin protein (HTT protein), in an individual comprising: administering an effective amount of a compound or an imaging agent described herein; generating an image to detect the presence or absence of huntingtin protein (HTT protein) in the image; and detecting the presence or absence of a pathologic process. In some embodiments, the HTT protein is present as monomers, oligomers, or aggregates, or a combination thereof. In some embodiments, the huntingtin protein is present as aggregates thereof. In some embodiments, the individual has, or is discovered to have, Huntington's disease. Also provided are methods for detecting the presence or absence of a pathologic process associated with β-amyloid protein in an individual comprising: administering an effective amount of a compound or an imaging agent described herein; generating an image of a body part or body area of the individual; and detecting the presence or absence of the pathologic process. In some embodiments, the individual has, or is discovered to have, Alzheimer's Disease (AD). In some embodiments, the neurodegenerative disease is selected from Alzheimer's disease, amyotrophic lateral sclerosis, Huntington's disease, Parkinson's disease, Prion disease and spinocerebellar ataxias.

In some embodiments, the body part or body area is selected from head, spinal cord, limb, thorax, and/or abdomen. In some embodiments, the body part or body area is brain. In some embodiments, the HTT protein is found in basal ganglia. In some embodiments, the HTT protein is present in the brain, liver, heart, and/or muscle of the individual. In some embodiments, generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, generating an image comprises PET imaging. In some embodiments, the HTT protein is present in the basal ganglia, cortex, hippocampus, and/or brain stem of the brain of the individual. In some embodiments, the HTT protein is present as monomers, oligomers, or aggregates, or a combination thereof. In some embodiments, the huntingtin protein is present as aggregates thereof.

Also provided are diagnostic methods of using a compound or an imaging agent described herein to monitor disease progression in a patient by quantifying the change in levels of the protein susceptible to aggregation in the patient.

Provided are methods of generating diagnostic images using positron emission tomography (PET). PET imaging may be conducted as known to those of skill in the art, or as follows. PET imaging may involve the administration of a positron-emitting radionuclide tracer, for example, a compound or imaging agent described herein, to an individual. The tracer is then given sufficient time to associate with the protein of interest, when the individual is placed in a scanning device comprising a ring of scintillation detectors. An emitted positron travels through the individual's tissue for a short (isotope-dependent) distance, until it interacts with an electron. The interaction annihilates both the electron and the positron, producing a pair of photons. The photons are detected by a scintillator in the scanning device. Photons that do not arrive in pairs are ignored.

Also provided are methods of generating diagnostic images comprising PET with concurrent computed tomography imaging (PET/CT), with concurrent magnetic resonance imaging (PET/MRI), or single-photon emission computed tomography (SPECT) imaging. In general, computed tomography uses X-rays or gamma rays to detect the structure of the brain, while magnetic resonance imaging uses magnetic fields and radio waves.

In some embodiments, provided is a compound having suitable HTT protein aggregate or β-amyloid protein aggregate binding kinetics to function as imaging agents. Thus, a compound described herein may be characterized by one or more of: 1) a high affinity for such protein aggregates; 2) a low affinity for nearby structures; and/or 3) slow dissociation kinetics from such protein aggregates. Dissociation kinetics may be expressed as the dissociation rate constant $k_{diss}$ as defined in the equation below (wherein A and B refer to the protein aggregate and the imaging agent, and $k_{assn}$ is the association rate constant):

$$d[AB]/dt = k_{assn}[A][B] - k_{diss}[AB]$$

In some embodiments, the effective amount of the compound or imaging agent described herein comprises from about 0.1 to about 20 mCi. In some embodiments, the effective amount of the compound or imaging agent described herein comprises about 0.1, about 0.3, about 0.5, about 0.7, about 1, about 3, about 5, about 7, about 10, about 15, or about 20 mCi. In some embodiments, the effective amount of the compound or imaging agent described herein comprises about 10 mCi.

Suitable radionuclides that may be incorporated in a compound described herein include, but not limited, $^3$H (also written as T), $^{11}$C, $^{18}$F, $^{35}$S, $^{123}$I, $^{125}$I, $^{75}$Br, $^{76}$Br, $^{77}$Br, $^{82}$Br, $^{131}$I, $^{15}$O, $^{13}$N, and $^{211}$At. The radionuclide that is incorporated in the compound will depend on the specific imaging application. In some embodiments including PET imaging, compounds that incorporate a radionuclide selected from $^{11}$C, $^{18}$F, $^{123}$I, $^{131}$I, $^{75}$Br, $^{76}$Br or $^{77}$Br may be used. In certain applications incorporation of a chelating radionuclide such as $^{99m}$Tc may also be useful. In some embodiments, $^{18}$F may be preferable over $^{11}$C because with the longer half-life of $^{18}$F, imaging can be carried out long enough to allow a stronger signal to develop. In some embodiments, a compound or imaging agent described herein can be labeled with a positron emitting radionuclide or a gamma emitting radionuclide. Some examples of positron-emitting radionuclides include $^{15}$O, $^{13}$N, $^{11}$C, $^{18}$F, $^{76}$Br, and $^{124}$I, which have half-lives of about 2, 10, 20, 110 minutes, 16 hours, and 4.2 days respectively.

In some embodiments, a compound or an imaging agent described herein may be labelled with a positron emitter selected from $^{11}$C and $^{18}$F. Methods for the introduction of $^{11}$C may include, but are not limited to, alkylation with [$^{11}$C]iodomethane or [$^{11}$C]methyl triflate. Carbon-11 has a half-life of approximately 20 minutes, thus $^{11}$C needs to be generated in an on-site cyclotron, and is generally produced as [$^{11}$C]carbon dioxide. The [$^{11}$C]carbon dioxide is converted to the chemical species appropriate for the radiosynthesis (generally [$^{11}$C]iodomethane or the like), and the synthesis of the radiopharmaceutical is completed and used on-site in a PET imaging study after the appropriate radiochemical purity and specific activity have been determined. Typical methods of introducing $^{18}$F include but are not limited to displacement of a halide, tosylate, or other leaving group with [$^{18}$F]tetrabutylamonium fluoride or [$^{18}$F]potassium fluoride kryptofix-222. Fluorine-18 has a half life of approximately 110 minutes, thus synthesis of [$^{18}$F] radiopharmaceuticals need not necessarily have to occur at the site of the cyclotron nor proximal to the PET imaging study center. General methods for the introduction of these positron emitters are described in the literature (e.g., see Miller et al., *Angewandte Chemie International Edition*, 47 (2008), 8998-9033).

As will be recognized, the steps of the methods described herein need not be performed any particular number of times or in any particular sequence. Additional objects, advantages and novel features of the disclosure will become apparent to those skilled in the art upon examination of the examples provided below, which are intended to be illustrative and are not limiting.

Indications and Treatment Methods

A compound or an imaging agent described herein may be useful for detecting a condition or disorder mediated, at least in part, by a protein susceptible to aggregation. In some embodiments, a compound or an imaging agent described herein are useful for detecting conditions or disorders mediated, at least in part, by HTT. In some embodiments, treatment of a condition or disorder mediated, at least in part, by a protein susceptible to aggregation, may comprise administration of a compound or an imaging agent described herein. Treatment may include coadministration of a compound or an imaging agent described herein and one or more other therapeutic agents and/or therapies.

In some embodiments, provided is a method of treating or preventing a condition or disorder mediated, at least in part, by a protein susceptible to aggregation in a patient in need thereof, comprising administering to the patient a therapeutically effective amount of a compound or an imaging agent described herein.

Exemplary conditions or disorders are as follows.

Huntington's Disease (HD)

Huntington's disease (HD) is an inherited progressive neurodegenerative disorder, characterized by motor, cognitive, and psychiatric deficits as well as neurodegeneration and brain atrophy. Atrophy may begin in the striatum and cortex and extend to other subcortical brain regions. HD belongs to a family of neurodegenerative diseases in which an expanded CAG repeat tract results in long stretches of polyglutamine (polyQ) in an encoded protein. The family also includes dentatorubral-pallidoluysian atrophy (DRPLA), spinal and bulbar muscular atrophy (SBMA) and the spinocerebellar ataxias (SCAs). In HD, the selective neurodegeneration of the γ-aminobutyric acid-releasing spinyprojection neurons of the striatum had been observed, although neuron loss in many other brain regions has also been reported. Symptoms of HD include loss of motor control, psychiatric symptoms, memory and/or cognitive impairment.

HD protein huntingtin (HTT protein) is a 348-kDa multidomain protein that contains a polymorphic glutamine/proline-rich domain at its amino-terminus. The number of CAG repeats in the $IT_{15}$ gene that encodes the varies from 6 to 35 in healthy individuals; repeats of 36 or more define an HD allele. The length of the CAG expansion has been inversely correlated with age of disease onset, with cases of juvenile onset characterized by expansions of more than 60 repeats. The longer polyQ domain is believed to induce conformational changes in the HTT protein, which causes it to form intracellular aggregates that, in many, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

The part of the brain most affected by HD, and thus believed to be most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

Basal ganglia are a group of subcortical nuclei responsible primarily for motor control, as well as other roles such as motor learning, executive functions and behaviors, and emotions. Disruption of the basal ganglia network are believed to contribute to several movement disorders. Normal function of the basal ganglia requires fine tuning of neuronal excitability within each nucleus to determine the degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

Provided are methods for generating an image of a body part or body area of an individual involving administering a compound or an imaging agent described herein to the individual. In some embodiments the compound or imaging agent is administered into the individual's vascular system. The compound or imaging agent may pass through the blood-brain barrier. Thus, generating an image may comprise generating an image of at least part of the individual's brain, for example, the part to which the compound has distributed.

In some embodiments, the pathologic process is a condition or disorder selected from Huntington's disease (HD), dentatorubropallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma. In some embodiments, the pathologic process is a neurodegenerative disease selected from Alzheimer's disease, amyotrophic lateral sclerosis, Huntington's disease, Parkinson's disease, Prion disease and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the neurodegenerative disease is Huntington's disease.

Imaging Agents and Administration Thereof

An imaging agent will generally comprise a compound described herein labeled with a positron emitting radionuclide. Imaging agents labeled with positron emitting radionuclides are generally administered via intravenous injection within one hour of synthesis due to the short half-life of the radionuclides. The amount of imaging agent required will normally be determined by the prescribing physician. The dose may vary according to the quantity of emission from the radionuclide used. Those with ordinary skill in the art will appreciate that an effective amount will be the amount of compound sufficient to produce emissions in the range of from about 0.1 to about 20 mCi, or about 1 to about 5 mCi. The mass of labeled compound in an effective amount of imaging agent may be about 0.1 to about 500 mg.

The following example provides an illustrative, non-limiting, procedure that may be utilized when performing PET imaging studies on an individual in a clinical setting. The individual may be either unmedicated or pre-medicated with an unlabeled compound. The individual may be fasted for at least 12 hours allowing water intake ad libitum. A 20 G two inch venous catheter may be inserted into the contralateral ulnar vein for administration of the imaging agent.

The human subject is positioned in the PET camera and a tracer dose of imaging agent is administered via i.v. catheter. Either arterial or venous blood samples are taken at appropriate time intervals throughout the PET scan in order to analyze and quantitate the fraction of umetabolized compound in plasma. Images are acquired for up to 120 minutes. Within ten minutes of the injection of radiotracer and at the end of the imaging session, 1 ml blood samples are obtained for determining the plasma concentration of any unlabeled imaging agent compound (or other compound of intervention) which may have been administered before the PET tracer.

Tomographic images may be obtained through image reconstruction. For example, for determining the distribution of imaging agent, regions of interest (ROIs) are drawn on the reconstructed image. Regions of interest in a brain image may include, for example, the striatum, cerebellum, or basal ganglia. Imaging agent uptake over time in these regions may be used to generate time activity curves (TAC). Data may be expressed as radioactivity per unit time per unit volume (e.g., µCi/cc/mCi injected dose), or as radioactivity per unit volume. TAC data may be processed with various methods known in the field to yield quantitative parameters, an example of which is Binding Potential (BP).

Generally, a compound or an imaging agent described herein may be administered to a patient in need thereof via any suitable route. Routes of administration may include, for example, parenteral administration, including subcutaneous, intramuscular, intravenous, by means of, for example a drip patch. Further suitable routes of administration include, but are not limited to, oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

With regard to PET imaging, administration of a compound or an imaging agent described herein to the individual may be intravenous. The pharmaceutical composition may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables. Such solutions may be formulated as 0.01%-10% isotonic solutions, pH 5-7, with appropriate salts.

The compound or imaging agent described herein may be administered parenterally in a sterile medium. Parenteral administration includes subcutaneous injections, intravenous, intramuscular, intrathecal injection or infusion techniques. The compound or imaging agent described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

A compound or an imaging agent described herein may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

The dose of the compound or imaging agent described herein depends upon a variety of factors including the particular pathologic process to be treated or detected, the physiology of the individual, the severity of the symptoms, the route of administration, the frequency of the dosage interval, the particular compound utilized, the efficacy, toxicology profile, pharmacokinetic profile of the compound, and the presence of any deleterious side-effects, among other considerations. The dose under a given set of circumstances generally will be determined by a practitioner on a case-by-case basis based on the above and other factors.

The compound or imaging agent described herein is typically administered at a dosage level and in a manner determined by a practitioner such as a physician. For example, the compound or imaging agent can be administered, in single or multiple doses, at a dosage level of generally 0.001-100 mg/kg, for example, 0.01-100 mg/kg, such as 0.1-70 mg/kg, for example, 0.5-10 mg/kg. The dose can be, for example, for administration once a day or twice a day. Unit dosage forms can contain generally 0.01-1000 mg of the compound or imaging agent described herein, for example, 0.1-50 mg. For intravenous administration, the compound or imaging agent can be administered, in single or multiple dosages, at a dosage level of, for example, 0.001-50 mg/kg, such as 0.001-10 mg/kg, for example, 0.01-1 mg/kg. Unit dosage forms can contain, for example, 0.1-10 mg of the compound or imaging agent.

In some embodiments, the compound or imaging agent described herein is administered as a pharmaceutical composition. Accordingly, provided are pharmaceutical compositions comprising at least one compound or imaging agent described herein, together with at least one pharmaceutically acceptable vehicle chosen from carriers, adjuvants, and excipients. A compound or imaging agent of the present disclosure can be formulated into a pharmaceutical composition using techniques known to those of skill in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound or imaging agent may be sufficient to provide a practical quantity of material for administration per dose of the compound or imaging agent.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound or imaging agent described herein.

Effective concentrations of at least one compound or imaging agent described herein are mixed with a suitable pharmaceutically acceptable vehicle. In instances in which the compound or imaging agent exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous buffer, for example, sodium bicarbonate.

Upon mixing or addition of a compound or imaging agent described herein, the resulting mixture may be a solution, suspension, emulsion or the like. The form of the resulting mixture depends upon a number of factors, including the intended mode of administration and the solubility of the compound or imaging agent in the chosen vehicle. The effective concentration sufficient for imaging or treatment may be empirically determined according to known methods in the art.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of the compound or imaging agent described herein. In some embodiments, oral pharmaceutical compositions contain at least 5% (weight %) of the compound or imaging agent. Some embodiments contain from 25% to 50% or from 5% to 75% of the compound or imaging agent.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound or imaging agent described herein can be incorporated into oral liquid preparations such as aqueous or oily suspensions, solutions, emulsions, syrups, or elixirs, for example. Furthermore, pharmaceutical compositions containing the compound or imaging agent described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoatc and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions containing the compound or imaging agent in admixture with excipients suitable for the manufacture of aqueous suspensions are provided. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the compound or imaging agent in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of an oil-in-water emulsion. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

The pharmaceutical composition may also be coated by conventional methods, typically with pH or time-dependent coatings, such that the compound or imaging agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

The compound or imaging agent described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound or imaging agent described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Topical pharmaceutical compositions comprising at least one compound, or an isotopically labeled analog, pharmaceutically acceptable salt, solvate, prodrug, stereoisomer, or mixture of stereoisomers thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium poly acrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, and ethylene glycol monostearate.

The compound or imaging agent described herein may also be formulated for transdermal administration as a transdermal patch.

The compound or imaging agent described herein may also be administered in a liposome delivery system. Liposomes may be classified as small unilamellar vesicles, large unilamellar vesicles, and multilamellar vesicles. Liposomes can be formed from a variety of amphiphathic molecules, in particular phospholipids. Constituents of liposomes may include cholesterol, stearylamine and/or phosphatidylcholines. Liposomes are suitable for various routes of administration including topical and injection into various tissues. Thus, intravitreal (e.g., in treatment of glaucoma), intraperitoneal, intravenous, intravascular, intraarticular, and intramuscular administration of liposomes is contemplated.

Other pharmaceutical compositions useful for attaining systemic delivery of the compound or imaging agent include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound or imaging agent described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of the compound or imaging agent described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Packaging

Also provided are packaged pharmaceutical compositions. Such packaged compositions include a pharmaceutical composition comprising or imaging agent described herein, and instructions for using the composition to treat a subject (typically a human patient). In some embodiments, the instructions are for using the pharmaceutical composition to detect a condition or disorder described herein. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound or imaging agent can be administered alone, as mixtures, or in combination with other active agents.

Combination Therapy

The methods described herein include methods for detecting, treating or preventing a condition or disorder described herein, for example, Huntington's disease, comprising administering to a subject, simultaneously or sequentially, a compound or imaging agent described herein and one or more additional agents. In methods using simultaneous administration, the agents can be present in a combined composition or can be administered separately. When used in combination with one or more additional pharmaceutical agent or agents, a compound or imaging agent described herein may be administered prior to, concurrently with, or following administration of the additional active agent or agents.

Also provided is a pharmaceutical composition comprising a compound or imaging agent described herein and one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided is a packaged pharmaceutical composition containing a pharmaceutical composition comprising a compound or imaging agent described herein, and another composition comprising one or more additional pharmaceutical agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In some embodiments, the active agent is carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, or risperidone.

Also provided are methods for treating or preventing Alzheimer's disease, including treating memory and/or cognitive impairment associated with Alzheimer's disease, comprising administering to a subject, simultaneously or sequentially, a compound or imaging agent described herein and one or more additional agents. In some embodiments, the active agent is Reminyl®, Cognex®, Aricept®, Exelon®, Akatinol®, Neotropin™, Eldepryl®, Estrogen or Clioquinol.

Also provided is use of a compound or imaging agent described herein for the manufacture of a medicament for use in diagnosis, prevention, or treatment of a condition or disorder described herein.

Synthesis of the Compounds

A compound described herein may be prepared using the methods disclosed herein and routine modifications thereof, which will be apparent given the disclosure herein and methods well known in the art. Conventional and well-known synthetic methods may be used in addition to the teachings herein. The synthesis of a typical compound described herein may be accomplished as described in the following examples. If available, reagents may be purchased commercially, e.g., from Sigma Aldrich or other chemical suppliers.

A compound described herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, a compound described herein may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplemental (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

Incorporation of a label into a compound or imaging agent described herein may be conducted by reacting an appropriate starting material(s) with a reagent including a radioactive isotope.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Compounds were named with the aid of the Cambridgesoft Chemistry Cartridge (v. 16.0.0.82) software.

Analytical Methods

Acidic Phase HPLC Methods

Analytical HPLC-MS (METCR1673) was performed on Shimadzu LCMS-2010EV systems using a reverse phase Supelco Ascentis Express column (2.7 µm, 2.1×30 mm), gradient 5-100% B (A=water/0.1% formic acid, B=acetonitrile/0.1% formic acid) at a column temp of 40° C. over 1.5 min then 100% B for 0.1 min, injection volume 3 µL, flow=1.0 mL/min. UV spectra were recorded at 215 nm using a SPD-M20A photo diode array (PDA) detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, HPLC-MS (METCR1410) was performed on Shimadzu LCMS-2010EV systems using a reverse phase Kinetix Core-Shell C18 column (5 µm, 2.1×50 mm) at a column temp of 40° C., gradient 5-100% B (A=water/0.1% formic acid, B=acetonitrile/0.1% formic acid) over 1.2 min, then 100% B over 0.1 min, injection volume 3 µL, flow=1.2 mL/min. All other aspects of the method were unchanged.

Alternatively, (METCR1416) analytical HPLC-MS was performed on Shimadzu LCMS-2010EV systems using reverse phase Waters Atlantis dC18 columns (3 µm, 2.1×100 mm), gradient 5-100% B (A=water/0.1% formic acid, B=acetonitrile/0.1% formic acid) at a column temp of 40° C. over 5.0 min then 100% B for 0.4 min, injection volume 3 µL, flow=0.6 mL/min. UV spectra were recorded at 215 nm using a SPD-M20A PDA detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 µm, 2.1 mm×100 mm at a column temp of 40° C., gradient 5-100% B (A=water/0.1% formic acid; B=acetonitrile/0.1% formic acid) over 5.3 min, then 100% B for 0.5 min, flow=0.6 ml/min. UV spectra were recorded at 215 nm using a Waters Acquity PDA detector. Mass spectra were obtained over the range m/z 150 to 850 at a sampling rate of 2 scans per second using a Waters ZQ. Data were integrated and reported using OpenLynx software.

Alternatively, (MET-AMRI001) mass spectra and LCMS analyses were obtained using a Waters Acquity SQD (ESI, UP-LCMS). HPLC analyses were obtained on an XBridge C18 column, 3.5 µm (4.6×150 mm), eluted according to solvent gradient Method 1. Detection was by UV at 254 and 215 nm.

Method 1

| Time (min) | Flow (mL/min) | % A | % B |
|---|---|---|---|
| 0.0 | 1.0 | 95 | 5 |
| 20.0 | 1.0 | 0 | 100 |
| 25.0 | 1.0 | 0 | 100 |

A = Water with 0.1% v/v Trifluoroacetic Acid
B = Acetonitrile with 0.1% v/v Trifluoroacetic Acid Basic Phase HPLC Methods Analytical HPLC-MS (METCR0990), was performed on Hewlett Packard HPLC systems using reverse phase Phenomenex Gemini C18 columns (3 µm, 2.0×50 mm), at a column temp of 60° C.; gradient 1-100% B (A=2 mM ammonium bicarbonate in water buffered to pH10, B=acetonitrile) over 1.8 min then 100% B for 0.3 min, injection volume 3 µL, flow=1 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

Analytical HPLC-MS (METCR1600), was performed on Hewlett Packard HPLC systems using reverse phase Phenomenex Gemini C18 columns (3 µm, 2.0×100 mm), gradient 5-100% B (A=2 mM ammonium bicarbonate in water buffered to pH 10, B=acetonitrile) over 5.5 min then 100% B for 0.4 min, injection volume 3 µL, flow=0.5 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

The METCR1600 method was subsequently replaced with the METCR1603 method where the flow rate increased to 0.6 mL/min. All other parameters were unchanged.

Alternatively, (MET-uHPLC-AB-102) analytical HPLC-MS were performed on a Waters Acquity UPLC system with Waters PDA and ELS detectors using a Waters UPLC® CSH™ (1.7 µm, 2.1×100 mm) column, at a column temp of 40° C.; gradient 5-100% B (A=2 mM ammonium bicarbonate in water buffered to pH 10, B=acetonitrile) over 5.3 min then 100% B for 0.5 min, injection volume 1 µL, flow=0.6 mL/minute. UV spectra were recorded at 215 nm using a Waters Acquity PDA detector. Mass spectra were obtained over the range m/z 150 to 850 at a sampling rate of 2 scans per second using a Waters Quattro Premier XE. Data were integrated and reported using OpenLynx software.

General Experimental Procedures

Compounds of the present disclosure may be synthesized in accordance with the general reaction schemes and/or examples described below. The general schemes may be altered by substitution of the starting materials with other materials having similar structures to result in corresponding products. The structure of the desired product will generally make apparent to a person of skill in the art the required starting materials.

Scheme 1 provides exemplary synthetic routes for the synthesis of compounds provided herein (e.g., compounds of Formula I). The compounds of Formula I, or other formulas or compounds disclosed herein, are typically prepared by first providing the core Formula X(a1) or X(a2) and then attaching the desired substituents using suitable conditions (e.g., coupling, amide bond formation, etc.).

In some embodiments, synthesis of a compound of Formula (I) proceeds according to Scheme F In Scheme 1, a compound of formula X(a1) is converted into a compound of formula X(b1) or X(c1) (corresponding to compounds of formula (I) where $X^1$ is N—$F^2$—$R^2$), or a compound of Formula X(a2) is converted into a compound of formula X(b2) or X(c2) (corresponding to compounds of formula (I) where $X^2$ is N—$F^2$—$R^2$). The compound of formula X(b1) or X(c1), respectively, can then be converted into a compound of formula X(d1), or the compound of formula X(b2) or X(c2) can be converted into a compound of formula X(d2). Either a compound of formula X(d1) or X(d2) may subsequently be converted into a compound of formula (I). In Scheme 1, $L^1$, $F^2$, $R^1$, $R^2$, $X^3$, $Z^1$, $Z^2$, $Z^3$ and p are as defined in formula (I). The compound of formula (I) may be obtained by known methods or by methods described herein, specifically as described with respect to synthesis of any of Method 1 to Method 41.

Scheme 1

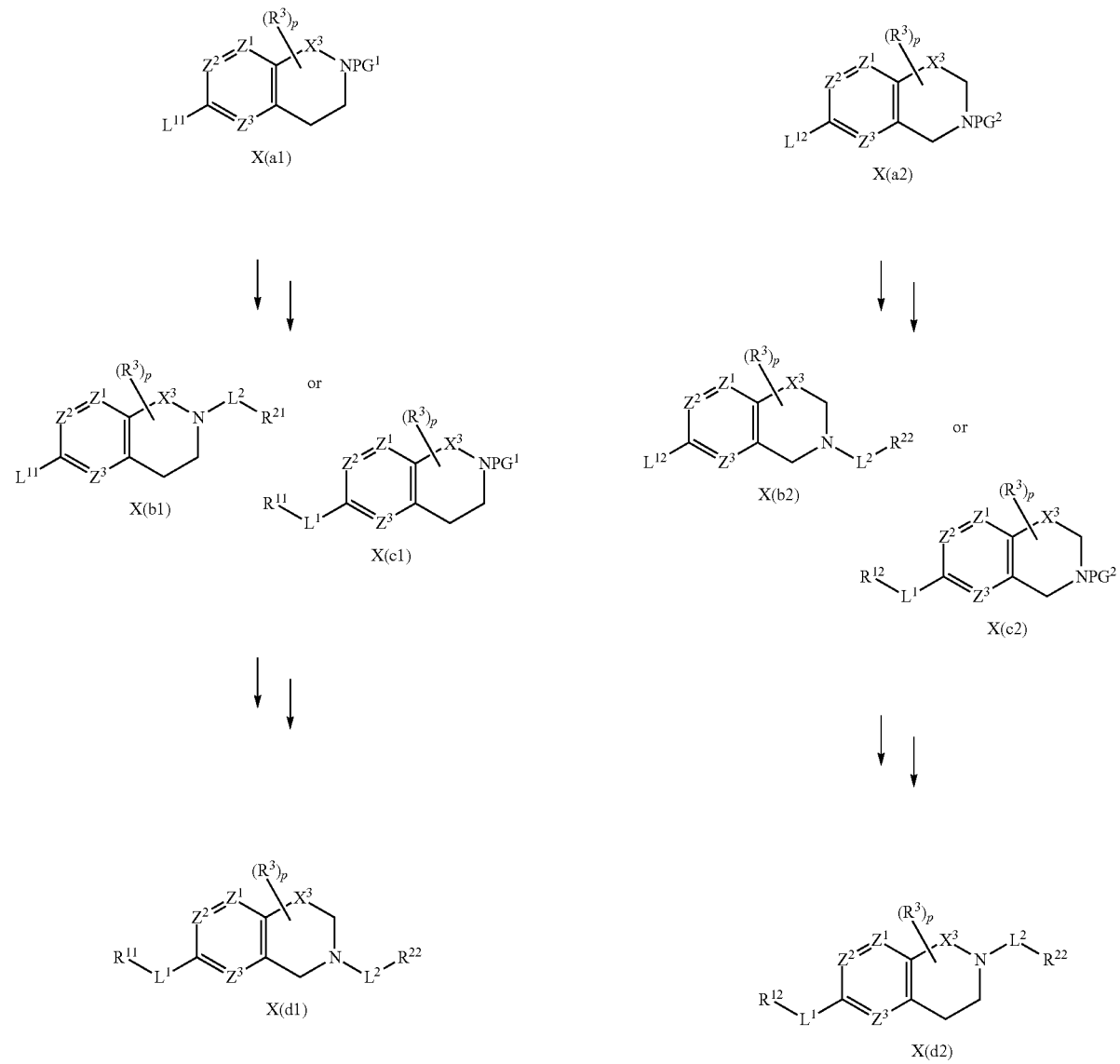

-continued

Formual (I)

In Scheme 1, Each of $PG^1$ and $PG^2$ is independently hydrogen or a suitable nitrogen protecting group, e.g., a carbamate (e.g., tert-butoxycarbonyl and the like) or a sulfur derivative (e.g., $S(O)_2CH_3$), or may be an acyl halide, such as an acyl chloride. Where $PG^1$ or $PG^2$ is a protecting group, the group may be removed under suitable conditions (e.g., when Boc, by TFA or HCl). Where $PG^1$ or $PG^2$ is hydrogen, a moiety $R^{21}$ or $R^{22}$ may be appended under suitable conditions, for example, by (sulfon)amide coupling conditions (e.g., where $R^{21}$ or $R^{22}$ is a carboxylic acid, HATU or EDCI and DIPEA, or where $R^{21}$ or $R^{22}$ is an acyl halide or sulfonyl halide, a base such as DIPEA). $PG^1$ or $PG^2$ may also undergo displacement under nucleophilic aryl coupling conditions, for example, using a metal catalyst (e.g., $Pd_2(dba)_3$, RuPhos, $Pd(OAc)_2$) optionally in contact with a ligand (e.g., BINAP, 2,2'-bis(diphenylphosphino)-1,1'-binaphthyl, CyJohnPhos) in an inert solvent (e.g., 1,4-dioxane, DMF, THF), in the presence of a base (e.g., $Cs_2CO_3$, NaO/Bu, KO/Bu, NaH, $Na_2CO_3$). $PG^1$ or $PG^2$ may also undergo displacement under nucleophilic conditions with a suitable electrophile (e.g., a primary halide) in the presence of a base (e.g., $Cs_2CO_3$) and optionally potassium iodide. When $PG^1$ or $PG^2$ is an acyl halide, $R^{21}$ or $R^{22}$ may be appended by nucleophilic displacement of the halide by a nucleophile, for example, a secondary amine.

$L^{11}$ and $L^{12}$ may be a hydroxyl, a hydroxyl protected by a hydroxyl protecting group (e.g., a benzyl) or a leaving group (e.g., a halide). When $L^{11}$ or $L^{12}$ is a hydroxyl, $R^{11}$ or $R^{12}$ may be appended by a nucleophilic displacement reaction such as a nucleophilic halide displacement with an alkyl halide partner (e.g., an alkyl chloride or bromide, a base such as $Cs_2CO_3$, and optionally potassium iodide), or a Mitsonobu reaction (e.g., in the presence of CMBP) with a suitable alcohol (e.g., a primary alcohol) partner. When $L^{11}$ or $L^{12}$ is a leaving group, $R^{11}$ or $R^{12}$ may be appended under nucleophilic aryl coupling conditions, for example, using a metal catalyst (e.g., $Pd_2(dba)_3$, RuPhos, $Pd(OAc)_2$) optionally in contact with a ligand (e.g., BINAP, 2,2'-bis(diphenylphosphino)-1,1'-binaphthyl, CyJohnPhos) in an inert solvent (e.g., 1,4-dioxane, DMF, THF), in the presence of a base (e.g., $Cs_2CO_3$, NaOfBu, KOfBu, NaH, $Na_2CO_3$). When $L^{11}$ or $L^{12}$ is an amine, $R^{11}$ or $R^{12}$ may be appended under amide coupling conditions (e.g., where $R^{11}$ or $R^{12}$ is a carboxylic acid, HATU or EDCI, and DIPEA).

$R^{11}$ may be $R^1$ or a derivative thereof, such as a hydroxyl derivative (e.g., an allyl alcohol corresponding to a hydroxyl of $R^1$, or a hydroxyl corresponding to a methyl ether of $R^1$). $R^{21}$ may be $R^2$ or a derivative thereof, such as a hydroxyl protected derivative (e.g., an allyl alcohol corresponding to $R^1$). $R^{11}$ may be converted to $R^1$, or $R^{21}$ to $R^2$, under conditions known in the art or as described herein.

Commercially available reagents and solvents (HPLC grade) were used without further purification. $^1$H NMR spectra were recorded on a Bruker DRX 500 MHz spectrometer or Bruker DPX 250 MHz spectrometer or a Bruker AVANCE 300 or on a Bruker AVANCE 500 spectrometer in deuterated solvents. Chemical shifts (δ) are in parts per million. Flash column chromatography refers to automated purification on Biotage Isolera systems using an appropriately sized SNAP or KPNH pre-packed silica columns and the solvents recorded in the experimental section. Thin-layer chromatography (TLC) analysis was performed with Kieselgel 60 F254 (Merck) plates and visualized using UV light. SCX chromatography was performed with Biotage Isolute Flash SCX-2 loading the sample in methanol and eluting with methanol then 5% ammonia in methanol.

All example compounds display an LC purity of >95% unless stated otherwise.

Method 1

Scheme for Method 1

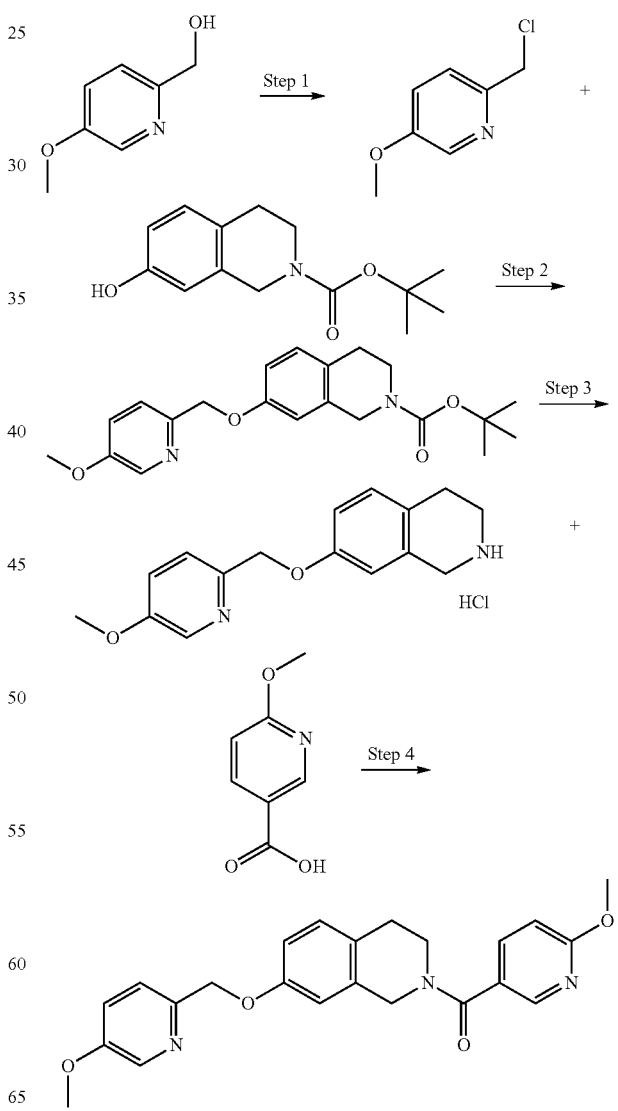

Example 1: 7-[(5-Methoxypyridin-2-yl)methoxy]-2-(6-methoxypyridine-3-carbonyl)-1,2,3,4-tetrahydroisoquinoline

2-(Chloromethyl)-5-methoxypyridine (5-Methoxypyridin-2-yl)methanol (200 mg, 1.37 mmol) was dissolved in DCM (5 mL), thionyl dichloride (198 μL, 2.73 mmol) was added and the reaction mixture was stirred at rt under nitrogen for 1.5 hours. The reaction mixture was concentrated under reduced pressure and the residue was co-distilled with DCM (3×10 mL) and concentrated to dryness to give the title compound. Tr (METCR1410)=0.82 min, (ES$^+$) (M+H)$^+$ 158/160.

tert-Butyl 7-[(5-methoxypyridin-2-yl)methoxy]-1,2,3,4-tetrahydroisoquinoline-2-carboxylate 2-(Chloromethyl)-5-methoxypyridine (100 mg, 0.63 mmol), tert-butyl 7-hydroxy-3,4-dihydro-1H-isoquinoline-2-carboxylate (158 mg, 0.63 mmol), KI (105 mg, 0.63 mmol) and Cs$_2$CO$_3$ (419 mg, 1.27 mmol) were dissolved in DMF (5 mL) and the reaction mixture was stirred at rt for 19 hours. The reaction mixture was concentrated under reduced pressure and the residue was washed with water. Purification by column chromatography (Silica, 0-80% EtOAc in heptanes) gave the title compound. Tr (METCR1410)=1.24 min, (ES$^+$) (M+H)$^+$ 371, 94%. $^1$H NMR (500 MHz, DMSO-d$_6$) δ 8.27 (d, J=2.7 Hz, 1H), 7.44 (d, J=8.5 Hz, 1H), 7.41 (dd, J=8.6, 2.8 Hz, 1H), 7.05 (d, J=8.4 Hz, 1H), 6.88-6.77 (m, 2H), 5.06 (s, 2H), 4.44 (s, 2H), 3.83 (s, 3H), 3.51 (t, J=5.9 Hz, 2H), 2.68 (t, J=5.8 Hz, 2H), 1.42 (s, 9H).

7-[(5-Methoxypyridin-2-yl)methoxy]-1,2,3,4-tetrahydroisoquinolin-2-ium chloride (Example 1.30)

tert-Butyl 7-[(5-methoxypyridin-2-yl)methoxy]-1,2,3,4-tetrahydroisoquinoline-2-carboxylate (120 mg, 0.32 mmol) was suspended in 4 N HCl in dioxane (10 mL) and sonicated for 5 minutes. The suspension was stirred at rt for 3.5 hours. The resultant material was filtered to give the title compound. Tr (METCR1410)=0.75 min, (ES$^+$) (M+H)$^+$ 271. $^1$H NMR (500 MHz, DMSO-d$_6$) δ 9.34 (s, 2H), 8.35 (dd, J=2.2, 1.1 Hz, 1H), 7.57 (d, J=2.3 Hz, 2H), 7.14 (d, J=8.4 Hz, 1H), 6.97-6.87 (m, 2H), 5.14 (s, 2H), 4.20 (t, J=4.5 Hz, 2H), 3.86 (s, 3H), 3.32 (d, J=6.3 Hz, 2H), 2.92 (t, J=6.2 Hz, 2H).

7-[(5-Methoxypyridin-2-yl)methoxy]-2-(6-methoxypyridine-3-carbonyl)-1,2,3,4 tetrahydroisoquinoline 6-Methoxypyridine-3-carboxylic acid (16 mg, 0.11 mmol) was dissolved into DMF (2 mL) and 7-[(5-methoxypyridin-2-yl)methoxy]-2-(6-methoxypyridine-3-carbonyl)-1,2,3,4 tetrahydroisoquinoline (33 mg, 0.11 mmol), HATU (40.9 mg, 0.11 mmol) and DIPEA (60 μL, 0.32 mmol) were added. The reaction mixture was sonicated for 5 minutes and the reaction mixture was stirred at rt for 19 hours. The reaction mixture was concentrated under reduced pressure and the residue dissolved in water (10 mL), the product was extracted with ethyl acetate (2×75 mL). The organic layers were combined and concentrated under reduced pressure. Purification by basic preparative HPLC gave the title compound.

$^1$H NMR (353K, 250 MHz, DMSO-d$_6$) δ 8.42-8.16 (m, 2H), 7.78 (dd, J=8.5, 2.4 Hz, 1H), 7.50-7.24 (m, 2H), 7.18-7.01 (m, 1H), 6.94-6.77 (m, 3H), 5.07 (s, 2H), 4.66 (s, 2H), 3.93 (s, 3H), 3.85 (s, 3H), 3.70 (t, J=6.0 Hz, 2H), 2.80 (t, J=6.1 Hz, 2H). Tr (MET-uHPLC-AB-101)=2.82 min, (ES$^+$) (M+H)$^+$ 406.

Also prepared by this route:

| Example | Structure | Mol. Weight | LCMS data |
|---|---|---|---|
| 1.1 | 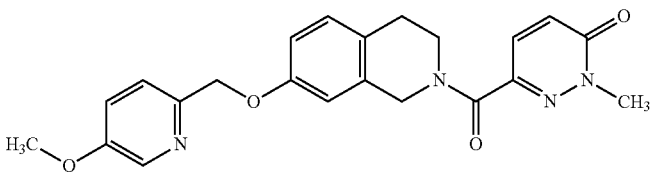 | 406.44 | Tr (MET-uHPLC-AB-101) = 2.4 min, (ES$^+$) (M + H)$^+$ 407 |
| 1.2 | 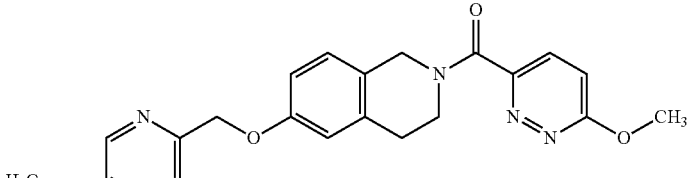 | 406.44 | Tr (MET-uHPLC-AB-101) = 2.53 min, (ES$^+$) (M + H)$^+$ 407 |
| 1.3 | 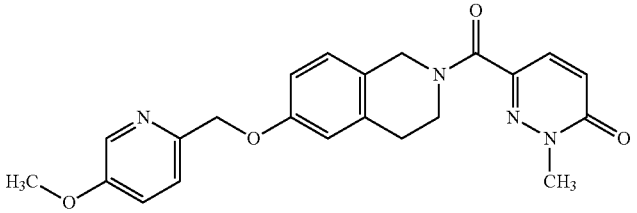 [SMILES: COc1ccc(COc2ccc3c(c2)CCN(C(=O)c2ccc(=O)n(C)n2)C3)nc1] | 406.44 | Tr (MET-uHPLC-AB-101) = 2.35 min, (ES$^+$) (M + H)$^+$ 407 |

-continued

| Example | Structure | Mol. Weight | LCMS data |
|---|---|---|---|
| 1.4 | 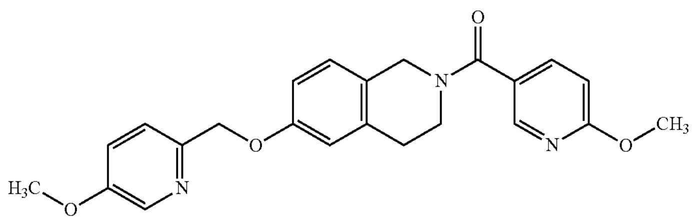 | 405.45 | Tr (MET-uHPLC-AB-101) = 2.78 min, (ES+) (M + H)+ 406 |
| 1.5 | 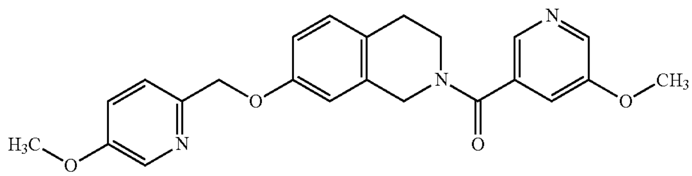 | 405.45 | Tr (MET-uHPLC-AB-101) = 2.57 min, (ES+) (M + H)+ 406 |
| 1.6 | 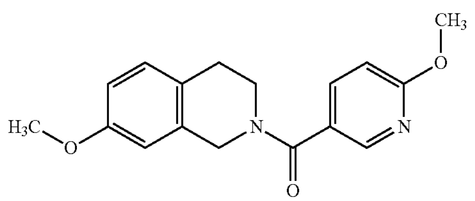 | 298.34 | Tr (MET-uHPLC-AB-101) = 2.9 min, (ES+) (M + H)+ 299 |
| 1.7 | 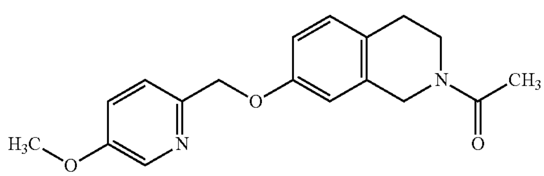 [SMILES: COc1ccc(COc2ccc3c(c2)CN(C(C)=O)CC3)nc1] | 312.37 | Tr (MET-uHPLC-AB-101) = 2.34 min, (ES+) (M + H)+ 313 |
| 1.8 | 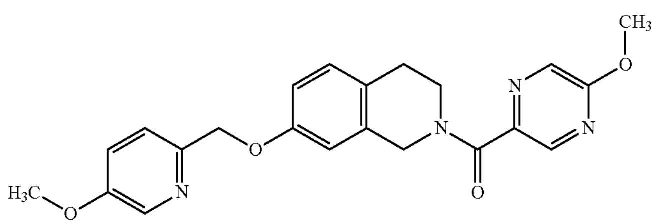 | 406.44 | Tr (MET-uHPLC-AB-101) = 2.95 min, (ES+) (M + H)+ 407 |
| 1.9 | 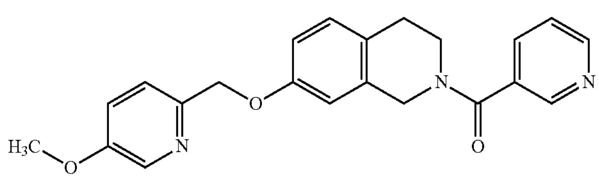 [SMILES: COc1ccc(COc2ccc3c(c2)CN(C(=O)c2cccnc2)CC3)nc1] | 375.43 | Tr (METCR1603 High pH 7 min) = 3.77 min, (ES+) (M + H)+ 376 |
| 1.10 | 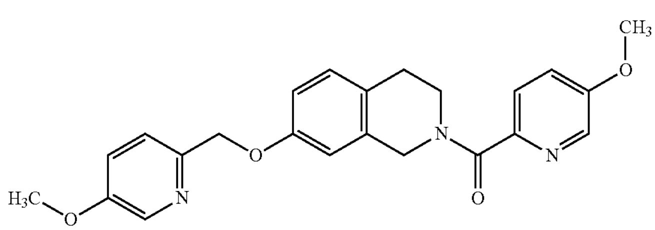 | 405.45 | Tr (MET-uHPLC-AB-101) = 2.79 min, (ES+) (M + H)+ 406 |

-continued

| Example | Structure | Mol. Weight | LCMS data |
|---|---|---|---|
| 1.11 | 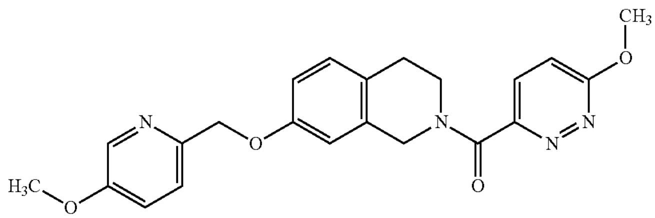 | 406.44 | Tr (MET-uHPLC-AB-101) = 2.58 min, (ES⁺) (M + H)⁺ 407 |
| 1.12 | 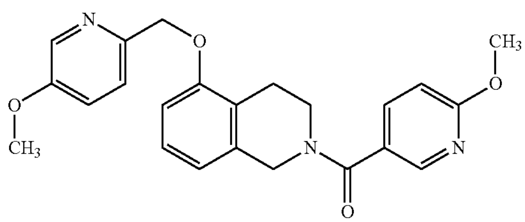 [SMILES: COc1ccc(COc2cccc3c2CCN(C(=O)c2ccc(OC)nc2)C3)nc1] | 405.45 | Tr (MET-uHPLC-AB-101) = 2.98 min, (ES⁺) (M + H)⁺ 406 |
| 1.13 | 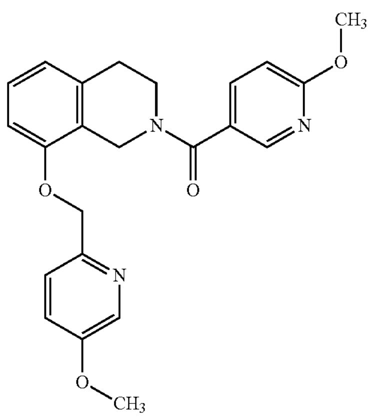 [SMILES: COc1ccc(COc2cccc3c2CN(C(=O)c2ccc(OC)nc2)CC3)nc1] | 405.45 | Tr (MET-uHPLC-AB-101) = 2.96 min, (ES⁺) (M + H)⁺ 406 |
| 1.14 | 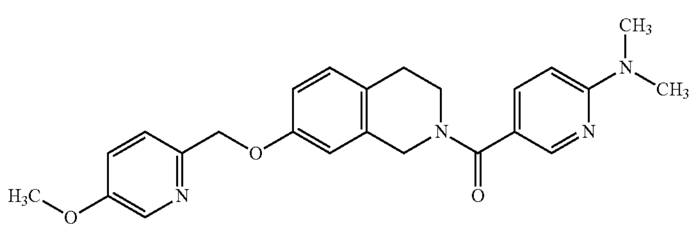 | 418.50 | Tr (MET-uHPLC-AB-101) = 1.98 min, (ES⁺) (M + H)⁺ 419 |
| 1.15 | 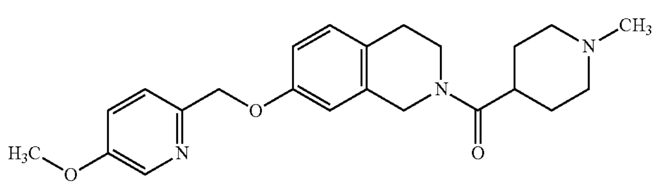 | 395.50 | Tr (MET-uHPLC-AB-101) = 1.64 min, (ES⁺) (M + H)⁺ 396 |
| 1.16 | 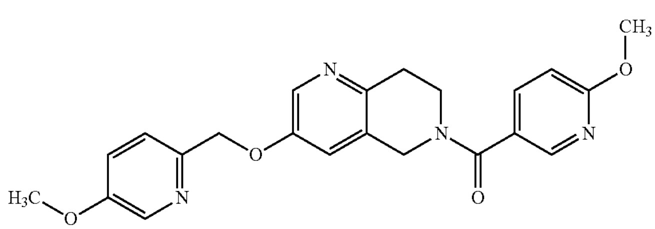 | 406.44 | Tr (MET-uHPLC-AB-101) = 1.85 min, (ES⁺) (M + H)⁺ 407 |

-continued

| Example | Structure | Mol. Weight | LCMS data |
|---|---|---|---|
| 1.17 | 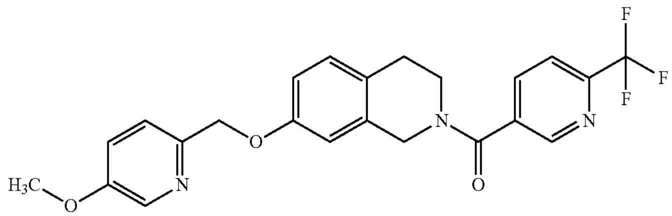 [SMILES: COc1ccc(COc2ccc3c(c2)CN(C(=O)c2ccc(C(F)(F)F)nc2)CC3)nc1] | 443.43 | Tr (MET-uHPLC-AB-101) = 3.16 min, (ES+) (M + H)+ 444 |
| 1.18 | 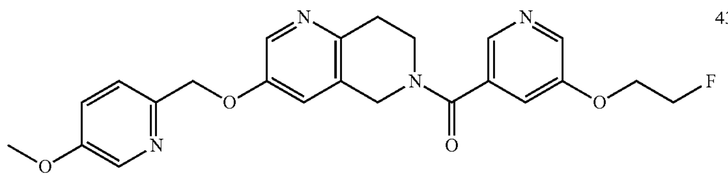 | 438.459 | Tr(METCR1603 High pH 7 min) = 3.36 min, (ES+) (M + H)+ 439.3 |
| 1.19 | 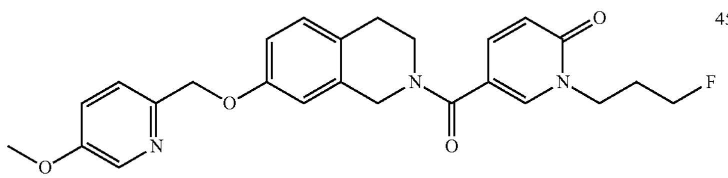 | 451.50 | Tr(METCR1603 High pH 7 min) = 3.68 min, (ES+) (M + H)+ 452.1 |
| 1.20 | 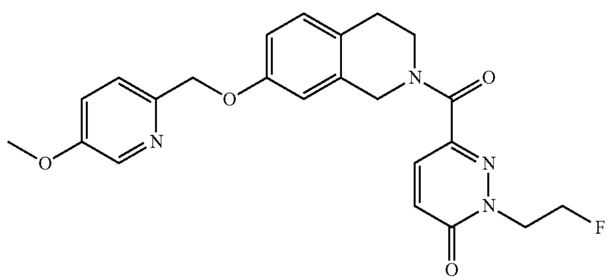 [SMILES: COc1ccc(COc2ccc3c(c2)CN(C(=O)c2ccc(=O)n(CCF)n2)CC3)nc1] | 438.459 | Tr(METCR1603 High pH 7 min) = 3.8 min, (ES+) (M + H)+ 439.1 |
| 1.21 | 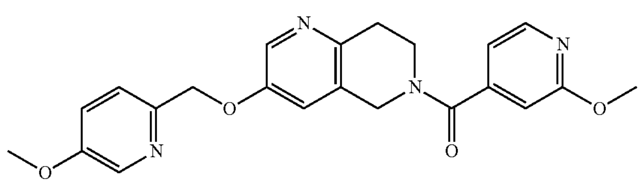 | 406.442 | Tr(METCR1603 High pH 7 min) = 3.44 min, (ES+) (M + H)+ 407.1 |
| 1.22 | 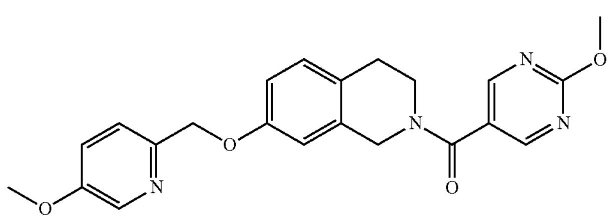 | 406.442 | Tr(MET-uHPLC-AB-101) = 2.61 min, (ES+) (M + H)+ 407 |
| 1.23 | 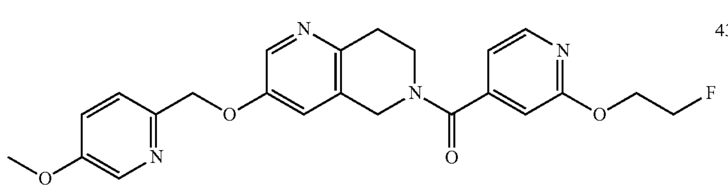 | 438.459 | Tr(METCR1603 High pH 7 min) = 3.44 min, (ES+) (M + H)+ 439.2 |

-continued

| Example | Structure | Mol. Weight | LCMS data |
|---|---|---|---|
| 1.24 | 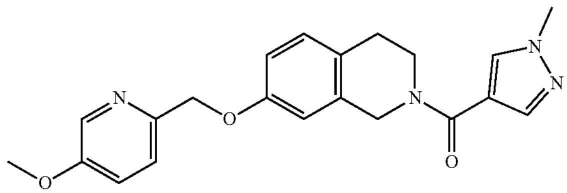 [SMILES: COc1ccc(COc2ccc3c(c2)CN(C(=O)c2cnn(C)c2)CC3)nc1] | 378.432 | Tr(METCR1603 High pH 7 min) = 3.56 min, (ES+) (M + H)+ 379 |
| 1.25 | 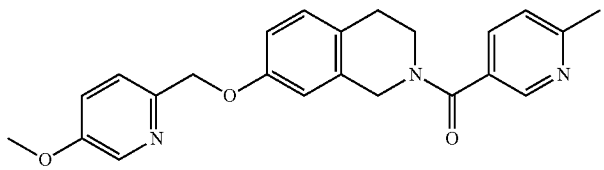 | 389.455 | Tr(MET-uHPLC-AB-101) = 2.19 min, (ES+) (M + H)+ 390 |
| 1.26 | 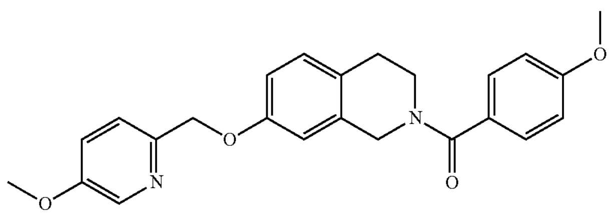 | 404.466 | Tr(MET-uHPLC-AB-101) = 3.06 min, (ES+) (M + H)+ 405 |
| 1.27 | 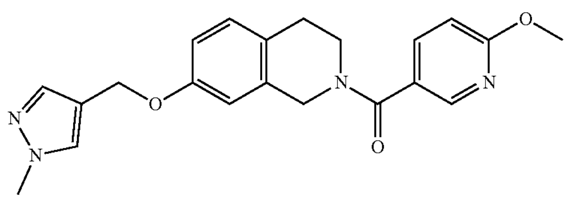 [SMILES: COc1ccc(C(=O)N2CCc3ccc(OCc4cnn(C)c4)cc3C2)cn1] | 378.432 | Tr(METCR1603 High pH 7 min) = 3.72 min, (ES+) (M + H)+ 379 |
| 1.28 | 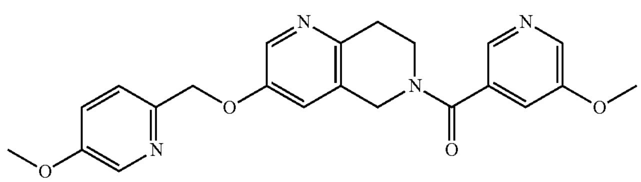 | 406.442 | Tr(METCR1603 High pH 7 min) = 3.28 min, (ES+) (M + H)+ 407.1 |
| 1.29 | 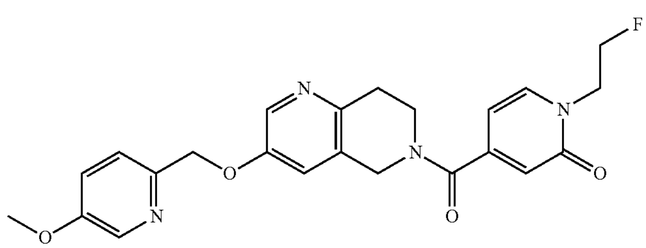 [SMILES: COc1ccc(COc2cnc3c(c2)CN(C(=O)c2ccn(CCF)c(=O)c2)CC3)nc1] | 438.459 | Tr(METCR1603 High pH 7 min) = 3.1 min, (ES+) (M + H)+ 439.1 |
| 1.30 | 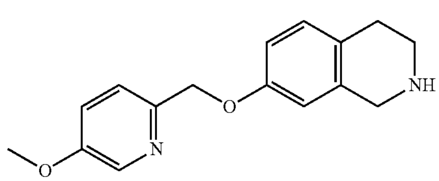 [SMILES: COc1ccc(COc2ccc3c(c2)CNCC3)nc1] | 270.332 | Tr(METCR1603 High pH 7 min) = 3.92 min, (ES+) (M + H)+ 271.2 |

Method 2
Scheme for Method 2

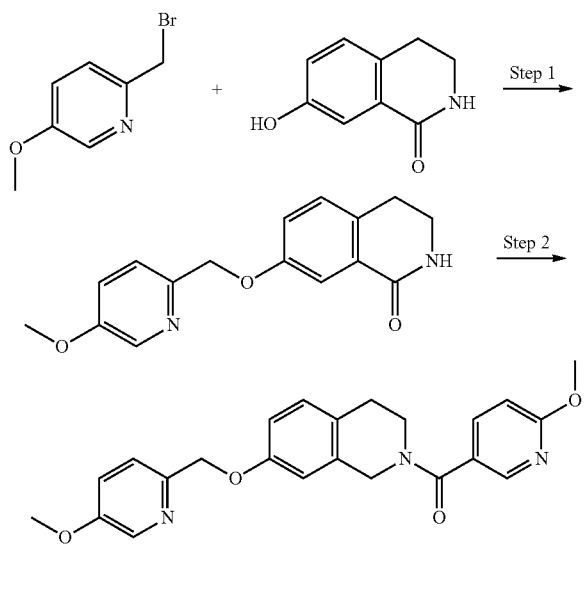

Example 2: 7-[(5-Methoxypyridin-2-yl)methoxy]-2-[(6-methoxypyridin-3-yl)methyl]-1,2,3,4-tetrahydroisoquinolin-1-one 7-[(5-Methoxypyridin-2-yl)methoxy]-1,2,3,4-tetrahydroisoquinolin-1-one A solution of 7-hydroxy-3,4-dihydroisoquinolin-1(2H)-one (150 mg, 0.92 mmol), 2-(bromomethyl)-5-methoxypyridine (204 mg, 1.01 mmol) and potassium carbonate (140 mg, 1.01 mmol) in acetone (15 mL) was heated at 55° C. for 2.5 hours. Further 2-(bromomethyl)-5-methoxypyridine (102 mg, 0.5 mmol) and potassium carbonate (140 mg, 1.01 mmol) were added and the reaction was stirred at 55° C. overnight. After 20 hours further 2-(bromomethyl)-5-methoxypyridine (279 mg, 1.38 mmol) and potassium carbonate (140 mg, 1.01 mmol) were added and the reaction was stirred at 55° C. overnight. The reaction mixture was cooled and diluted with EtOAc (50 mL). The mixture was washed with water (2×10 mL), dried (Na$_2$SO$_4$), filtered and concentrated in vacuo. The crude residue was purified twice by column chromatography (silica, eluting with 0-20% MeOH in DCM) to give the title compound. $^1$H NMR (500 MHz, DMSO-d$_6$) δ 8.31-8.26 (m, 1H), 7.93 (s, 1H), 7.46-7.40 (m, 3H), 7.22 (d, J=8.3 Hz, 1H), 7.12 (dd, J=8.3, 2.8 Hz, 1H), 5.12 (s, 2H), 3.94-3.65 (m, 5H), 2.81 (t, J=6.6 Hz, 2H). Tr (METCR1410)=0.89 min, (ES$^+$) (M+H)$^+$ 285, 92%.

7-[(5-Methoxypyridin-2-yl)methoxy]-2-[(6-methoxypyridin-3-yl)methyl]-1,2,3,4-tetrahydroisoquinolin-1-one A solution of 7-[(5-methoxypyridin-2-yl)methoxy]-1,2,3,4-tetrahydroisoquinolin-1-one (119 mg, 0.39 mmol) and NaH (60% in oil, 18 mg, 0.46 mmol) in THF (10 mL) was heated to 70° C. for 0.5 hours. The reaction mixture was then cooled to rt and 5-(chloromethyl)-2-methoxypyridine (73 mg, 0.46 mmol) added in THF and DMF (2:1, 3 mL). The reaction mixture was stirred at rt overnight. EtOAc (50 mL) was added and the mixture was washed with water (2×10 mL). The combined organics were dried (Na$_2$SO$_4$), filtered and concentrated in vacuo. The crude residue was purified by prep HPLC (high pH) to give the title compound.
$^1$H NMR (500 MHz, Chloroform-d) δ 8.31 (d, J=2.8 Hz, 1H), 8.11 (d, J=2.0 Hz, 1H), 7.77-7.74 (m, 1H), 7.62 (dd, J=8.5, 2.5 Hz, 1H), 7.50-7.44 (m, 1H), 7.31-7.27 (m, 1H), 7.11-7.05 (m, 2H), 6.72 (d, J=8.5 Hz, 1H), 5.22 (s, 2H), 4.70 (s, 2H), 3.93 (s, 3H), 3.88 (s, 3H), 3.46 (t, J=6.7 Hz, 2H), 2.86 (t, J=6.7 Hz, 2H). Tr (MET-uHPLC-AB-101)=2.80 min, (ES$^+$) (M+H)$^+$ 406.

Method 3
Scheme for Method 3

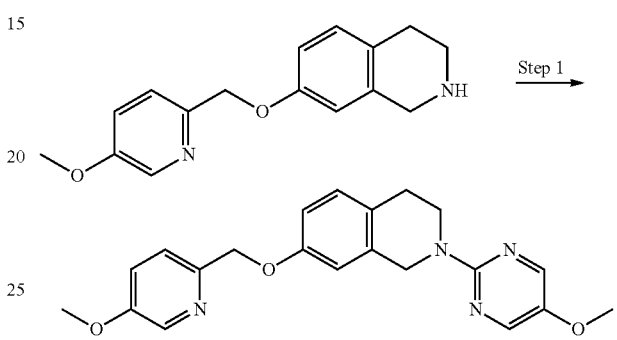

Example 3: 7-[(5-Methoxypyridin-2-yl)methoxy]-2-(5-methoxypyrimidin-2-yl)-1,2,3,4-tetrahydroisoquinoline To a microwave vial was added 7-[(5-methoxy-2-pyridyl)methoxy]-1,2,3,4-tetrahydroisoquinoline hydrochloride (50 mg, 0.16 mmol, prepared as described in method 1), DIPEA (80 μL, 0.49 mmol) and 2-chloro-5-methoxy-pyrimidine (28 mg, 0.20 mmol). The vessel was sealed and irradiated at 140° C. for 4 hours. The reaction was repeated on 125 mg scale and the two were combined and concentrated in vacuo. The crude residue was purified by column chromatography (silica, eluting with 20-100% EtOAc in heptane) and then by prep HPLC (low pH) to give the title compound.
$^1$H NMR (500 MHz, DMSO-d$_6$) δ 8.28 (d, J=2.4 Hz, 1H), 8.25-8.21 (m, 2H), 7.46 (d, J=8.5 Hz, 1H), 7.41 (dd, J=8.6, 2.9 Hz, 1H), 7.06 (d, J=8.4 Hz, 1H), 6.90 (d, J=2.6 Hz, 1H), 6.81 (dd, J=8.3, 2.7 Hz, 1H), 5.07 (s, 2H), 4.74 (s, 2H), 3.89 (t, J=5.9 Hz, 2H), 3.83 (s, 3H), 3.77 (s, 3H), 2.76 (t, J=5.8 Hz, 2H). Tr (MET-uHPLC-AB-101)=3.37 min, (ES$^+$) (M+H)$^+$ 379.

Method 4
Scheme for Method 4

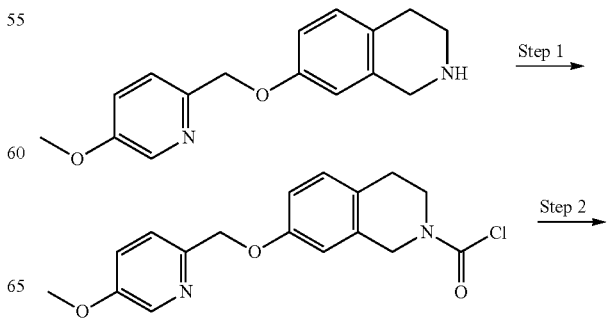

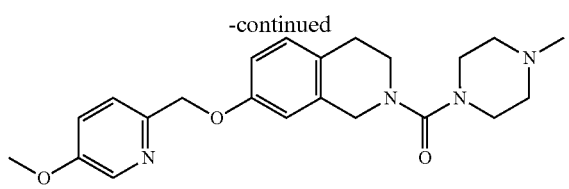

Example 4: 7-[(5-Methoxypyridin-2-yl)methoxy]-2-(4-methylpiperazine-1-carbonyl)-1,2,3,4-tetrahydroisoquinoline 7-[(5-Methoxy-2-pyridyl)methoxy]-3,4-dihydro-1H-isoquinoline-2-carbonyl chloride hydrochloride Triphosgene (0.11 g, 0.36 mmol) was dissolved in DCM (5 mL) and the reaction cooled to −78° C., pyridine (80 µL, 1.03 mmol) was added followed by 7-[(5-methoxypyridin-2-yl)methoxy]-1,2,3,4-tetrahydroisoquinoline (278 mg, 1.03 mmol, prepared by method 1) dissolved in DCM (3 mL). The reaction mixture was warmed to rt and stirred for 1.5 hours. The reaction mixture was diluted with DCM and 2 M HCl was added, the layers were separated and the aqueous layer was extracted with DCM (2×20 mL). The organic layers were combined and washed with NaHCO$_3$. The organic layer was concentrated under reduced pressure and the residue purified by column chromatography (silica, eluting with 0-50% EtOAc in heptane) to give the title compound. $^1$H (250 MHz, DMSO-d$_6$) δ 9.06 (s, 1H), 8.27 (d, J=1.8 Hz, 1H), 7.57-7.30 (m, 2H), 7.14 (d, J=8.4 Hz, 1H), 7.04-6.83 (m, 2H), 5.10 (s, 2H), 4.21 (s, 2H), 3.85 (s, 3H), 3.35 (t, J=6.3 Hz, 2H), 2.95 (t, J=6.4 Hz, 2H). Tr (METCR1410)=1.12 min, (ES$^+$) (M+H)$^+$ 333, 93%.

7-[(5-Methoxypyridin-2-yl)methoxy]-2-(4-methylpiperazine-1-carbonyl)-1,2,3,4-tetrahydroisoquinoline 1-Methylpiperazine (15 mg, 0.15 mmol) was dissolved in DCM (2 mL) and NaH (60%, 12 mg, 0.3 mmol) was added. 7-[(5-Methoxy-2-pyridyl)methoxy]-3,4-dihydro-1H-isoquinoline-2-carbonyl chloride hydrochloride (50 mg, 0.15 mmol) was dissolved in DCM (2 mL) and added to the reaction mixture. The reaction mixture was stirred at rt for 2 hours. The reaction mixture was diluted with DCM (20 mL) and quenched with water. The two layers were separated and the aqueous layer was extracted with DCM (2×25 mL). The combined organics were concentrated under reduced pressure. The residue was washed with 2:1 diethyl ether:heptane to give the title compound.

$^1$H NMR (500 MHz, DMSO-d$_6$) δ 8.27 (d, J=2.2 Hz, 1H), 7.44 (d, J=8.3 Hz, 1H), 7.41 (dd, J=8.6, 2.8 Hz, 1H), 7.03 (d, J=8.3 Hz, 1H), 6.90-6.72 (m, 2H), 5.06 (s, 2H), 4.30 (s, 2H), 3.83 (s, 3H), 3.38 (t, J=5.9 Hz, 2H), 3.22-3.12 (m, 4H), 2.73 (t, J=5.7 Hz, 2H), 2.33-2.27 (m, 4H), 2.18 (s, 3H). Tr (MET-uHPLC-AB-101)=1.66 min, (ES$^+$) (M+H)$^+$ 397.

Also prepared by this method:

| Example | Structure | Mol. Weight | LCMS data |
|---|---|---|---|
| 4.1 | 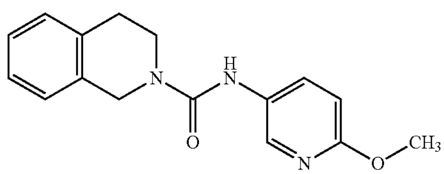 [SMILES: COc1ccc(NC(=O)N2CCc3ccccc3C2)cn1] | 283.33 | Tr (METCR1603 High pH 7 min) = 3.94 min, (ES+) (M + H)+ 284 |
| 4.2 | 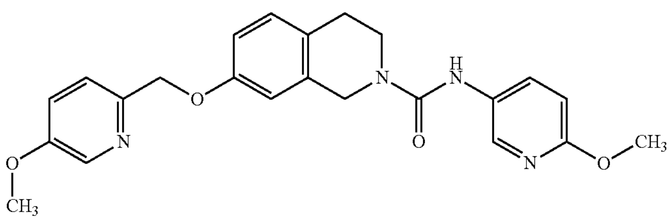 [SMILES: COc1ccc(COc2ccc3c(c2)CN(C(=O)Nc2ccc(OC)nc2)CC3)nc1] | 420.47 | Tr (MET-uHPLC-AB-101) = 2.71 min, (ES+) (M + H)+ 421 |
| 4.3 | 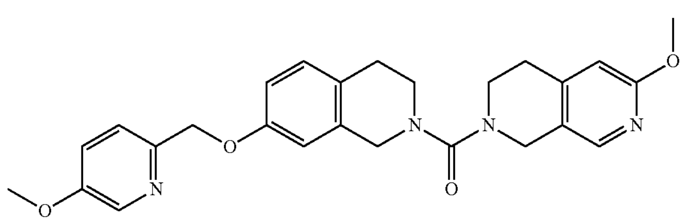 | 460.534 | Tr(MET-uHPLC-AB-101) = 3.06 min, (ES+) (M + H)+ 461 |
| 4.4 | 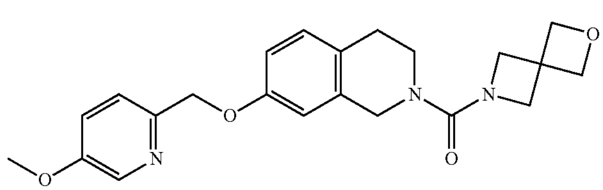 [SMILES: COc1ccc(COc2ccc3c(c2)CN(C(=O)N2CC4(COC4)C2)CC3)nc1] | 395.459 | Tr(MET-uHPLC-AB-101) = 2.42 min, (ES+) (M + H)+ 396 |

Method 5
Scheme for Method 5

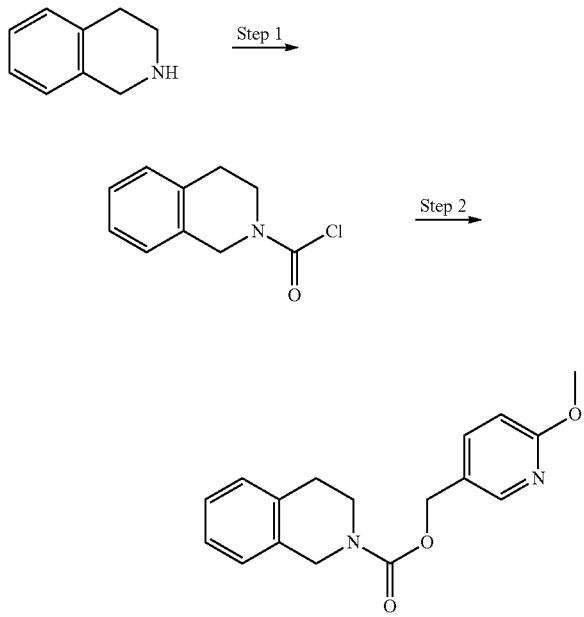

Example 5: (6-Methoxypyridin-3-yl)methyl 1,2,3,4-tetrahydroisoquinoline-2-carboxylate 3,4-dihydro-1H-isoquinoline-2-carbonyl chloride Triphosgene (780 mg, 2.63 mmol) was dissolved in DCM (15 mL) and cooled to −78° C. and pyridine (0.6 mL, 7.51 mmol) was added followed by 1,2,3,4-tetrahydroisoquinoline (940 μL, 7.51 mmol). The reaction mixture was warmed to rt and stirred for 1.5 hours. 2 M HCl (10 mL) was added and the product was extracted with DCM (3×25 mL). The organic layers were combined and washed with saturated NaHCO$_3$. The organic layer was concentrated under reduced pressure and the residue purified by column chromatography (silica, eluting with 0-10% EtOAc in heptane) gave the title compound. $^1$H NMR (500 MHz, Chloroform-d$_6$) δ 7.24-7.10 (m, 4H), 4.84 (s, 1H), 4.75 (s, 1H), 3.92 (t, J=6.0 Hz, 1H), 3.85 (t, J=6.0 Hz, 1H), 3.03-2.87 (m, 2H). Tr (METCR1410) =1.13 min, (ES$^+$) (M+H)$^+$ 196.

(6-Methoxypyridin-3-yl)methyl 1,2,3,4-tetrahydroisoquinoline-2-carboxylate (6-Methoxy-3-pyridyl)methanol (142 mg, 1.02 mmol) was dissolved in DCM (2 mL) and NaH (60%, 41 mg, 1.02 mmol) was added. 3,4-Dihydro-1H-isoquinoline-2-carbonyl chloride (100 mg, 0.51 mmol) was dissolved in DCM (2 mL) and added to the reaction mixture. The reaction mixture was stirred at rt for 2.5 hours. The reaction mixture was diluted with DCM and quenched with water. The two layers were separated and the aqueous layer extracted with DCM (2×25 mL). The combined organics were concentrated under reduced pressure and the residue was purified by acidic preparative HPLC. Further purification by column chromatography (silica, eluting with 0-50% EtOAc in heptane) gave the title compound.

$^1$H NMR (500 MHz, DMSO-d$_6$) δ 8.21 (d, J=2.1 Hz, 1H), 7.75 (dd, J=8.5, 2.4 Hz, 1H), 7.25-7.11 (m, 4H), 6.83 (d, J=8.5 Hz, 1H), 5.06 (s, 2H), 4.54 (s, 2H), 3.84 (s, 3H), 3.60 (t, J=6.0 Hz, 2H), 2.78 (t, J=5.7 Hz, 2H). Tr (MET-uHPLC-AB-101)=3.45 min, (ES$^+$) (M+H)$^+$ 299.

Also prepared by this method:

| Example | Structure | Mol. Weight | LCMS data |
|---|---|---|---|
| 5.1 | 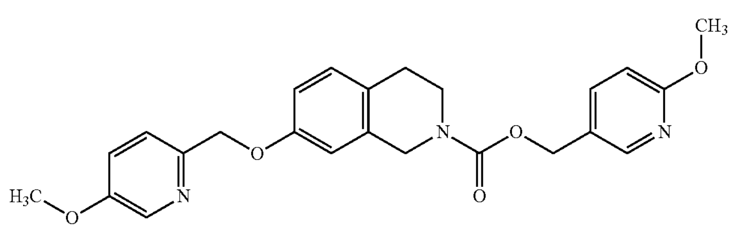 | 435.48 | Tr (MET-uHPLC-AB-101) = 3.38 min, (ES$^+$) (M + H)$^+$ 436 |

Method 6
Scheme for Method 6

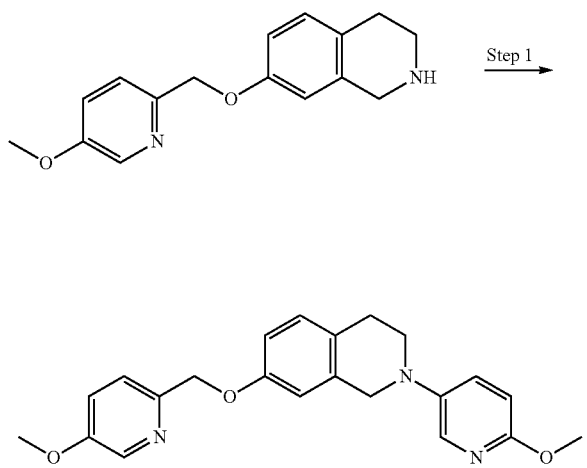

Example 6: (7-[(5-Methoxypyridin-2-yl)methoxy]-2-(6-methoxypyridin-3-yl)-1,2,3,4-tetrahydroisoquinoline To an oven-dried pressure tube equipped with a septum was added $Pd_2(dba)_3$ (30 mg, 0.03 mmol), RuPhos (30 mg, 0.07 mmol), caesium carbonate (372 mg, 1.14 mmol), 7-[(5-methoxy-2-pyridyl)methoxy]-1,2,3,4-tetrahydroisoquinoline hydrochloride (100 mg, 0.33 mmol, prepared as described in Method 1) and 5-bromo-2-methoxypyridine (67 mg, 0.36 mmol). The vessel was sealed and flushed with nitrogen and toluene was added (7.5 mL). The reaction mixture was de-gassed with nitrogen and then heated at 85° C. overnight. The reaction mixture was cooled and filtered and concentrated in vacuo. The crude residue was purified by column chromatography (silica, eluting with 0-100% EtOAc in heptane) to give the title compound.

$^1$H NMR (500 MHz, DMSO-$d_6$) δ 8.30-8.25 (m, 1H), 7.84 (d, J=2.9 Hz, 1H), 7.51 (dd, J=9.0, 3.1 Hz, 1H), 7.45 (d, J=8.4 Hz, 1H), 7.42 (dd, J=8.6, 2.9 Hz, 1H), 7.05 (d, J=8.4 Hz, 1H), 6.86 (d, J=2.5 Hz, 1H), 6.82 (dd, J=8.3, 2.7 Hz, 1H), 6.73 (d, J=9.0 Hz, 1H), 5.07 (s, 2H), 4.25 (s, 2H), 3.83 (s, 3H), 3.77 (s, 3H), 3.42 (t, J=5.9 Hz, 2H), 2.80 (t, J=5.8 Hz, 2H). Tr (MET-uHPLC-AB-101)=3.15 min, (ES$^+$) (M+H)$^+$ 378.

Also prepared by this method:

| Example | Structure | Mol. Weight | LCMS data |
|---|---|---|---|
| 6.1 | 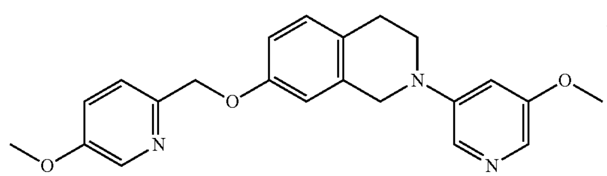 | 377.444 | Tr(MET-uHPLC-AB-101) = 2.1 min, (ES+) (M + H)+ 378 |
| 6.2 | 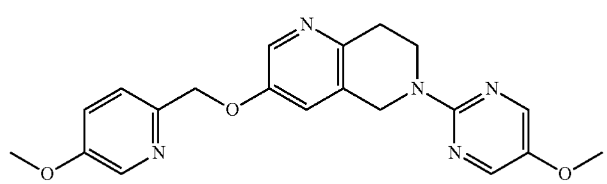 | 379.42 | Tr(METCR1603 High pH 7 min) = 3.84 min, (ES+) (M + H)+ 380 |
| 6.3 | 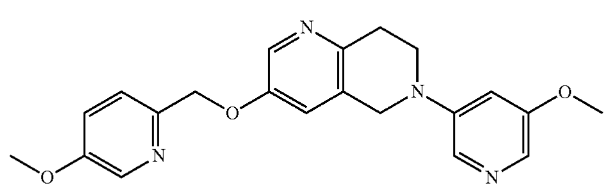 | 378.432 | Tr(MET-uHPLC-AB-101) = 1.29 min, (ES+) (M + H)+ 379 |

Method 7

Scheme for Method 7

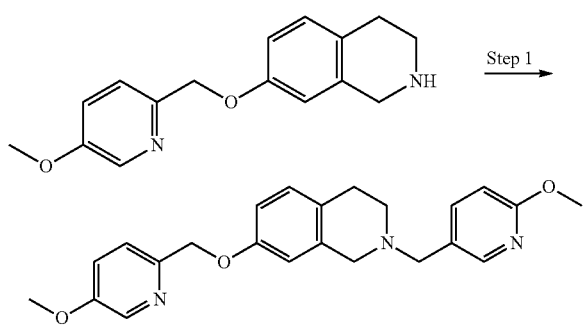

Example 7: (7-[(5-Methoxypyridin-2-yl)methoxy]-2-[(6-methoxypyridin-3-yl)methyl]-1,2,3,4-tetrahydroisoquinoline 7-[(5-Methoxy-2-pyridyl)methoxy]-1,2,3,4-tetrahydroisoquinoline hydrochloride (175 mg, 0.57 mmol, as prepared by Method 450) and caesium carbonate (372 mg, 1.14 mmol) were stirred in DMF (10 mL) until a full solution was obtained. Potassium iodide (95 mg, 0.57 mmol) and 5-(chloromethyl)-2-methoxy-pyridine (126 mg, 0.8 mmol) were added as a solution in DMF (5 mL) and the reaction mixture was stirred at rt for 17 hours. The reaction mixture was concentrated in vacuo and then suspended in DCM. The insoluble inorganic material was removed by vacuum filtration and the filtrate was concentrated in vacuo. The crude residue was purified by column chromatography (silica, eluting with 0-100% EtOAc in heptane) to give the title compound.

$^1$H NMR (500 MHz, DMSO-$d_6$) δ 8.26 (dd, J=2.6, 0.9 Hz, 1H), 8.09 (d, J=2.1 Hz, 1H), 7.67 (dd, J=8.5, 2.4 Hz, 1H), 7.44-7.37 (m, 2H), 6.99 (d, J=8.4 Hz, 1H), 6.80 (d, J=8.4 Hz, 1H), 6.76 (dd, J=8.4, 2.7 Hz, 1H), 6.68 (d, J=2.6 Hz, 1H), 5.02 (s, 2H), 3.84 (s, 3H), 3.82 (s, 3H), 3.56 (s, 2H), 3.47 (s, 2H), 2.70 (t, J=5.6 Hz, 2H), 2.63 (t, J=5.9 Hz, 2H). Tr (MET-uHPLC-AB-101)=1.70 min, (ES$^+$) (M+H)$^+$ 392.

Method 8

Scheme for Method 8

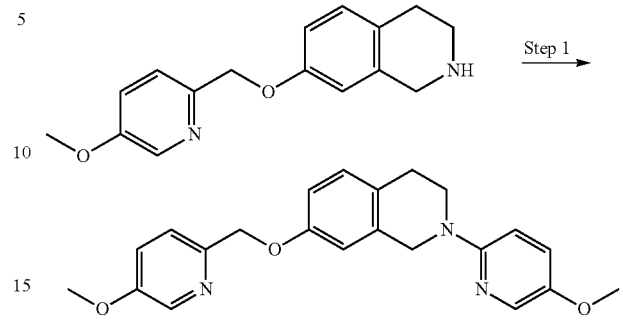

Example 8: 2-(5-Methoxypyridin-2-yl)-7-[(5-methoxypyridin-2-yl)methoxy]-1,2,3,4-tetrahydroisoquinoline To a microwave vial was added 7-[(5-methoxy-2-pyridyl)methoxy]-1,2,3,4-tetrahydroisoquinoline hydrochloride (100 mg, 0.33 mmol, prepared by method 1), 2-bromo-5-methoxypyridine (118 mg, 0.63 mmol), potassium t-butoxide (91 mg, 0.81 mmol), CyJohnPhos (7 mg, 0.02 mmol), Pd(Oac)$_2$ (4 mg, 0.02 mmol) and t-butanol (2 mL). The vial was sealed and de-gassed with nitrogen and irradiated at 100° C. for 0.5 hours. The reaction was then irradiated at 100° C. for a further 1 hour. The reaction was repeated on a 75 mg scale and the two were combined for purification. The reaction mixtures were diluted with EtOAc (10 mL) and filtered through Celite. The resulting filtrate was washed with saturated NaCl solution, dried over MgSO$_4$ and concentrated under reduced pressure to yield the crude product. The crude residue was purified by column chromatography (silica, eluting with 0-100% EtOAc in heptane) to give the title compound.

$^1$H NMR (500 MHz, DMSO-$d_6$) δ 8.28 (d, J=2.8 Hz, 1H), 7.89 (d, J=3.1 Hz, 1H), 7.45 (d, J=8.5 Hz, 1H), 7.41 (dd, J=8.6, 2.9 Hz, 1H), 7.28 (dd, J=9.1, 3.1 Hz, 1H), 7.05 (d, J=8.4 Hz, 1H), 6.91-6.83 (m, 2H), 6.80 (dd, J=8.4, 2.6 Hz, 1H), 5.07 (s, 2H), 4.53 (s, 2H), 3.83 (s, 3H), 3.72 (s, 3H), 3.69 (t, J=5.9 Hz, 2H), 2.77 (t, J=5.9 Hz, 2H). Tr (MET-uHPLC-AB-101)=2.14 min, (ES$^+$) (M+H)$^+$ 378.

Also prepared by this method:

| Example | Structure | Mol. Weight | LCMS data |
|---|---|---|---|
| 8.1 | 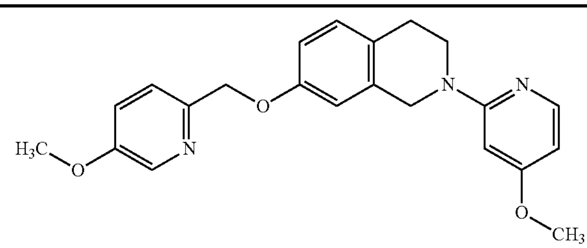 | 377.44 | Tr (MET-uHPLC-AB-101) = 1.76 min, (ES$^+$) (M + H)$^+$ 378, 92% |
| 8.2 | 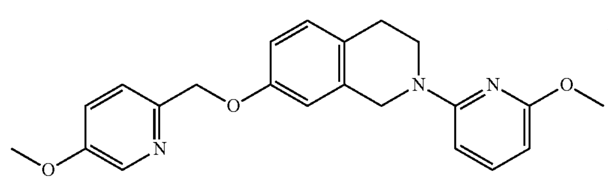 | 377.444 | Tr(MET-uHPLC-AB-101) = 3.98 min, (ES$^+$) (M + H)$^+$ 378 |

Method 9

Scheme for Method 9

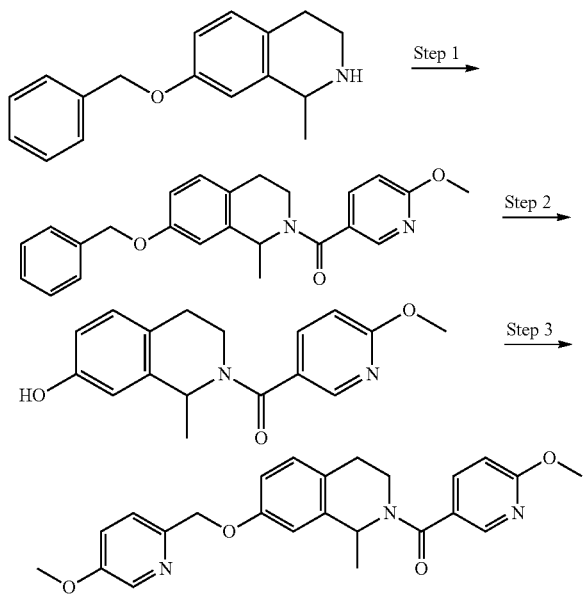

Example 9: 7-[(5-Methoxypyridin-2-yl)methoxy]-2-(6-methoxypyridine-3-carbonyl)-1-methyl-1,2,3,4-tetrahydroisoquinoline 7-(Benzyloxy)-2-(6-methoxypyridine-3-carbonyl)-1-methyl-1,2,3,4-tetrahydroisoquinoline 7-(Benzyloxy)-1-methyl-1,2,3,4-tetrahydroisoquinoline (400 mg, 1.58 mmol), 6-methoxypyridine-3-carboxylic acid (242 mg, 1.58 mmol) and 1-[bis(dimethylamino)methylene]-1H-1,2,3-triazolo[4,5-b]pyridinium 3-oxide hexafluorophosphate (600 mg, 1.58 mmol) were dissolved in DMF (8 mL) and DIPEA (825 µL, 4.74 mmol) was added. The reaction was stirred under a nitrogen atmosphere at rt for 2 hours. The reaction mixture was poured onto water, diluted with DCM, the aqueous layer extracted into DCM (3×20 mL) and the combined organic layers dried and concentrated in vacuo to give the title compound, which was used in the next step with no further purification. Tr (METCR1673) =1.25 min, (ES+) (M+H)+ 389, 87%.

2-(6-Methoxypyridine-3-carbonyl)-1-methyl-1,2,3,4-tetrahydroisoquinolin-7-ol 7-(Benzyloxy)-2-(6-methoxypyridine-3-carbonyl)-1-methyl-1,2,3,4-tetrahydroisoquinoline (87%, 870 mg, 1.95 mmol) was dissolved in 1:1 EtOH:THF (20 mL) and placed under a nitrogen atmosphere. Palladium (10% on carbon) (87 mg, 0.82 mmol) was added and the reaction placed under a hydrogen atmosphere and stirred at rt for 16 hours. The hydrogen was evacuated from the flask and the reaction mixture filtered through a pad of celite, and washed with MeOH (30 mL). The filtrate was concentrated and purified by column chromatography (silica, eluting 0-100% EtOAc in heptane) to give the title compound. Tr (METCR1673)= 0.96 min, (ES+) (M+H)+ 299, 90%.

7-[(5-Methoxypyridin-2-yl)methoxy]-2-(6-methoxypyridine-3-carbonyl)-1-methyl-1,2,3,4-tetrahydroisoquinoline 2-(6-Methoxypyridine-3-carbonyl)-1-methyl-1,2,3,4-tetrahydroisoquinolin-7-ol (90% 229 mg, 0.77 mmol) and (5-methoxypyridin-2-yl)methanol (120 mg, 0.84 mmol) were suspended in toluene (7 mL) and CMBP (0.24 mL, 0.92 mmol) added. The reaction was heated to 100° C. in a sealed tube for 4 hours. The reaction mixture was cooled, diluted with DCM, washed with water, dried (MgSO$_4$) and concentrated to dryness. The oily residue was dissolved in EtOAc and heptane added dropwise to induce precipitation. The mixture was concentrated to dryness, suspended in 1:1 EtOAc:heptane, filtered, and the solid washed with EtOAc and dried under vacuum to give the title compound.
$^1$H NMR (250 MHz, 353 K, DMSO-d$_6$) δ 8.35-8.14 (m, 2H), 7.75 (dd, J=8.5, 2.4 Hz, 1H), 7.52-7.30 (m, 2H), 7.06 (d, J=8.2 Hz, 1H), 6.93-6.79 (m, 3H), 5.31 (s, 1H), 5.08 (s, 2H), 4.00 (s, 1H), 3.93 (s, 3H), 3.85 (s, 3H), 3.50-3.29 (m, 1H), 2.95-2.80 (m, 1H), 2.76-2.64 (m, 1H), 1.49 (d, J=6.7 Hz, 3H). Tr (MET-uHPLC-AB-101)=3.15 min, (ES+) (M+H)+ 420.

Method 10

Scheme for Method 10

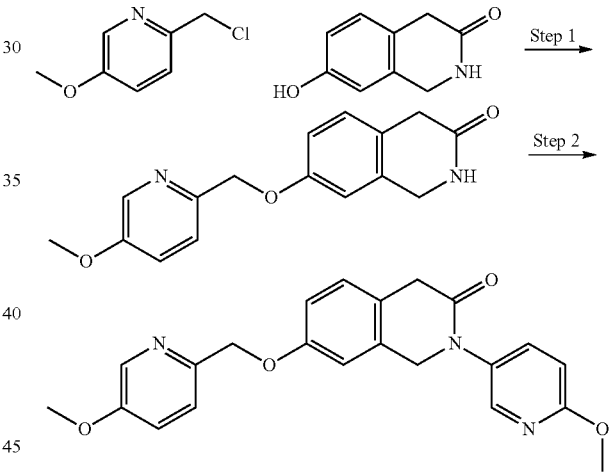

Example 10: 7-[(5-Methoxypyridin-2-yl)methoxy]-2-(6-methoxypyridin-3-yl)-1,2,3,4-tetrahydroisoquinolin-3-one 7-[(5-Methoxy-2-pyridyl)methoxy]-2,4-dihydro-1H-isoquinolin-3-one 7-Hydroxy-2,4-dihydro-1H-isoquinolin-3-one (250 mg, 1.53 mmol), 2.2 M KI (696 µL) and Cs$_2$CO$_3$ (998 mg, 3.06 mmol) were dissolved in DMF (5 mL) and a solution of 2-(chloromethyl)-5-methoxy-pyridine (241 mg, 1.53 mmol) in DMF (5 mL) was added. The reaction mixture was stirred at rt overnight. The reaction mixture was concentrated in vacuo and the residue was triturated with water and further purified by column chromatography (silica, eluting with 0-80% EtOAc in heptanes) to give the title compound. $^1$H NMR (500 MHz, DMSO-d$_6$) δ 8.28 (d, J=2.7 Hz, 1H), 7.94 (s, 1H), 7.66-7.25 (m, 2H), 7.10 (d, J=8.4 Hz, 1H), 6.97 (d, J=2.5 Hz, 1H), 6.89 (dd, J=8.3, 2.6 Hz, 1H), 5.08 (s, 2H), 4.29 (s, 2H), 3.84 (s, 3H), 3.35 (s, 2H). Tr (METCR1410)= 0.86 min, (ES⁺) (M+H)⁺ 285.

7-[(5-Methoxypyridin-2-yl)methoxy]-2-(6-methoxypyridin-3-yl)-1,2,3,4-tetrahydroisoquinolin-3-one A suspension of (1R,2R)—N,N'-dimethylcyclohexane-1,2-diamine (23 mg, 0.16 mmol), copper (I) iodide (10 mg, 0.05 mmol) and potassium phosphate (280 mg, 1.32 mmol) in dioxane (6 mL) in a pressure tube was de-gassed for 50 minutes. 7-[(5-Methoxy-2-pyridyl)methoxy]-2,4-dihydro-1H-isoquinolin-3-one (150 mg, 0.53 mmol) and 5-bromo-2-methoxypyridine (80 µL, 0.63 mmol) were then added and the reaction vessel was sealed and heated at 110° C. for 21.5 hours. The reaction mixture was cooled and EtOAc (20 mL) and water (10 mL) were added. The organic phase was extracted and the aqueous phase re-extracted with EtOAc (2×5 mL). The combined organics were washed with saturated brine solution, dried (Na₂SO₄), filtered and concentrated in vacuo. The crude residue was purified by column chromatography (silica, eluting with 0-100% EtOAc in heptane) to give the title compound.

¹H NMR (500 MHz, DMSO-d₆) 8.27 (d, J=2.8 Hz, 1H), 8.14 (d, J=2.7 Hz, 1H), 7.69 (dd, J=8.8, 2.7 Hz, 1H), 7.46 (d, J=8.6 Hz, 1H), 7.41 (dd, J=8.6, 2.9 Hz, 1H), 7.20 (d, J=8.4 Hz, 1H), 7.02 (d, J=2.4 Hz, 1H), 6.95 (dd, J=8.3, 2.6 Hz, 1H), 6.87 (d, J=8.8 Hz, 1H), 5.09 (s, 2H), 4.82 (s, 2H), 3.90-3.79 (m, 6H), 3.64 (s, 2H). Tr (MET-uHPLC-AB-101)= 2.5 min, (ES⁺) (M+H)⁺ 392.

Method 11

Scheme for Method 11

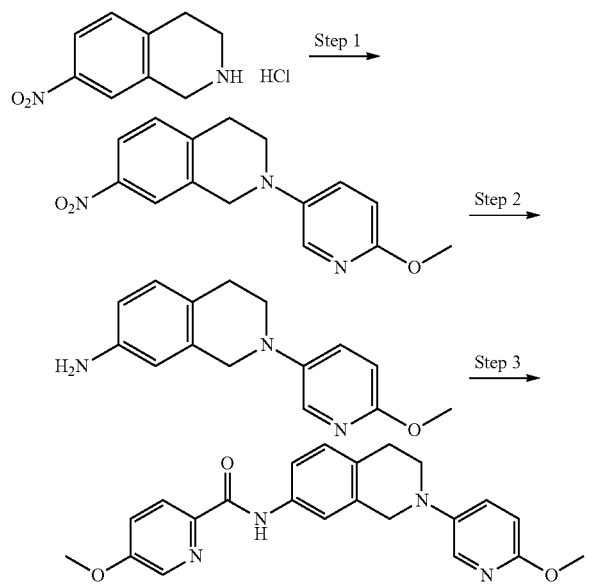

Example 11: 5-Methoxy-N-[2-(6-methoxypyridin-3-yl)-1,2,3,4-tetrahydroisoquinolin-7-yl]pyridine-2-carboxamide

2-(6-Methoxy-3-pyridyl)-7-nitro-3,4-dihydro-1H-isoquinoline

7-Nitro-1,2,3,4-tetrahydroisoquinoline hydrochloride (500 mg, 2.33 mmol), RuPhos Pd G3 (195 mg, 0.23 mmol), RuPhos (109 mg, 0.23 mmol), sodium 2-methylpropan-2-olate (784 mg, 8.15 mmol) and 5-bromo-2-methoxy-pyridine (657 mg, 3.49 mmol) were suspended in degassed THF (20 mL). The vial was sealed and the resulting mixture was heated at 85° C. for 17 hours. The reaction was cooled and diluted with EtOAc. The resulting solution was filtrated through a Celite pad and concentrated. Further purification by column chromatography (silica, 0-100% EtOAc in heptanes) gave the title compound. ¹H NMR (500 MHz, DMSO-d₆) δ 8.15 (d, J=2.3 Hz, 1H), 8.04 (dd, J=8.4, 2.4 Hz, 1H), 7.90 (d, J=3.0 Hz, 1H), 7.56 (dd, J=9.0, 3.1 Hz, 1H), 7.46 (d, J=8.5 Hz, 1H), 6.76 (d, J=9.0 Hz, 1H), 4.44 (s, 2H), 3.79 (s, 3H), 3.50 (t, J=5.9 Hz, 2H), 3.03 (t, J=5.8 Hz, 2H). Tr (METCR1410)=1.16 min, (ES⁺) (M+H)⁺ 286.

2-(6-Methoxy-3-pyridyl)-3,4-dihydro-1H-isoquinolin-7-amine

A solution of 2-(6-methoxy-3-pyridyl)-7-nitro-3,4-dihydro-1H-isoquinoline (100 mg, 0.35 mmol) in EtOH (5 mL). The mixture was degassed and purged with nitrogen three times. Pd/C (10%, 19 mg, 0.02 mmol) was added, and the reaction mixture was degassed and purged with nitrogen a further 3 times and then filled with hydrogen 3 times. The reaction was stirred for 16 hours overnight. The mixture was then filtered through celite, washed with MeOH and then concentrated in vacuo to give the title compound. ¹H NMR (500 MHz, DMSO-d₆) δ 7.84 (d, J=3.0 Hz, 1H), 7.50 (dd, J=9.0, 3.1 Hz, 1H), 6.79 (d, J=8.1 Hz, 1H), 6.72 (d, J=9.0 Hz, 1H), 6.52-6.31 (m, 2H), 4.85 (s, 2H), 4.14 (s, 2H), 3.78 (s, 3H), 3.38 (t, J=5.9 Hz, 2H), 2.71 (t, J=5.7 Hz, 2H). Tr (METCR1410)=0.79 min, (ES⁺) (M+H)⁺ 256, 84%.

5-Methoxy-N-[2-(6-methoxypyridin-3-yl)-1,2,3,4-tetrahydroisoquinolin-7-yl]pyridine-2-carboxamide 5-Methoxypyridine-2-carboxylic acid (30 mg, 0.2 mmol) was dissolved in DMF (1 mL) and HATU (74 mg, 0.2 mmol) and DIPEA (0.7 mL, 4.03 mmol) were added. A solution of 2-(6-methoxy-3-pyridyl)-3,4-dihydro-1H-isoquinolin-7-amine (50 mg, 0.2 mmol) in DMF (1 mL) was added to the reaction mixture and stirred at rt for 1 hour. The reaction mixture was concentrated in vacuo and the residue was triturated with water (2 mL). Purification by basic prep HPLC gave the title compound.

¹H NMR (500 MHz, DMSO-d₆) δ 10.35 (s, 1H), 8.38 (d, J=2.7 Hz, 1H), 8.12 (d, J=8.7 Hz, 1H), 7.88 (d, J=3.0 Hz, 1H), 7.78 (m, 1H), 7.69-7.58 (m, 2H), 7.55 (dd, J=9.0, 3.1 Hz, 1H), 7.13 (d, J=8.3 Hz, 1H), 6.74 (d, J=8.9 Hz, 1H), 4.29 (s, 2H), 3.94 (s, 3H), 3.78 (s, 3H), 3.45 (t, J=5.9 Hz, 2H), 2.87 (t, J=5.7 Hz, 2H). Tr (METCR1603)=4.71 min, (ES⁺) (M+H)⁺ 391.

Method 12

Scheme for Method 12

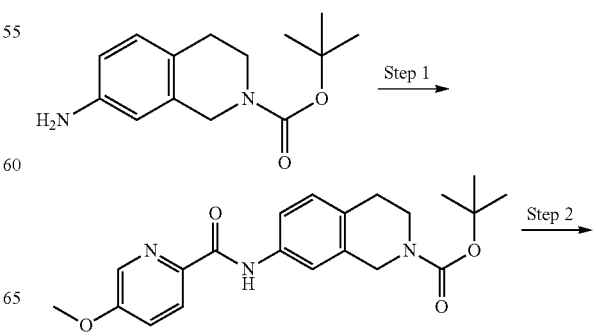

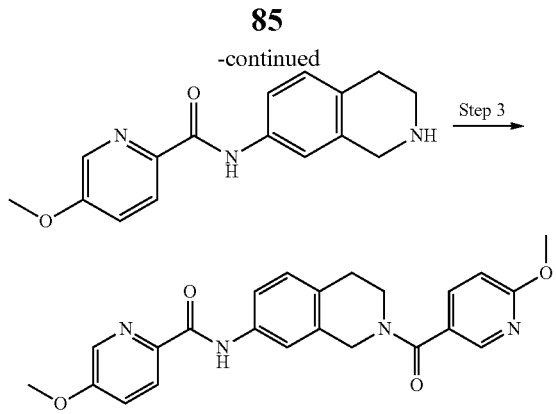

Step 3

Example 12: (5-Methoxy-N-[2-(6-methoxypyridine-3-carbonyl)-1,2,3,4-tetrahydroisoquinolin-7-yl]pyridine-2-carboxamide tert-Butyl-7-[(5-methoxypyridine-2-carbonyl)amino]-3,4-dihydro-1H-isoquinoline-2-carboxylate 5-Methoxypyridine-2-carboxylic acid (308 mg, 2.01 mmol) was dissolved in DMF (5 mL) and HATU (766 mg, 2.01 mmol) and DIPEA (0.7 mL, 4.03 mmol) were added. A solution of tert-butyl-7-amino-3,4-dihydro-1H-isoquinoline-2-carboxylate (500 mg, 2.01 mmol) in DMF (5 mL) was added to the reaction mixture and stirred at rt for 1 hour. The reaction mixture was concentrated in vacuo and the residue was diluted with water (10 mL), this was extracted with EtOAc (2×20 mL). The organic layers were combined and concentrated in vacuo. Purification by column chromatography (silica, 0-80% EtOAc in heptanes) gave the title compound. $^1$H NMR (500 MHz, DMSO-d$_6$) δ 10.36 (s, 1H), 8.38 (d, J=2.9 Hz, 1H), 8.12 (d, J=8.7 Hz, 1H), 7.87-7.48 (m, 3H), 7.13 (d, J=8.3 Hz, 1H), 4.48 (s, 2H), 3.93 (s, 3H), 3.55 (t, J=5.8 Hz, 2H), 2.74 (t, J=5.8 Hz, 2H), 1.43 (s, 9H). Tr (METCR1410)=1.31 min, (ES$^+$) (M+H-tBu)$^+$ 328.

5-Methoxy-N-(1,2,3,4-tetrahydroisoquinolin-7-yl)pyridine-2-carboxamide hydrochloride tert-Butyl-7-[(5-methoxypyridine-2-carbonyl)amino]-3,4-dihydro-1H-isoquinoline-2-carboxylate (500 mg, 3 mmol) was suspended in 4 M HCl in dioxane (9.8 mL) and sonicated. The suspension was stirred at rt overnight. The resultant material was filtered to give the title compound. $^1$H NMR (500 MHz, DMSO-d$_6$) δ 10.46 (s, 1H), 9.29 (s, 2H), 8.38 (d, J=2.8 Hz, 1H), 8.12 (d, J=8.7 Hz, 1H), 7.80 (d, J=1.8 Hz, 1H), 7.70 (dd, J=8.4, 2.1 Hz, 1H), 7.62 (dd, J=8.8, 2.9 Hz, 1H), 7.20 (d, J=8.4 Hz, 1H), 4.26 (t, J=4.5 Hz, 2H), 3.93 (s, 3H), 3.40-3.28 (m, 2H), 2.97 (t, J=6.2 Hz, 2H). Tr (METCR1410)=0.81 min, (ES$^+$) (M+H)$^+$ 284.

(5-Methoxy-N-[2-(6-methoxypyridine-3-carbonyl)-1,2,3,4-tetrahydroisoquinolin-7-yl]pyridine-2-carboxamide 6-Methoxypyridine-3-carboxylic acid (48 mg, 0.31 mmol) was dissolved in DMF (2 mL) and HATU (119 mg, 0.31 mmol) and DIPEA (0.11 mL, 0.63 mmol) were added. In a 12 mL vial 5-methoxy-AA 1,2,3,4-tetrahydroisoquinolin-7-yl)pyridine-2-carboxamide hydrochloride (100 mg, 0.31 mmol) was suspended in DMF (2 mL) and DIPEA (50 µL, 0.31 mmol) was added. The solution was added to the reaction mixture and stirred at rt for 1 hour. The reaction mixture was concentrated in vacuo and the residue was treated with water (5 mL), then acetonitrile (2 mL) and finally MeOH (2 mL) to give the title compound.

$^1$H NMR (250 MHz, 353 K, DMSO-d$_6$) δ 10.12 (s, 1H), 8.37 (d, J=2.5 Hz, 1H), 8.31 (d, J=1.8 Hz, 1H), 8.11 (d, J=8.7 Hz, 1H), 7.80 (dd, J=8.5, 2.4 Hz, 1H), 7.71-7.39 (m, 3H), 7.17 (d, J=8.9 Hz, 1H), 6.88 (dd, J=8.5, 0.6 Hz, 1H), 4.70 (s, 2H), 3.95 (m, 6H), 3.74 (t, J=6.0 Hz, 2H), 2.87 (t, J=5.9 Hz, 2H). Tr (MET-uHPLC-AB-101)=3.17 min, (ES$^+$) (M+H)$^+$ 419.

Method 13

Scheme for Method 13

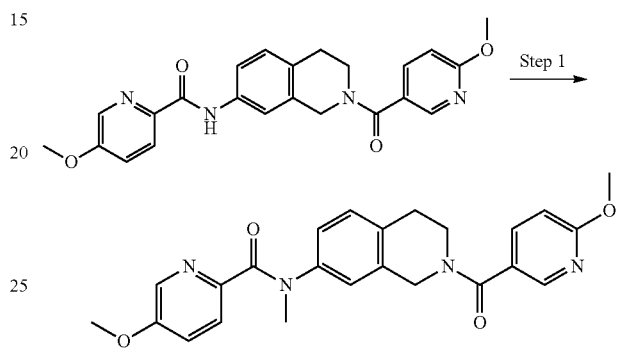

Example 13: (5-Methoxy-N-[2-(6-methoxypyridine-3-carbonyl)-1,2,3,4-tetrahydroisoquinolin-7-yl]-N-methylpyridine-2-carboxamide To a stirred solution of 5-methoxy-N-[2-(6-methoxypyridine-3-carbonyl)-3,4-dihydro-1H-isoquinolin-7-yl]pyridine-2-carboxamide (90%, 50 mg, 0.11 mmol, prepared as described in method 12) in DMF (5 mL) at 0° C. was added NaH (60% in oil) (60%, 5 mg, 0.13 mmol). The reaction was stirred at RT for 10 minutes and iodomethane (10 µL, 0.1 mmol) was added. The reaction mixture was stirred at rt for 30 minutes. Water (5 mL) was added the reaction mixture concentrated in vacuo. Purification by acidic prep HPLC gave the title compound.

$^1$H NMR (250 MHz, 353 K, DMSO-d$_6$) δ 8.40-8.21 (m, 1H), 8.05 (d, J=2.5 Hz, 1H), 7.76 (dd, J=8.5, 2.4 Hz, 1H), 7.60-7.43 (m, 1H), 7.33 (dd, J=8.7, 2.9 Hz, 1H), 7.21-6.56 (m, 4H), 4.60 (s, 2H), 3.94 (s, 3H), 3.82 (s, 3H), 3.68 (t, J=6.0 Hz, 2H), 3.35 (s, 3H), 2.82 (t, J=6.0 Hz, 2H). Tr (METCR1603)=3.68 min, (ES$^+$) (M+H)$^+$ 433.

Method 15

Scheme for Method 15

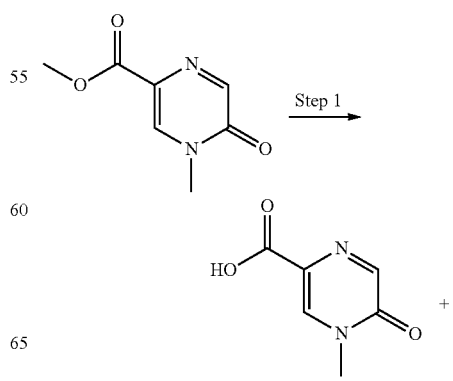

-continued

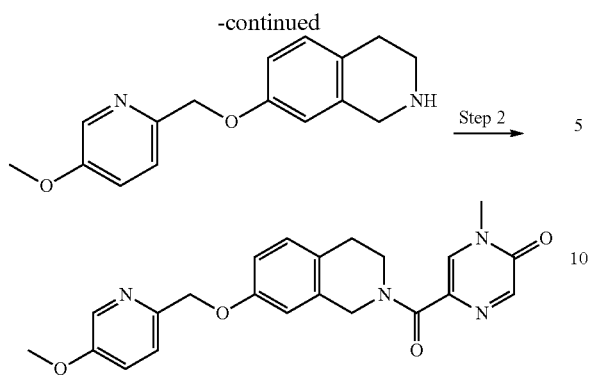

Example 15: 5-{7-[(5-Methoxypyridin-2-yl)methoxy]-1,2,3,4-tetrahydroisoquinoline-2-carbonyl}-1-methyl-1,2-dihydropyrazin-2-one 4-Methyl-5-oxo-4,5-dihydropyrazine-2-carboxylic acid To a solution of methyl 4-methyl-5-oxo-4,5-dihydropyrazine-2-carboxylate (2.0 g, 10.3 mmol) in THF (30 mL) and MeOH (30 mL) was added 1 M NaOH (22.6 mL, 22.6 mmol) at rt and the reaction was stirred for 96 h. The solvent was removed in vacuo. 1 M HCl (23 mL) was added at 0° C. The suspension was stirred at 0° C. for 30 minutes. The material was filtered and dried under high vacuum at 40° C. for 4 hours to give the title compound. The crude product was used with no further purification. $^1$H NMR (250 MHz, DMSO-$d_6$) δ 8.49 (s, 1H), 7.97 (d, J=0.9 Hz, 1H), 3.49 (s, 3H). Tr (METCR1410)=front of solvent, (ES$^+$) (M+H)$^+$= 155.

5-{7-[(5-Methoxypyridin-2-yl)methoxy]-1,2,3,4-tetrahydroisoquinoline-2-carbonyl}-1-methyl-1,2-dihydropyrazin-2-one To a mixture of HATU (185 mg, 0.49 mmol), 4-methyl-5-oxo-4,5-dihydropyrazine-2-carboxylic acid (50 mg, 0.32 mmol) in DMF (4 mL) was added DIPEA (0.11 mL, 0.65 mmol) at 0° C. The reaction was left stirring at rt for 30 minutes. 7-[(5-Methoxypyridin-2-yl)methoxy]-1,2,3,4-tetrahydroisoquinoline hydrochloride (110 mg, 0.36 mmol) was added. The reaction was stirred at rt overnight. The solvent was removed in vacuo and the residue suspended in water (20 mL). The suspension was stirred at rt for 30 minutes. The material was filtered, washed with water and purified by low pH prep HPLC. The pure fractions were combined and the solvent removed by freeze-drying to give the title compound.
$^1$H NMR (500 MHz, DMSO-$d_6$) δ 8.31-8.25 (m, 1H), 8.19 (s, 1H), 7.96 (s, 1H), 7.43 (m, 2H), 7.08 (d, J=8.5 Hz, 1H), 6.83 (m, 2H), 5.06 (m, 2H), 4.71 (s, 2H), 3.83 (s, 3H), 3.79 (s, 2H), 3.48 (s, 3H), 2.80 (s, 2H). Tr (METCR1603)= 3.48 min, (ES$^+$) (M+H)$^+$=407.
Method 16
Scheme for Method 16

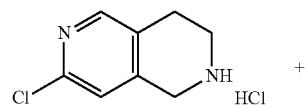

-continued

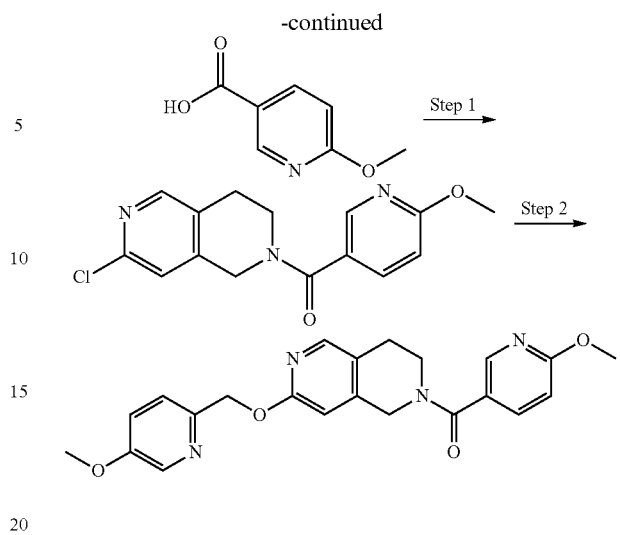

Example 16: 7-[(5-Methoxypyridin-2-yl)methoxy]-2-(6-methoxypyridine-3-carbonyl)-1,2,3,4-tetrahydro-2,6-naphthyridine 7-Chloro-2-(6-methoxypyridine-3-carbonyl)-1,2,3,4-tetrahydro-2,6-naphthyridine To a mixture of HATU (558 mg, 1.47 mmol) and 6-methoxypyridine-3-carboxylic acid (150 mg, 0.98 mmol) in DMF (8 mL) was added DIPEA (340 µL, 1.96 mmol) at 0° C. The reaction was stirred at rt for 30 minutes. 7-Chloro-1,2,3,4-tetrahydro-2,6-naphthyridine hydrochloride (221 mg, 1.08 mmol) was added. The reaction was stirred at rt overnight. The solvent was removed in vacuo and the residue was partitioned between EtOAc (20 mL) and water (30 mL). The aqueous layer was extracted with EtOAc (2×20 mL). The combined organic layers were washed with brine, dried over Na$_2$SO$_4$, filtered and evaporated under reduced pressure and the residue was washed with MeCN. The residue was purified by low pH prep HPLC. The pure fractions were combined and the solvent was removed in vacuo to give the title compound. $^1$H NMR (500 MHz, DMSO-$d_6$) δ 8.32 (d, J=2.1 Hz, 1H), 8.25 (s, 1H), 7.82 (dd, J=8.5, 2.0 Hz, 1H), 7.47 (s, 1H), 6.90 (d, J=8.5 Hz, 1H), 4.75 (s, 2H), 3.91 (s, 3H), 3.66 (s, 2H), 2.88 (t, J=5.7 Hz, 2H). Tr (METCR1410)=0.97 min, (ES$^+$) (M+H)$^+$=304.

7-[(5-Methoxypyridin-2-yl)methoxy]-2-(6-methoxypyridine-3-carbonyl)-1,2,3,4-tetrahydro-2,6-naphthyridine A sealed tube was charged with caesium carbonate (322 mg, 1.00 mmol) and dried with heating under vacuum. The tube was cooled under nitrogen and 7-chloro-2-(6-methoxypyridine-3-carbonyl)-1,2,3,4-tetrahydro-2,6-naphthyridine (100 mg, 0.33 mmol), Pd$_2$(dba)$_3$ (15 mg, 0.02 mmol) and BrettPhos (22 mg, 0.04 mmol) added. Toluene (4 mL) was added via syringe. The reaction mixture was degassed with nitrogen for 5 minutes. (5-Methoxypyridin-2-yl)methanol (928 mg, 0.66 mmol) was added and the reaction mixture stirred at 100° C. for 20 hours. The reaction was cooled to rt and quenched with water (15 mL). The aqueous phases were extracted with EtOAc (2×20 mL). The combined organic layer was washed with brine, dried over Na$_2$SO$_4$, filtered and evaporated under reduced pressure and the residue was purified by low pH prep HPLC to give the title compound.

$^1$H NMR (500 MHz, DMSO-d$_6$) δ 8.31 (d, J=2.2 Hz, 1H), 8.25 (s, 1H), 7.99 (s, 1H), 7.81 (dd, J=8.5, 1.9 Hz, 1H), 7.37 (s, 2H), 6.90 (d, J=8.5 Hz, 1H), 6.83 (s, 1H), 5.31 (s, 2H), 4.72 (s, 2H), 3.90 (s, 3H), 3.81 (s, 3H), 3.65 (d, J=20.2 Hz, 2H), 2.81 (t, J=5.8 Hz, 2H). Tr (METCR1603)=3.73 min, (ES$^+$) (M+H)$^+$=407.

Method 17

Scheme for Method 17

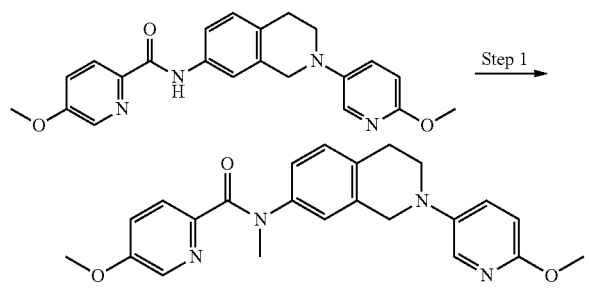

Example 17: 5-Methoxy-N-[2-(6-methoxypyridin-3-yl)-1,2,3,4-tetrahydroisoquinolin-7-yl]-N-methylpyridine-2-carboxamide To a stirred solution of 5-methoxy-N-[2-(6-methoxy-3-pyridyl)-3,4-dihydro-1H-isoquinolin-7-yl]pyridine-2-carboxamide (95%, 30 mg, 0.07 mmol) in DMF (2 mL) at 0° C. was added NaH (60% in oil) (60%, 3.5 mg, 0.09 mmol). The reaction was stirred at rt for 10 minutes and iodomethane (2 µL, 0.04 mmol) was added. The reaction mixture was stirred at rt for 30 minutes. Water (5 mL) was added to the reaction mixture and the mixture was concentrated in vacuo. The crude residue was washed with water (2 mL) and purified by acidic prep HPLC to give the title compound.

$^1$H NMR (250 MHz, 353 K, DMSO-d$_6$) δ 8.05 (d, J=2.8 Hz, 1H), 7.82 (d, J=3.0 Hz, 1H), 7.60-7.37 (m, 2H), 7.32 (dd, J=8.7, 2.9 Hz, 1H), 7.17-6.96 (m, 2H), 6.91 (dd, J=8.0, 2.3 Hz, 1H), 6.70 (d, J=8.9 Hz, 1H), 4.19 (s, 2H), 3.93-3.73 (m, 6H), 3.58-3.31 (m, 5H), 2.83 (t, J=5.9 Hz, 2H). Tr (MET-uHPLC-AB-101)=2.67 min, (ES$^+$) (M+H)$^+$ 405.

Method 18

Scheme for Method 18

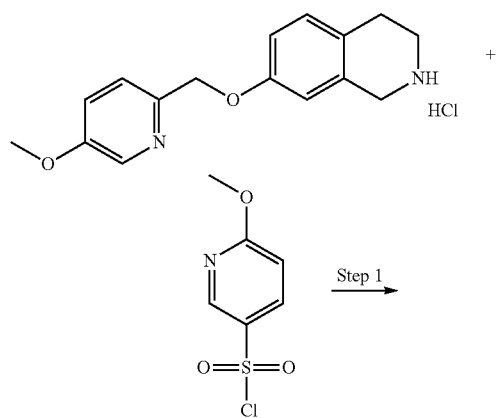

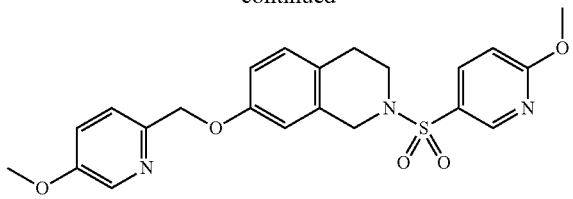

Example 18: 7-[(5-Methoxypyridin-2-yl)methoxy]-2-[(6-methoxypyridin-3-yl)sulfonyl]-1,2,3,4-tetrahydroisoquinoline To a vial were added 7-[(5-methoxy-2-pyridyl)methoxy]-1,2,3,4-tetrahydroisoquinoline hydrochloride (prepared by method 1) (50 mg, 0.16 mmol), DIPEA (90 µL, 0.57 mmol) and DCM (2 mL) at rt and the mixture stirred. 4-tert-Butylbenzenesulfonyl chloride (41 mg, 0.20 mmol) was added and the vial purged with nitrogen, sealed and the reaction stirred for 45 minutes. Water (2 mL) was added and the organic layer separated. The aqueous layer was extracted with DCM (3×2 mL) and the combined organic layers were dried over MgSO$_4$, filtered and concentrated to give the crude product. The product was purified by column chromatography (silica, eluting with 0-50% EtOAc in heptane) to give the title compound.

$^1$H NMR (500 MHz, Chloroform-d) δ 8.64 (d, J=2.5 Hz, 1H), 8.29 (d, J=2.8 Hz, 1H), 7.92 (dd, J=8.8, 2.5 Hz, 1H), 7.39 (d, J=8.6 Hz, 1H), 7.21 (dd, J=8.6, 2.9 Hz, 1H), 6.98 (d, J=8.4 Hz, 1H), 6.84-6.77 (m, 2H), 6.64 (d, J=2.5 Hz, 1H), 5.09 (s, 2H), 4.24 (s, 2H), 4.00 (s, 3H), 3.87 (s, 3H), 3.37 (t, J=5.9 Hz, 2H), 2.85 (t, J=5.9 Hz, 2H). Tr (MET-uHPLC-AB-101)=3.37 min, (ES$^+$) (M+H)$^+$ 442.

Method 19

Scheme for Method 19

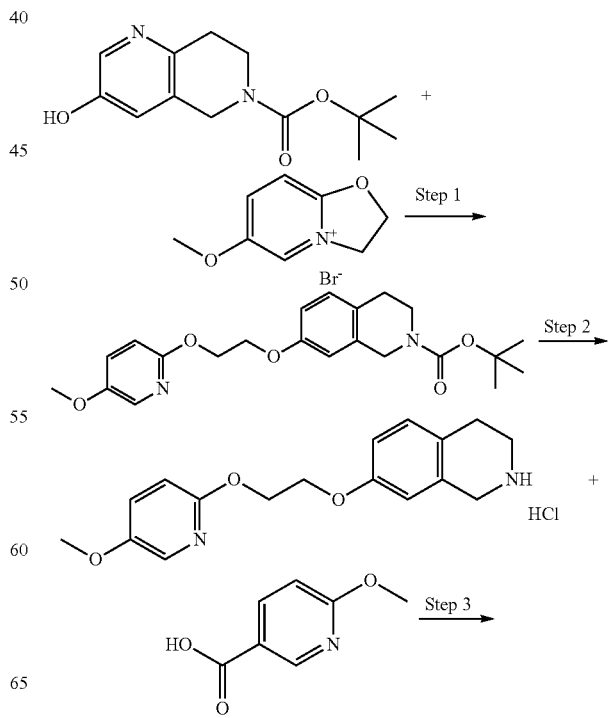

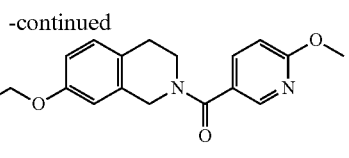

Example 19: 7-{2-[(5-Methoxypyridin-2-yl)oxy]ethoxy}-2-(6-methoxypyridine-3-carbonyl)-1,2,3,4-tetrahydroisoquinoline tert-Butyl 7-[2-[(5-methoxy-2-pyridyl)oxy]ethoxy]-3,4-dihydro-1H-isoquinoline-2-carboxylate tert-Butyl 7-hydroxy-3,4-dihydro-1H-isoquinoline-2-carboxylate (54 mg, 0.22 mmol), KI (36 mg, 0.22 mmol) and $Cs_2CO_3$ (140 mg, 0.43 mmol) were dissolved in DMF (3 mL) and a solution of 6-methoxy-2,3-dihydrooxazolo[3,2-a]pyridin-4-ium bromide (50 mg, 0.22 mmol) in DMF (2 mL) was added. The reaction mixture was stirred at rt overnight. 6-methoxy-2,3-dihydrooxazolo[3,2-a]pyridin-4-ium bromide (110 mg, 0.46 mmol) was added and the reaction mixture was stirred at rt overnight. The reaction mixture was concentrated under reduced pressure and the residue washed with water and further purified by basic prep HPLC to give the title compound. Tr (METCR1410)=1.12 min, (ES$^+$) (M+H)$^+$ 401, 87%.

7-[2-[(5-Methoxy-2-pyridyl)oxy]ethoxy]-1,2,3,4-tetrahydroisoquinoline hydrochloride tert-Butyl 7-[2-[(5-methoxy-2-pyridyl)oxy]ethoxy]-3,4-dihydro-1H-isoquinoline-2-carboxylate (40 mg, 0.10 mmol) was suspended in 4 M HCl in dioxane (2.2 mL), sonicated and stirred at rt for 15 minutes. The precipitate was collected and dried under vacuum to afford the title compound. Tr (METCR1410)=0.74 min, (ES$^+$) (M+H)$^+$ 301.

7-{2-[(5-Methoxypyridin-2-yl)oxy]ethoxy}-2-(6-methoxypyridine-3-carbonyl)-1,2,3,4-tetrahydroisoquinoline 6-Methoxypyridine-3-carboxylic acid (14 mg, 0.090 mmol) was dissolved in DMF (1 mL) and HATU (34 mg, 0.090 mmol) and DIPEA (3 µL, 0.18 mmol) were added. In a 12 mL vial 7-[2-[(5-methoxy-2-pyridyl)oxy]ethoxy]-1,2,3,4-tetrahydroisoquinoline hydrochloride (30 mg, 0.090 mmol) was suspended in DMF (2 mL) and DIPEA (20 µL, 0.09 mmol) was added. The solution was added to the reaction mixture and stirred at rt for 30 minutes under a nitrogen atmosphere. The reaction mixture was concentrated under reduced pressure and the residue was diluted with water (5 mL) and extracted into ethyl acetate (2×5 mL). The organic layers were combined and concentrated under reduced pressure. Purification by basic prep HPLC gave the title compound.

$^1$H NMR (250 MHz, 353 K, DMSO-d$_6$) δ 8.29 (d, J=1.9 Hz, 1H), 7.78 (dd, J=8.5, 2.4 Hz, 1H), 7.31-7.23 (m, 2H), 7.11-7.04 (m, 1H), 6.90-6.84 (m, 1H), 6.81-6.75 (m, 2H), 6.38-6.31 (m, 1H), 4.65 (s, 2H), 4.27-4.16 (m, 4H), 3.94 (s, 3H), 3.69 (t, J=6.0 Hz, 2H), 3.65 (s, 3H), 2.84-2.77 (m, 2H). Tr (MET-uHPLC-AB-101)=2.51 min, (ES$^+$) (M+H)$^+$ 436.

Method 20

Scheme for Method 20

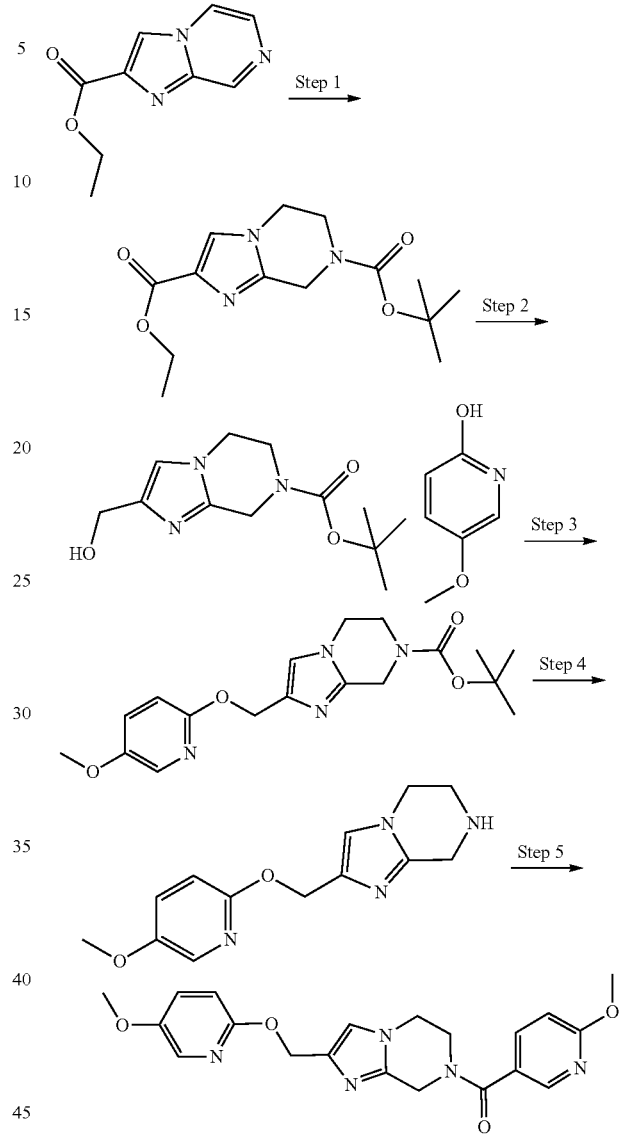

Example 20: 5-Methoxy-2-{[7-(6-methoxypyridine-3-carbonyl)-5H,6H,7H,8H-imidazo[1,2-a]pyrazin-2-yl]methoxy}pyridine 7-tert-Butyl 2-ethyl 5H,6H,7H,8H-imidazo[1,2-a]pyrazine-2,7-dicarboxylate To a solution of ethyl imidazo[1,2-a]pyrazine-2-carboxylate (500 mg, 2.62 mmol) in 15 mL ethanol was added Boc$_2$O (1500 mg, 6.8 mmol) and Pd/C (10%, 100 mg, 0.09 mmol) under a hydrogen atmosphere. The mixture was stirred at rt for 24 hours. The reaction mixture was filtered and the filtrate concentrated under reduced pressure. The residue was purified by column chromatography (silica, eluting with 0-100% methanol in DCM) to give the title compound. $^1$H NMR (500 MHz, DMSO-d$_6$) δ 7.84 (s, 1H), 4.21 (q, J=7.1 Hz, 2H), 4.13-3.89 (m, 2H), 3.77 (t, J=5.4 Hz, 2H), 3.18 (d, J=5.2 Hz, 2H), 1.44 (s, 9H), 1.26 (t, J=7.1 Hz, 3H). Tr (METCR1410)=0.96 min m/z (ES$^+$) (M+H)$^+$ 296, 78%.

tert-Butyl 2-(hydroxymethyl)-5H,6H,7H,8H-imidazo[1,2-a]pyrazine-7-carboxylate To a stirred solution of 7-tert-butyl 2-ethyl 5H,6H,7H,8H-imidazo[1,2-a]pyrazine-2,7-dicarboxylate (78%, 600 mg, 2.03 mmol) in anhydrous THF (20 mL) was added lithium aluminium hydride (2.4 M in THF, 850 μL) at 0° C. The mixture was stirred at the same temperature for 30 minutes. The reaction mixture was quenched with saturated sodium sulfate solution. The mixture was dried over anhydrous $Na_2SO_4$, filtered and concentrated in vacuo. The residue was purified by column chromatography (silica, eluting with 0-100% MeOH in DCM) to give the title compound. $^1$H NMR (500 MHz, DMSO-$d_6$) δ 6.92 (s, 1H), 4.48 (s, 2H), 4.29 (d, J=5.3 Hz, 2H), 4.09 (q, J=5.2 Hz, 1H), 3.93 (t, J=5.5 Hz, 2H), 3.73 (t, J=5.4 Hz, 2H), 1.44 (s, 9H). Tr (METCR1410)=0.68 min m/z (ES$^+$) (M+H)$^+$ 254, 89%.

tert-Butyl 2-{[(5-methoxypyridin-2-yl)oxy]methyl}-5H,6H,7H,8H-imidazo[1,2-a]pyrazine-7-carboxylate tert-Butyl 2-(hydroxy methyl)-6,8-dihydro-5H-imidazo[1,2-a]pyrazine-7-carboxylate (200 mg, 0.79 mmol), 5-methoxypyridin-2-ol (109 mg, 0.87 mmol) and CMBP (0.31 mL, 1.18 mmol) were suspended in anhydrous toluene (6 mL) and the reaction was heated to 100° C. for 2 hours in a nitrogen atmosphere. The reaction mixture was cooled to rt and concentrated in vacuo, the residue was purified by column chromatography (silica, eluting with 0-100% EtOAc in heptane) to give the title compound. $^1$H NMR (500 MHz, DMSO-$d_6$) δ 7.86 (d, J=3.1 Hz, 1H), 7.38 (dd, J=8.9, 3.1 Hz, 1H), 7.14 (s, 1H), 6.74 (d, J=8.9 Hz, 1H), 5.07 (s, 2H), 4.52 (s, 2H), 4.10-3.92 (m, 2H), 3.76 (m, 5H), 1.44 (s, 9H). Tr (METCR1410)=0.95 min m/z (ES$^+$) (M+H)$^+$ 361, 88%.

2-({5H,6H,7H,8H-imidazo[1,2-a]pyrazin-2-yl}methoxy)-5-methoxy pyridine tert-Butyl 2-[(5-methoxy-2-pyridyl)oxymethyl]-6,8-dihydro-5H-imidazo[1,2-a]pyrazine-7-carboxylate (100 mg, 0.28 mmol) was stirred in a solution of 4 M HCl in dioxane (6 mL) for 1 hour. The reaction mixture was concentrated to dryness and dissolved in water (1 mL). The solution was neutralised with sat. aq. $K_2CO_3$ and extracted into DCM (3×5 mL). The combined organics were dried over $MgSO_4$ and concentrated to give the title compound. Tr (METCR1600)=1.30 min m/z (ES$^+$) (M+H)$^+$ 261.

5-Methoxy-2-{[7-(6-methoxypyridine-3-carbonyl)-5H,6H,7H,8H-imidazo[1,2-a]pyrazin-2-yl]methoxy}pyridine 6-Methoxypyridine-3-carboxylic acid (35 mg, 0.23 mmol) was dissolved in DML (1 mL) and HATU (88 mg, 0.23 mmol) and DIPEA (80 μL, 0.46 mmol) were added. A solution of 2-[(5-methoxy-2-pyridyl)oxymethyl]-5H,6H,7H,8H-tetrahydroimidazo[1,2-(2]pyrazine (60 mg, 0.23 mmol) in DML (1 mL) was added and the reaction stirred at rt for 30 minutes. The reaction mixture was concentrated in vacuo and the residue diluted with water (5 mL). The mixture was extracted with ethyl acetate (2×5 mL). The organic layers were combined and concentrated in vacuo. Purification by basic prep HPLC gave the title compound.
$^1$H NMR (250 MHz, 353 K DMSO-$d_6$) δ 8.34 (d, J=1.8 Hz, 1H), 8.01-7.69 (m, 2H), 7.35 (dd, J=8.9, 3.1 Hz, 1H), 7.10 (s, 1H), 6.89 (d, J=8.5 Hz, 1H), 6.72 (d, J=8.9 Hz, 1H), 5.12 (s, 2H), 4.71 (s, 2H), 4.16-4.00 (m, 2H), 3.99-3.86 (m, 5H), 3.79 (s, 3H). Tr (METCR1603)=3.35 min, (ES$^+$) (M+H)$^+$ 396.

Method 21

Scheme for Method 21

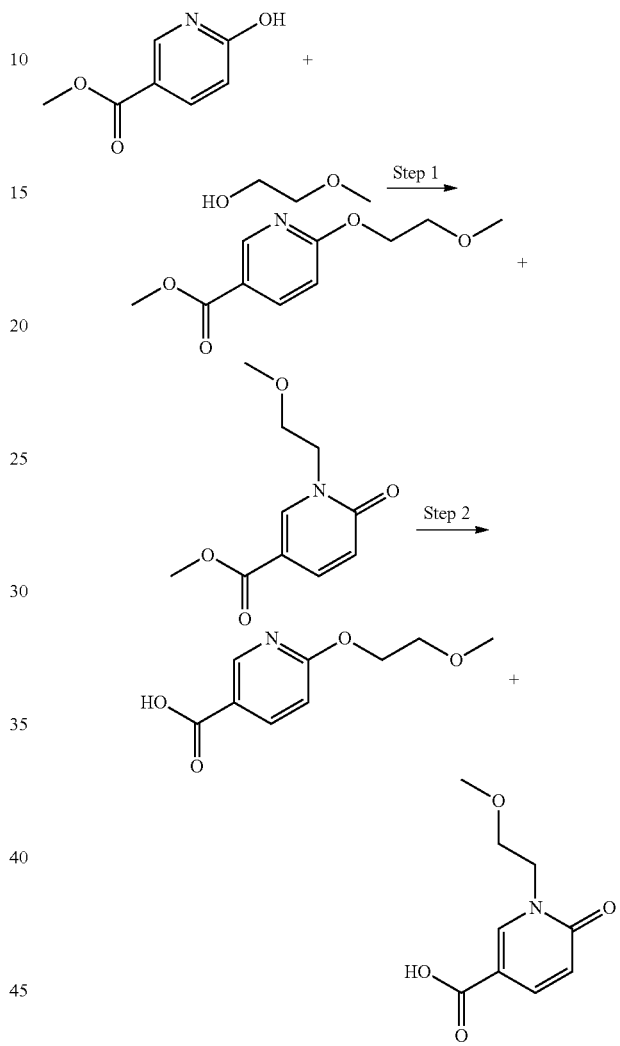

Methyl 6-(2-methoxyethoxy)pyridine-3-carboxylate

Methyl 6-hydroxypyridine-3-carboxylate (0.10 g, 0.65 mmol) was dissolved in toluene (3 mL) and stirred. 2-Methoxyethanol (70 μL, 0.85 mmol) was added followed by CMBP (0.22 mL, 0.85 mmol). The mixture was sealed and stirred at 70° C. under a nitrogen atmosphere for 2.5 hours. The solvent was removed under reduced pressure and water (10 mL) was added to the reaction mixture and extracted with DCM (3×10 mL). The combined organic layers were dried over $MgSO_4$, filtered and concentrated to give the crude product. The product was purified by column chromatography (silica, eluting with 0-50% EtOAc in heptane) to give the title compound. $^1$H NMR (500 MHz, DMSO-$d_6$) δ 8.73 (d, J=2.4 Hz, 1H), 8.17 (dd, J=8.7, 2.4 Hz, 1H), 6.94 (d, J=8.7 Hz, 1H), 4.48-4.43 (m, 2H), 3.84 (s, 3H), 3.69-3.65 (m, 2H), 3.29 (s, 3H).

Methyl 1-(2-methoxyethyl)-6-oxo-pyridine-3-carboxylate

Methyl 1-(2-methoxyethyl)-6-oxo-pyridine-3-carboxylate was obtained from the previous step as a side product. $^1$H NMR (500 MHz, DMSO-$d_6$) δ 8.39 (d, J=2.5 Hz, 1H), 7.80 (dd, J=9.5, 2.6 Hz, 1H), 6.44 (d, J=9.5 Hz, 1H), 4.16 (t, J=5.2 Hz, 2H), 3.79 (s, 3H), 3.57 (t, J=5.2 Hz, 2H), 3.23 (s, 3H).

6-(2-Methoxyethoxy)pyridine-3-carboxylic acid

Methyl 6-(2-methoxyethoxy)pyridine-3-carboxylate (25 mg, 0.12 mmol) was dissolved in 1,4-dioxane (1 mL) and treated with 2 M NaOH (0.30 mL, 0.59 mmol). The reaction mixture was stirred for 4 hours. The reaction mixture was concentrated under reduced pressure and water (5 mL) was added. It was then extracted with IPA: CHCl$_3$ (3:1, 3×10 mL) and the combined organic layers were dried over MgSO$_4$, filtered and concentrated to give the title compound. $^1$H NMR (500 MHz, DMSO-$d_6$) δ 8.69 (d, J=2.1 Hz, 1H), 8.13 (dd, J=8.7, 2.3 Hz, 1H), 6.90 (d, J=8.7 Hz, 1H), 4.47-4.42 (m, 2H), 3.70-3.65 (m, 2H), 3.29 (s, 3H).

1-(2-Methoxyethyl)-6-oxo-pyridine-3-carboxylic acid 1-(2-Methoxyethyl)-6-oxo-pyridine-3-carboxylic acid was also prepared by the previous step. $^1$H NMR (500 MHz, DMSO-$d_6$) δ 12.81 (s, 1H), 8.32 (d, J=2.4 Hz, 1H), 7.78 (dd, J=9.5, 2.5 Hz, 1H), 6.41 (d, J=9.5 Hz, 1H), 4.14 (t, J=5.2 Hz, 2H), 3.57 (t, J=5.2 Hz, 2H), 3.24 (s, 3H).

Method 22

Scheme for Method 22

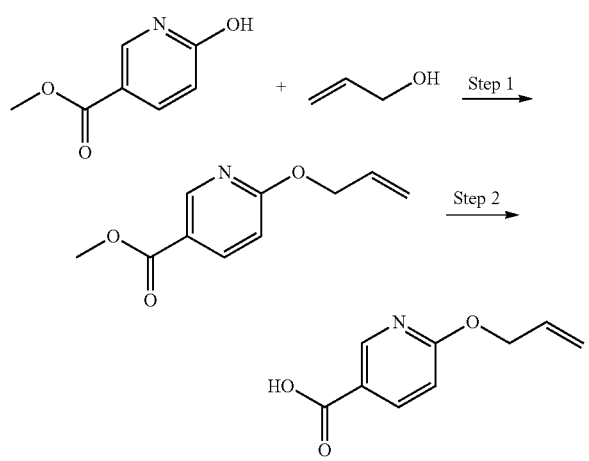

Methyl 6-allyloxypyridine-3-carboxylate

To a solution of prop-2-en-1-ol (37 mg, 0.64 mmol) and DMF (2 mL) was added NaH (23 mg, 0.58 mmol) at 0° C. under a nitrogen atmosphere and stirred for 10 minutes. Methyl 6-chloropyridine-3-carboxylate (100 mg, 0.58 mmol) was added and the mixture was stirred at rt for 2 hours. Water (10 mL) was added to the reaction mixture and extracted with EtOAc (3×10 mL). The combined organic layers were dried over Na$_2$SO$_4$, filtered and concentrated under reduced pressure to give the crude product. The product was purified by high pH prep HPLC to give the title compound. $^1$H NMR (500 MHz, DMSO-$d_6$) δ 8.74 (d, J=2.0 Hz, 1H), 8.22-8.15 (m, 1H), 6.96 (d, J=8.6 Hz, 1H), 6.13-6.01 (m, 1H), 5.42-5.35 (m, 1H), 5.29-5.22 (m, 1H), 4.90 (dt, J=5.4, 1.4 Hz, 2H), 3.84 (s, 3H).

6-Allyloxypyridine-carboxylic acid

Methyl 6-allyloxypyridine-3-carboxylate (26 mg, 0.14 mmol) and allyl 6-allyloxypyridine-3-carboxylate (18 mg, 0.08 mmol) were dissolved in 1,4-dioxane (2 mL) and treated with 2 M NaOH (27 mg, 0.67 mmol). The reaction mixture was stirred overnight at rt. The reaction mixture was concentrated under reduced pressure and water was added. The product was acidified with 1 M HCl (pH=3) which formed a precipitate. The mixture was concentrated under reduced pressure to give the title compound. $^1$H NMR (500 MHz, DMSO-$d_6$) δ 8.71 (d, J=2.3 Hz, 1H), 8.15 (dd, J=8.7, 2.4 Hz, 1H), 6.93 (d, J=8.7 Hz, 1H), 6.13-6.01 (m, 1H), 5.38 (dd, J=17.3, 1.7 Hz, 1H), 5.25 (dd, J=10.5, 1.5 Hz, 1H), 4.89 (dt, J=5.4, 1.4 Hz, 2H).

Method 23

Scheme for Method 23

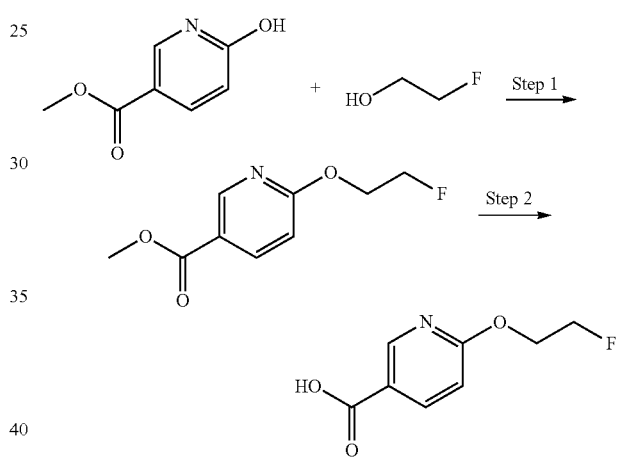

Methyl 6-(2-fluoroethoxy)pyridine-3-carboxylate

Methyl 6-hydroxypyridine-3-carboxylate (100 mg, 0.65 mmol) was dissolved in toluene (3 mL) and stirred. 2-Fluoroethanol (50 µL, 0.85 mmol) was added followed by CMBP (220 µL, 0.85 mmol). The mixture was sealed and stirred at 70° C. under a nitrogen atmosphere for 2.5 hours. The solvent was removed under reduced pressure to give a yellow/brown oil. Water was added to the reaction mixture and extracted with DCM (3×10 mL). The combined organic layers were dried over MgSO$_4$, filtered and concentrated under reduced pressure. The product was purified by column chromatography (silica, eluting with 0-70% EtOAc in heptane) to give the title compound. $^1$H NMR (500 MHz, DMSO-$d_6$) δ 8.74 (d, J=2.4 Hz, 1H), 8.19 (dd, J=8.7, 2.4 Hz, 1H), 6.99 (d, J=8.7 Hz, 1H), 4.84-4.78 (m, 1H), 4.74-4.69 (m, 1H), 4.65-4.60 (m, 1H), 4.59-4.53 (m, 1H), 3.85 (s, 3H).

6-(2-Fluoroethoxy)pyridine-3-carboxylic acid

Methyl 6-(2-fluoroethoxy)pyridine-3-carboxylate (50 mg, 0.25 mmol) was dissolved in 1,4-dioxane (2 mL) and treated with 2 M NaOH (0.63 mL, 1.26 mmol). The reaction mixture was stirred for 2.5 hours. The reaction mixture was concentrated under reduced pressure and water (5 mL) was added. The product was acidified with 1 M HCl (pH=3). The mixture was concentrated under reduced pressure to give the title compound. ¹H NMR (250 MHz, DMSO-d₆) δ 8.71 (d, J=1.7 Hz, 1H), 8.16 (dd, J=8.7, 2.4 Hz, 1H), 6.96 (d, J=8.0 Hz, 1H), 4.92-4.78 (m, 1H), 4.72-4.61 (m, 2H), 4.54-4.47 (m, 1H).

Method 24

Scheme for Method 24

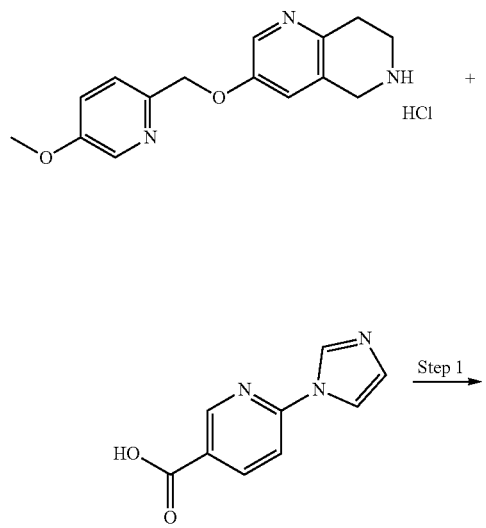

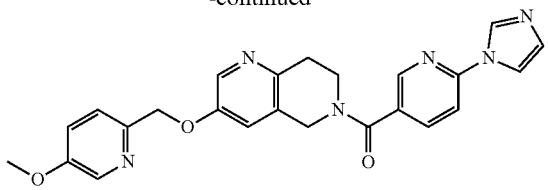

Example 24: 6-[6-(1H-Imidazol-1-yl)pyridine-3-carbonyl]-3-[(5-methoxypyridin-2-yl)methoxy]-5,6,7,8-tetrahydro-1,6-naphthyridine 6-Imidazol-1-ylpyridine-3-carboxylic acid (33 mg, 0.17 mmol) was dissolved in DMF (2 mL) and HATU (65 mg, 0.17 mmol) and DIPEA (40 µL, 0.23 mmol) was added at rt under a nitrogen atmosphere. 3-[(5-Methoxy-2-pyridyl)methoxy]-5H,6H,7H,8H-tetrahydro-1,6-naphthyridine hydrochloride (prepared as described in method 1) (50 mg, 0.16 mmol) was suspended in DMF (2 mL) and DIPEA (40 µL, 0.23 mmol) was added and the reaction mixture stirred at rt for 2 hours. The reaction mixture was concentrated under reduced pressure and the residue triturated with water (5 mL) and ethanol (2 mL) to give the title compound. ¹H NMR (250 MHz, 353 K, DMSO-d₆) δ 8.60 (dd, J=1.6 Hz, 1H), 8.53 (s, 1H), 8.28 (d, J=2.2 Hz, 1H), 8.19 (d, J=2.8 Hz, 1H), 8.09 (dd, J=8.4, 2.3 Hz, 1H), 7.98-7.93 (m, 1H), 7.86 (dd, J=8.4, 0.7 Hz, 1H), 7.50-7.37 (m, 2H), 7.34 (d, 1H), 7.17-7.12 (m, 1H), 5.15 (s, 2H), 4.75 (s, 2H), 3.88-3.77 (m, 5H), 2.92 (t, J=6.1 Hz, 2H). Tr (MET-uHPLC-AB-105)= 2.22 min, (ES⁺) (M+H)⁺ 443.

The following compounds were similarly prepared:

| Example | Structure | Mol. Weight | LCMS data |
|---|---|---|---|
| 24.1 | 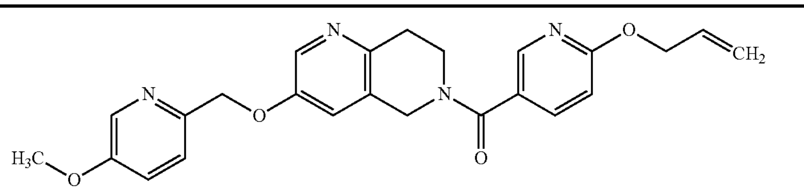 | 432.48 | Tr (MET-uHPLC-AB-101) = 2.27 min, (ES⁺) (M + H)⁺ 433; (See Method 22 for acid synthesis) |
| 24.2 | 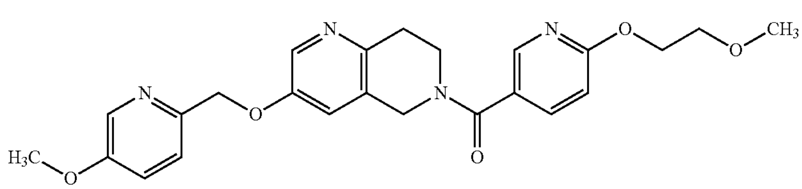 | 450.50 | Tr (MET-uHPLC-AB-101) = 2.27 min, (ES⁺) (M + H)⁺ 433; (See Method 21 for acid synthesis) |
| 24.3 | 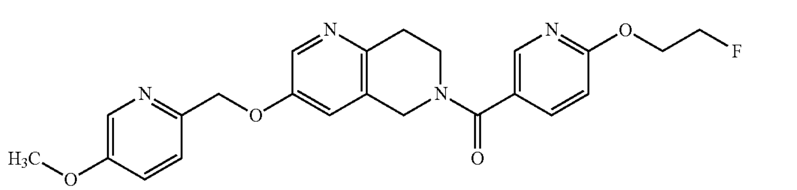 [SMILES: COc1ccc(COc2cnc3c(c2)CN(C(=O)c2ccc(OCCF)nc2)CC3)nc1] | 438.46 | Tr (MET-uHPLC-AB-105) = 2.52 min, (ES⁺) (M + H)⁺ 439; (See Method 23 for acid synthesis) |

| Example | Structure | Mol. Weight | LCMS data |
|---|---|---|---|
| 24.4 | 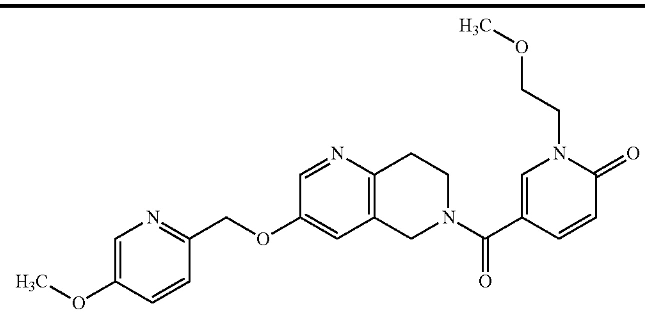 | 450.50 | Tr (METCR1603) = 3.09 min, (ES+) (M + H)+ 451; (See Method 21 for acid synthesis) |

Method 25

Scheme for Method 25

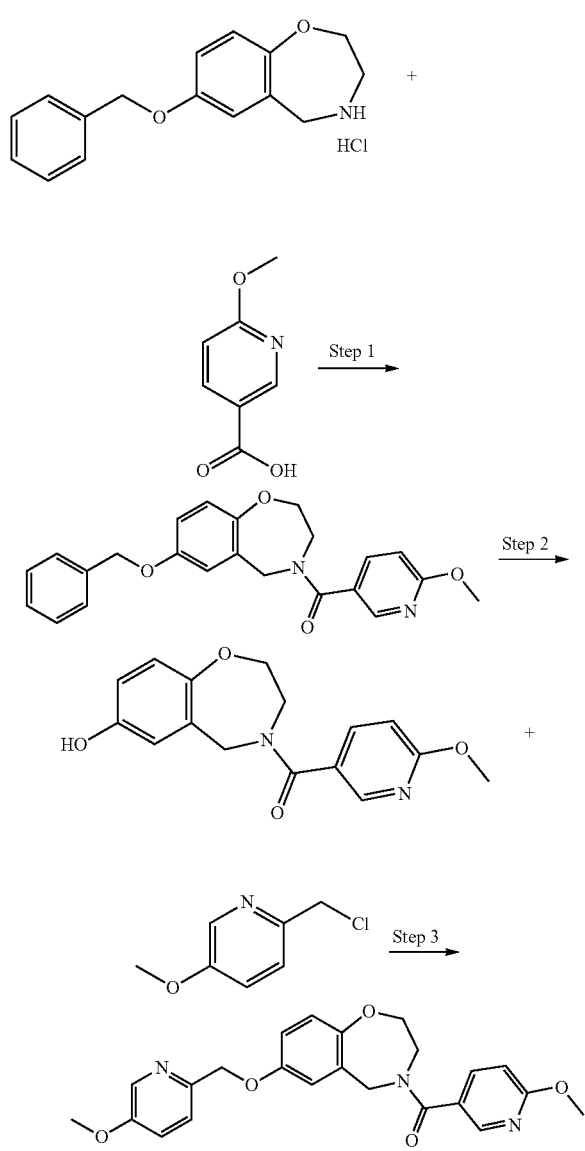

Example 25: 7-[(5-Methoxypyridin-2-yl)methoxy]-4-(6-methoxypyridine-3-carbonyl)-2,3,4,5-tetrahydro-1,4-benzoxazepine (7-Benzyloxy-3,5-dihydro-2H-1,4-benzoxazepin-4-yl)-(6-methoxy-3-pyridyl)methanone 7-Benzyloxy-2,3,4,5-tetrahydro-1,4-benzoxazepine hydrochloride (200 mg, 0.69 mmol) was added to a stirred solution of 6-methoxypyridine-3-carboxylic acid (110 mg, 0.72 mmol), DIPEA (0.35 mL, 2.06 mmol) and HATU (313 mg, 0.82 mmol) in DMF (10 mL). The reaction mixture was stirred at rt for 1 hour. The reaction mixture was concentrated in vacuo and the residue dissolved in water (2 mL) and extracted into DCM (3×5 mL). The combined organics were dried (phase separator cartridge) and concentrated in vacuo. The crude residue was purified by column chromatography (silica, eluting with 20-100% EtOAc in heptane) to give the title compound. $^1$H NMR (250 MHz, 353K DMSO-$d_6$) δ 8.15 (d, J=1.9 Hz, 1H), 7.65 (dd, J=8.5, 2.4 Hz, 1H), 7.49-7.28 (m, 5H), 6.97-6.79 (m, 3H), 6.70 (s, 1H), 5.03 (s, 2H), 4.59 (s, 2H), 4.13-4.06 (m, 2H), 3.92 (s, 3H), 3.91-3.82 (m, 2H). Tr (METCR1410)=1.18 min m/z (ES+) (M+H)+ 391.1.

(7-Hydroxy-3,5-dihydro-2H-1,4-benzoxazepin-4-yl)-(6-methoxy-3-pyridyl)methanone

Pd/C (10%, 24 mg) was added to a stirred solution of (7-benzyloxy-3,5-dihydro-2H-1,4-benzoxazepin-4-yl)-(6-methoxy-3-pyridyl)methanone (220 mg, 0.56 mmol) in ethanol:THF (1:1, 20 mL). The reaction mixture was stirred under an atmosphere of hydrogen for 22 hours. The reaction mixture was filtered through Celite, washing with EtOH and EtOAc. The filtrate was concentrated in vacuo to give the title compound. $^1$H NMR (500 MHz, DMSO-$d_6$) δ 9.25 (s, 1H), 8.19 (s, 1H), 7.70 (s, 1H), 7.19-5.92 (m, 4H), 4.72-4.29 (m, 2H), 4.14-3.64 (m, 7H). Tr (METCR1410)=0.92 min m/z (ES+) (M+H)+ 301.1.

7-[(5-Methoxypyridin-2-yl)methoxy]-4-(6-methoxypyridine-3-carbonyl)-2,3,4,5-tetrahydro-1,4-benzoxazepine To a solution of (7-hydroxy-3,5-dihydro-2H-1,4-benzoxazepin-4-yl)-(6-methoxy-3-pyridyl)methanone (90%, 180 mg, 0.54 mmol), potassium iodide (90 mg, 0.54 mmol) and caesium carbonate (356 mg, 1.08 mmol) in DMF (10 mL) was added and a solution of 2-(chloromethyl)-5-methoxypyridine (102 mg, 0.65 mmol) in DMF (5 mL). The reaction mixture was stirred at rt overnight. The reaction mixture was concentrated in vacuo and partitioned between DCM (25 mL) and water (5 mL). The aqueous phase was washed with chloroform:isopropanol (3:1, 2×5 mL). The combined organics were dried (phase separator cartridge) and concentrated in vacuo. The crude residue was purified by column chromatography (silica, eluting with 0-100% EtOAc in heptane) and the relevant fractions were combined and concentrated in vacuo. The residue was dissolved in MeCN (0.5 mL) and water (1 mL) and lyophilized to give the title compound.

$^1$H NMR (250 MHz, 353 K, DMSO-d$_6$) δ 8.30-8.24 (m, 1H), 8.15 (d, J=2.1 Hz, 1H), 7.65 (dd, J=8.5, 2.4 Hz, 1H), 7.47-7.36 (m, 2H), 6.92 (d, J=8.7 Hz, 1H), 6.89-6.80 (m, 2H), 6.70 (s, 1H), 5.03 (s, 2H), 4.59 (s, 2H), 4.14-4.04 (m, 2H), 3.92 (s, 3H), 3.91-3.82 (m, 5H). Tr (MET-uHPLC-AB-101)=2.63 min, (ES$^+$) (M+H)$^+$ 422.

Method 26

Scheme for Method 26

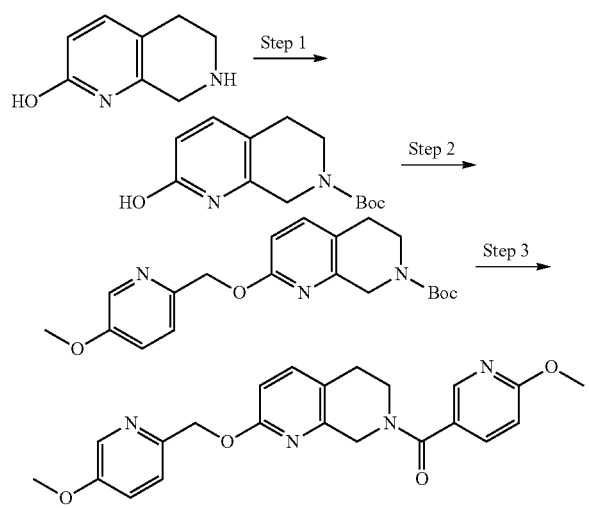

Example 26: 2-[(5-Methoxypyridin-2-yl)methoxy]-7-(6-methoxypyridine-3-carbonyl)-5,6,7,8-tetrahydro-1,7-naphthyridine tert-Butyl 2-hydroxy-5,6,7,8-tetrahydro-1,7-naphthyridine-7-carboxylate To a solution of 5,6,7,8-tetrahydro-1,7-naphthyridin-2-ol (500 mg, 3.16 mmol) in THF (15 mL) was added di-tert-butyl dicarbonate (759 mg, 3.48 mmol) at 0° C., followed by triethylamine (0.88 mL, 6.33 mmol). The reaction was stirred at rt for 16 hours. The reaction was quenched with water and extracted with EtOAc (3×20 mL). The combined organic layer was dried over Na$_2$SO$_4$, filtered and evaporated under reduced pressure. The crude product was dissolved in EtOAc (10 mL) and the solution allowed to stand at rt over the weekend. The material was filtered and washed with ether and dried under vacuum at 40° C. for 3 hours to give the title compound. $^1$H NMR (500 MHz, Chloroform-d) δ 7.20 (d, J=9.3 Hz, 1H), 6.45 (d, J=9.2 Hz, 1H), 4.31 (s, 2H), 3.66 (t, J=5.3 Hz, 2H), 2.75 (t, J=5.5 Hz, 2H), 1.48 (s, 9H). Tr (METCR1410)=0.91 min m/z (ES$^+$) (M+H)$^+$ 251.

tert-Butyl 2-[(5-methoxypyridin-2-yl)methoxy]-5,6,7,8-tetrahydro-1,7-naphthyridine-7-carboxylate A mixture of tert-butyl 2-hydroxy-5,6,7,8-tetrahydro-1,7-naphthyridine-7-carboxylate (100 mg, 0.40 mmol), (5-methoxypyridin-2-yl)methanol (56 mg, 0.40 mmol) and CMBP (116 mg, 0.48 mmol) in toluene (3 mL) in a sealed tube was stirred at 100° C. for 3 hours. The reaction was cooled to rt, and the solvent removed in vacuo. The residue was purified by low pH prep HPLC to give the title compound. $^1$H NMR (500 MHz, Chloroform-d$_6$) δ 8.31 (d, J=2.9 Hz, 1H), 7.41 (d, J=8.6 Hz, 1H), 7.30 (d, J=8.4 Hz, 1H), 7.20 (dd, J=8.6, 2.9 Hz, 1H), 6.67 (d, J=8.4 Hz, 1H), 5.41 (s, 2H), 4.48 (s, 2H), 3.86 (s, 3H), 3.70 (t, J=5.9 Hz, 2H), 2.85 (t, J=5.5 Hz, 2H), 1.49 (s, 10H). Tr (METCR1673)=1.16 min m/z (ES$^+$) (M+H)$^+$ 372.

tert-Butyl 1-[(5-methoxypyridin-2-yl)methyl]-2-oxo-1,2,5,6,7,8-hexahydro-1,7-naphthyridine-7-carboxylate Also isolated from the previous reaction, 52 mg (35% yield), as off-white solid. $^1$H NMR (500 MHz, Chloroform-d) δ 8.19 (d, J=2.9 Hz, 1H), 7.30 (d, J=8.6 Hz, 1H), 7.14 (dd, J=8.6, 2.9 Hz, 1H), 7.09 (d, J=9.3 Hz, 1H), 6.55 (d, J=9.3 Hz, 1H), 5.32 (s, 2H), 4.30 (s, 2H), 3.83 (s, 3H), 3.62 (s, 2H), 2.89 (t, J=5.6 Hz, 2H), 1.47 (s, 9H). Tr (METCR1673)=1.03 min m/z (ES$^+$) (M+H)$^+$ 372.

2-[(5-Methoxypyridin-2-yl)methoxy]-7-(6-methoxypyridine-3-carbonyl)-5,6,7,8-tetrahydro-1,7-naphthyridine To a solution of tert-butyl 2-[(5-methoxypyridin-2-yl)methoxy]-5,6,7,8-tetrahydro-1,7-naphthyridine-7-carboxylate (58 mg, 0.16 mmol) in DCM (4 mL) was added TFA (0.48 mL, 6.25 mmol), and the reaction stirred at rt overnight. The solvent was removed in vacuo. The residue was purified by high pH prep HPLC. The pure fractions were combined and the solvent was removed in vacuo. The deBoc product was dissolved in DMF (4 mL). To this solution was added 6-methoxypyridine-3-carboxylic acid (24 mg, 0.16 mmol), HATU (89 mg, 0.23 mmol) and DIPEA (101 mg, 0.78 mmol) at 0° C. The mixture was stirred at rt overnight. The solvent was removed in vacuo and the crude product was purified by low pH prep HPLC to give the title compound.

$^1$H NMR (500 MHz, DMSO-d$_6$) δ 8.32 (d, J=1.9 Hz, 1H), 8.29 (d, J=2.6 Hz, 1H), 7.82 (d, J=7.3 Hz, 1H), 7.66-7.44 (m, 3H), 6.89 (d, J=8.5 Hz, 1H), 6.74 (s, 1H), 5.33 (s, 2H), 4.66 (m, 2H), 3.90 (s, 3H), 3.84 (s, 3H), 3.72 (m, 2H), 2.86 (t, J=5.8 Hz, 2H). Tr (METCR1603)=3.82 min m/z (ES$^+$) (M+H)$^+$ 407.

The following compounds were similarly prepared:

| Example | Structure | Mol. Weight | LCMS data |
|---|---|---|---|
| 26.1 | 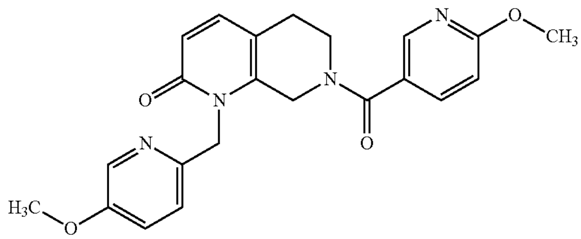 | 406.44 | Tr (METCR1603) = 3.11 min m/z (ES⁺) (M + H)⁺ 408 |

Method 27
Scheme for Method 27

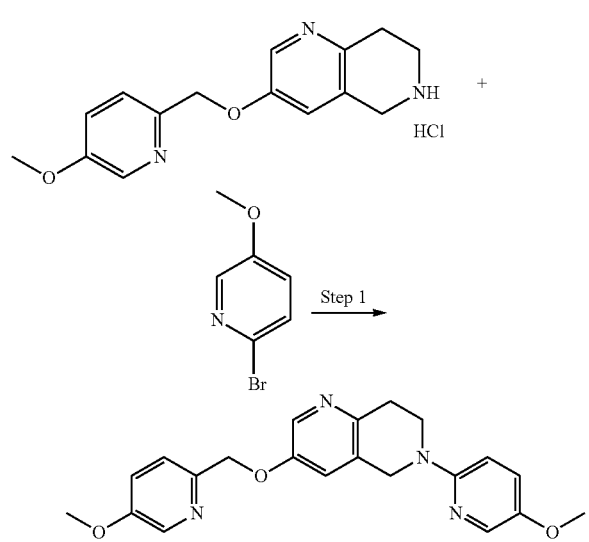

Example 27: 6-(5-Methoxypyridin-2-yl)-3-[(5-methoxypyridin-2-yl)methoxy]-5,6,7,8-tetrahydro-1,6-naphthyridine 3-[(5-Methoxy-2-pyridyl)methoxy]-5,6,7,8-tetrahydro-1,6-naphthyridine hydrochloride (50 mg, 0.16 mmol, prepared by method 1), 2-bromo-5-methoxypyridine (46 mg, 0.24 mmol), sodium tert-butoxide (20 mg, 0.21 mmol), Pd$_2$(dba)$_3$ (7 mg, 0.01 mmol) and BINAP (15 mg, 0.02 mmol) were suspended in tert-butanol (2 mL) and the mixture was heated at 110° C. in the microwave for 1 hour. The reaction mixture was then dissolved in methanol and filtered. The precipitate was washed with water (1 mL) to give the title compound.

$^1$H NMR (500 MHz, DMSO-d$_6$) δ 8.29 (d, J=2.9 Hz, 1H), 8.14 (d, J=2.8 Hz, 1H), 7.89 (d, J=3.0 Hz, 1H), 7.49 (d, J=8.5 Hz, 1H), 7.43 (dd, J=8.6, 2.9 Hz, 1H), 7.39-7.31 (m, 1H), 7.32-7.17 (m, 1H), 6.93 (d, J=9.2 Hz, 1H), 5.15 (s, 2H), 4.60 (s, 2H), 3.84 (s, 3H), 3.80 (t, J=6.0 Hz, 2H), 3.73 (s, 3H), 2.86 (t, J=5.8 Hz, 2H). Tr (METCR1603)=3.85 min, (ES⁺) (M+H)⁺ 379.

The following compounds were similarly prepared:

| Example | Structure | Mol. Weight | LCMS data |
|---|---|---|---|
| 27.1 | 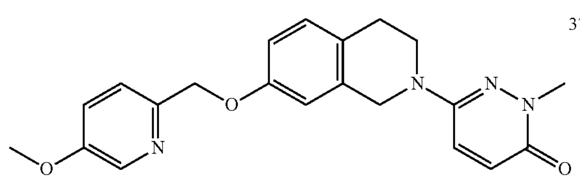 | 378.432 | Tr(METCR1603 High pH 7 min) = 3.86 min, (ES+) (M + H)+ 379.1 |
| 27.2 | 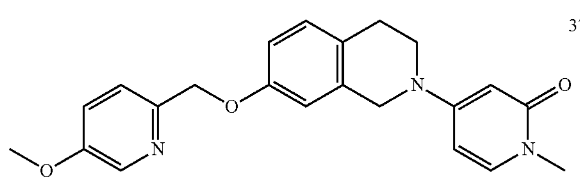 | 377.444 | Tr(METCR1603 High pH 7 min) = 3.65 min, (ES+) (M + H)+ 378.1 |

Method 28
Scheme for Method 28

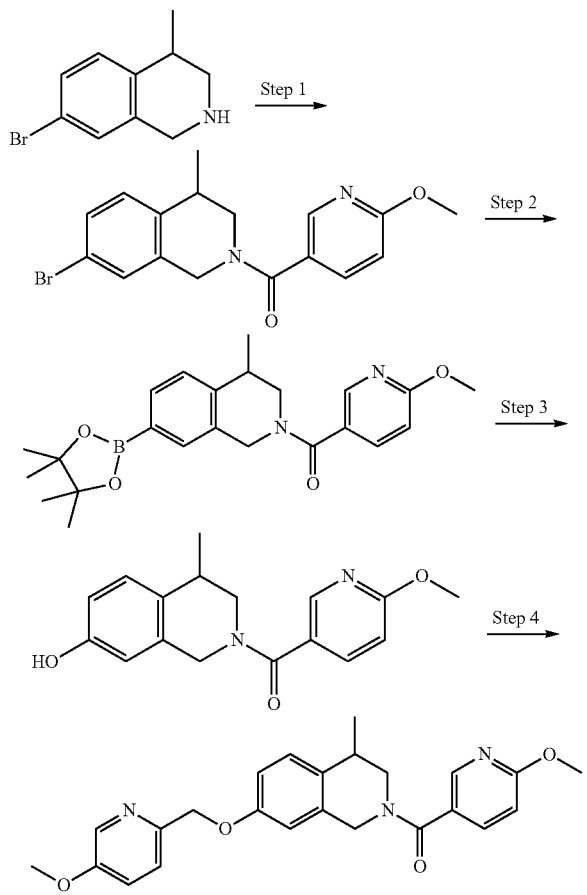

Example 28: 2-[(5-Methoxypyridin-2-yl)methoxy]-N-(1-methyl-6-oxo-1,6-dihydropyridazin-3-yl)pyridine-4-carboxamide 7-Bromo-2-(6-methoxypyridine-3-carbonyl)-4-methyl-1,2,3,4-tetrahydroisoquinoline To a mixture of HATU (185 mg, 0.49 mmol), 6-methoxypyridine-3-carboxylic acid (230 mg, 1.50 mmol) in DMF (8 mL) was added DIPEA (0.78 mL, 4.50 mmol) at 0° C. The reaction was left stirring at rt for 30 minutes. 7-Bromo-4-methyl-1,2,3,4-tetrahydroisoquinoline hydrochloride (433 mg, 1.65 mmol) was added. The reaction was stirred at rt overnight. The solvent was removed in vacuo. The residue was suspended in water (30 mL) and the product was extracted with EtOAc (3×20 mL). The combined organic layer was washed with brine, dried over Na$_2$SO$_4$, filtered and evaporated under reduced pressure. The crude product was treated with DCM. The material was concentrated in vacuo and the residue purified by low pH prep HPLC to give the title compound. $^1$H NMR (250 MHz, DMSO-d$_6$) δ 8.28 (d, J=1.8 Hz, 1H), 7.77 (dd, J=8.5, 2.4 Hz, 1H), 7.38 (d, J=7.4 Hz, 2H), 7.22 (d, J=8.3 Hz, 1H), 6.87 (d, J=8.5 Hz, 1H), 4.72 (q, J=17.2 Hz, 2H), 3.93 (s, 3H), 3.71 (dd, J=13.0, 4.6 Hz, 1H), 3.54 (dd, J=13.0, 6.2 Hz, 1H), 1.19 (d, J=6.9 Hz, 3H). Tr (METCR1410 2 min)=1.2 min m/z (ES$^+$) (M+H)$^+$ 361 & 363.

2-(6-Methoxypyridine-3-carbonyl)-4-methyl-1,2,3,4-tetrahydroisoquinolin-7-ol

7-Bromo-2-(6-methoxypyridine-3-carbonyl)-4-methyl-1,2,3,4-tetrahydroisoquinoline (420 mg, 1.16 mmol) was dissolved in THF (15 mL) and degassed with a stream of nitrogen for 5 minutes. Bis(pinacolato)diboron (325 mg, 1.28 mmol), KOAc (285 mg, 2.91 mmol) and PdCl$_2$(dppf) (85 mg, 0.12 mmol) were added, and the reaction was heated to 80° C. for 5 hours. The reaction was cooled to rt, and quenched with water (50 mL). The aqueous phase was extracted with EtOAc (2×30 mL). The combined organic layers were washed with brine, dried over Na$_2$SO$_4$, filtered and evaporated under reduced pressure, and the residue was purified by column chromatography (silica, eluting with 0-60% EtOAc in heptane) to give the title compound. Tr (METCR1410)=1.28 min m/z (ES$^+$) (M+H)$^+$ 409, 74%.

2-(6-Methoxypyridine-3-carbonyl)-4-methyl-1,2,3,4-tetrahydroisoquinolin-7-ol

To a solution of 2-(6-methoxypyridine-3-carbonyl)-4-methyl-7-(4,4,5,5-tetramethyl-1,3,2-dioxaborolan-2-yl)-1,2,3,4-tetrahydroisoquinoline (74%, 342 mg, 0.62 mmol) was dissolved in THF (6 mL) and water (3 mL) and NaBO$_3$.4H$_2$O (238 mg, 1.55 mmol) was added. The reaction was stirred at rt for 3 hours. The solvent was removed in vacuo, and the residue was diluted with NH$_4$Cl (20 mL). The aqueous phase was extracted with DCM-MeOH (5:1, 3×10 mL). The combined organic layers were dried over Na$_2$SO$_4$, filtered and evaporated under reduced pressure. The crude product was purified by low pH prep HPLC to give the title compound. $^1$H NMR (250 MHz, DMSO-d$_6$) δ 8.26 (d, J=1.9 Hz, 1H), 7.76 (dd, J=8.5, 2.4 Hz, 1H), 7.04 (d, J=8.3 Hz, 1H), 6.87 (d, J=8.5 Hz, 1H), 6.64 (dd, J=8.3, 2.5 Hz, 1H), 6.53 (s, 1H), 4.73-4.49 (m, 2H), 3.93 (s, 3H), 3.69 (dd, J=12.9, 4.6 Hz, 1H), 3.47 (dd, J=12.8, 6.4 Hz, 1H), 1.15 (d, J=6.9 Hz, 3H). Tr (METCR1410)=0.98 min m/z (ES$^+$) (M+H)$^+$ 299.

2-[(5-Methoxypyridin-2-yl)methoxy]-N-(1-methyl-6-oxo-1,6-dihydropyridazin-3-yl)pyridine-4-carboxamide A mixture of 2-(6-methoxypyridine-3-carbonyl)-4-methyl-1,2,3,4-tetrahydroisoquinolin-7-ol (140 mg, 0.47 mmol), (5-methoxypyridin-2-yl)methanol (72 mg, 0.52 mmol) and CMBP (136 mg, 0.56 mmol) in toluene (5 mL) in a sealed tube was stirred at 100° C. for 3 hours. The reaction was cooled to rt, and the solvent removed in vacuo. The residue was purified by low pH prep HPLC followed by column chromatography (silica, eluting with 20-100% EtOAc in heptane) to give the title compound.

$^1$H NMR (250 MHz, 353 K, DMSO-d$_6$) δ 8.27 (m, 2H), 7.77 (dd, J=8.5, 2.4 Hz, 1H), 7.46-7.34 (m, 2H), 7.17 (d, J=8.4 Hz, 1H), 6.92-6.80 (m, 3H), 5.07 (s, 2H), 4.78-4.54 (m, 2H), 3.93 (s, 3H), 3.85 (s, 3H), 3.71 (d, J=12.9, 4.6 Hz, 1H), 3.50 (dd, J=12.9, 6.5 Hz, 1H), 3.00-2.88 (m, 1H), 1.17 (d, J=6.9 Hz, 3H). Tr (METCR1603)=4.3 min m/z (ES$^+$) (M+H)$^+$ 420, 100%.

Method 29
Scheme for Method 29

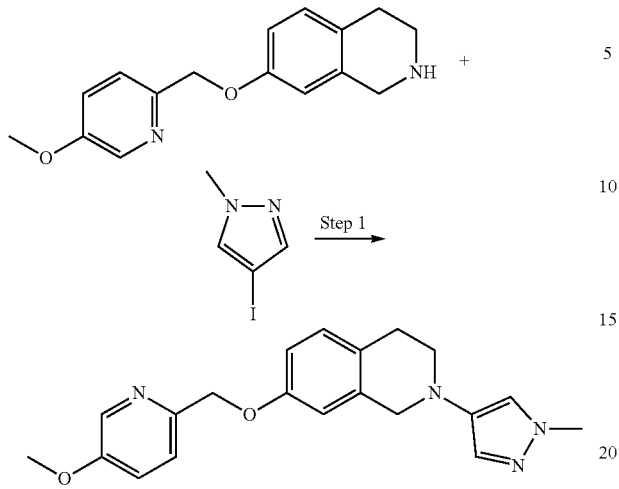

Example 29: 7-[(5-Methoxypyridin-2-yl)methoxy]-2-(1-methyl-1H-pyrazol-4-yl)-1,2,3,4-tetrahydroisoquinoline To a solution of 7-[(5-methoxy-2-pyridyl)methoxy]-1,2,3,4-tetrahydroisoquinoline hydrochloride (30 mg, 0.1 mmol, prepared by method 1) in ethylene glycol (4 mL) was added copper (I) iodide (2 mg, 0.01 mmol), potassium phosphate (52 mg, 0.24 mmol) and 4-iodo-1-methyl-pyrazole (20 µL, 0.12 mmol). The reaction mixture was irradiated under microwave conditions at 120° C. for 7 hours under a nitrogen atmosphere. After cooling to rt, the mixture was filtered and concentrated in vacuo. Water (5 mL) was added and extracted into DCM (5 mL×3). The combined organic layers were dried over anhydrous $Na_2SO_4$, filtered and concentrated in vacuo. The crude residue was purified by basic prep HPLC to give the title compound.

$^1$H NMR (500 MHz, DMSO-$d_6$) δ 8.28 (d, J=2.3 Hz, 1H), 7.58-7.37 (m, 2H), 7.32 (s, 1H), 7.22 (s, 1H), 7.03 (d, J=8.3 Hz, 1H), 6.92-6.61 (m, 2H), 5.06 (s, 2H), 3.99 (s, 2H), 3.83 (s, 3H), 3.73 (s, 3H), 3.15 (t, J=5.9 Hz, 2H), 2.79 (t, J=5.8 Hz, 2H). Tr (METCR1603)=3.84 min, (ES$^+$) (M+H)$^+$ 351.

The following compounds were similarly prepared:

| Example | Structure | Mol. Weight | LCMS data |
|---|---|---|---|
| 29.1 | 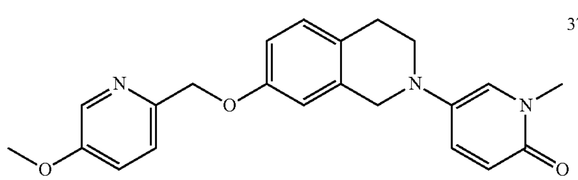 | 377.444 | Tr(METCR1603 High pH 7 min) = 3.5 min, (ES+) (M + H)+ 378.2 |

Method 30

Scheme for Method 30

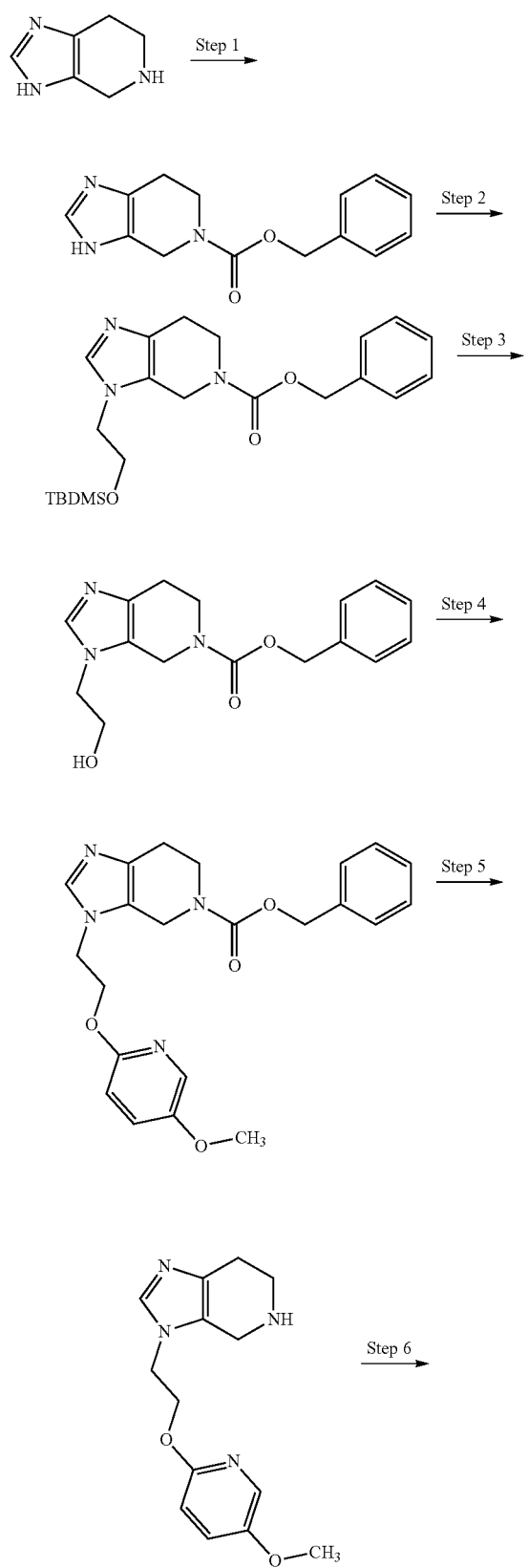

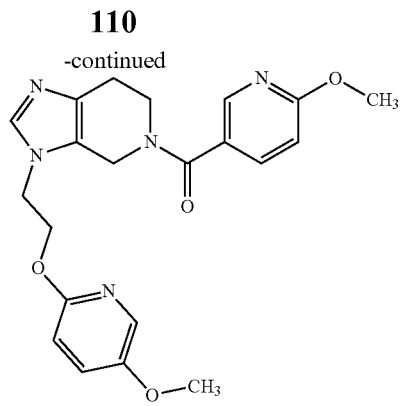

Example 30: 2-Methoxy-5-(3-{2-[(5-methoxypyridin-2-yl)oxy]ethyl}-3H,4H,5H,6H,7H-imidazo[4,5-c]pyridine-5-carbonyl)pyridine Benzyl 3H,4H,5H,6H,7H-imidazo[4,5-t]pyridine-5-carboxylate A mixture of 4,5,6,7-tetrahydro-1H-imidazo[4,5-c]pyridine dihydrochloride (2.0 g, 10 mmol), NaHCO$_3$ (2.4 g, 28 mmol) and N-(benzyloxycarbonyloxy)succinimide (2.5 g, 10 mmol) in dioxane/water (1:1, 80 mL) was stirred for 16 hours at rt. The reaction was quenched with water (20 mL) and brine (100 mL). The aqueous phase was extracted with EtOAc (3×50 mL). Combined organic layers were washed with brine (50 mL), dried over Na$_2$SO$_4$, filtered and evaporated under reduced pressure, which was purified by SCX column, washed with DCM (5 volumes) and eluting the product with 10% (7 M NH$_3$ in MeOH) in DCM to give the title compound. $^1$H NMR (500 MHz, Chloroform-d) δ 7.51 (s, 1H), 7.35 (dd, J=16.9, 5.4 Hz, 5H), 5.17 (s, 2H), 4.57 (s, 2H), 3.81 (s, 2H), 2.71 (s, 2H). Tr (METCR1410)=0.81 min m/z (ES$^+$) (M+H)$^+$ 258.

Benzyl 3-{2-[(tert-butyldimethylsilyl)oxy]ethyl}-3H,4H,5H,6H,7H-imidazo[4,5-t]pyridine-5-carboxylate To a solution of benzyl 3H,4H,5H,6H,7H-imidazo[4,5-c]pyridine-5-carboxylate (1.5 g, 5.83 mmol) in DMF (30 mL) at 0° C. was added LiHMDS (1.0 M in THF/ethylbenzene, 7.0 mL, 7.0 mmol) dropwise. The reaction was stirred at 0° C. for 30 minutes and (2-bromoethoxy)(tert-butyl)dimethylsilane (1.9 mL, 8.75 mmol) was added and the reaction mixture stirred at 0° C. for 0.5 hours and at rt overnight. The reaction was quenched with water (200 mL) and the aqueous phase extracted with EtOAc (3×50 mL). The combined organic layers were washed with brine, dried over Na$_2$SO$_4$, filtered and evaporated under reduced pressure and the residue was purified by column chromatography (silica, eluting with 0-10% MeOH in DCM) to give the title compound (inseparable mixture of regioisomers). Tr (METCR1410)=1.09 min m/z (ES$^+$) (M+H)$^+$ 416.

Benzyl 3-(2-hydroxyethyl)-3H,4H,5H,6H,7H-imidazo[4,5-c]pyridine-5-carboxylate

To a solution of benzyl 3-{2-[(tert-butyldimethylsilyl)oxy]ethyl}-3H,4H,5H,6H,7H-imidazo[4,5-c]pyridine-5-carboxylate (1.46 g, 3.34 mmol) in THF (20 mL) at 0° C. was added TBAF (1 M in THF, 4.34 mL, 4.34 mmol) dropwise. The reaction was stirred at rt for 3 hours. The solvent was removed in vacuo. The residue was purified by high pH prep HPLC to give the title compound (inseparable mixture of regioisomers). Tr (METCR1410)=0.79 min m/z (ES$^+$) (M+H)$^+$ 302.

Benzyl 3-{2-[(5-methoxypyridin-2-yl)oxy]ethyl}-3H,4H,5H,6H,7H-imidazo[4,5-t]pyridine-5-carboxylate A mixture of 2-fluoro-5-methoxypyridine (734 mg, 5.77 mmol), benzyl 3-(2-hydroxyethyl)-3H,4H,5H,6H,7H-imidazo[4,5-c]pyridine-5-carboxylate (870 mg, 2.88 mmol) and Cs$_2$CO$_3$ (2.35 g, 7.22 mmol) in DMSO (12 ml) in a sealed tube was stirred at 80° C. for 5 hours. Further Cs$_2$CO$_3$ (1.17 g, 3.61 mmol) was added and the reaction stirred at 80° C. for a further 18 hours. The reaction was cooled to rt, and the material was filtered. The crude product was purified by high pH prep HPLC to give the title compound (inseparable mixture of regioisomers). Tr (METCR1410)=0.98 min m/z (ES$^+$) (M+H)$^+$ 409.

2-(2-{3H,4H,5H,6H,7H-Imidazo[4,5-c]pyridin-3-yl}ethoxy)-5-methoxypyridine

To a solution of benzyl 3-{2-[(5-methoxypyridin-2-yl)oxy]ethyl}-3H,4H,5H,6H,7H-imidazo[4,5-c]pyridine-5-carboxylate (350 mg, 0.86 mmol) in EtOH (10 mL) was charged with Pd/C (91 mg, 0.09 mmol) at rt. The reaction was stirred at rt under a hydrogen atmosphere overnight. The reaction was filtered through a pad of Celite and washed with MeOH thoroughly. The filtrate was concentrated under reduced pressure and the residue was purified by high pH prep HPLC to give the title compound. $^1$H NMR (500 MHz, DMSO-d$_6$) δ 7.82 (d, J=3.1 Hz, 1H), 7.42 (s, 1H), 7.39 (dd, J=9.0, 3.1 Hz, 1H), 6.75 (d, J=9.0 Hz, 1H), 4.36 (t, J=5.3 Hz, 2H), 4.16 (t, J=5.3 Hz, 2H), 3.76 (s, 3H), 3.70 (s, 2H), 2.85 (t, J=5.6 Hz, 2H), 2.40-2.34 (m, 3H). Tr (METCR1600) =2.80 min m/z (ES$^+$) (M+H)$^+$ 275.

2-Methoxy-5-(3-{2-[(5-methoxypyridin-2-yl)oxy]ethyl}-3H,4H,5H,6H,7H-imidazo[4,5-c]pyridine-5-carbonyl)pyridine To a mixture of HATU (82 mg, 0.22 mmol) and 6-methoxypyridine-3-carboxylic acid (22 mg, 0.14 mmol) in DMF (3 mL) was added DIPEA (75 µL, 0.43 mmol) at 0° C. The reaction was stirred at rt for 30 minutes. 2-(2-{3H,4H,5H,6H,7H-Imidazo[4,5-c]pyridin-3-yl}ethoxy)-5-methoxypyridine (39 mg, 0.14 mmol) was added and the reaction stirred at rt for 3 hours. The solvent was removed in vacuo and the residue purified by high pH prep HPLC to give the title compound.
$^1$H NMR (250 MHz, 353 K, DMSO-d$_6$) δ 8.29 (d, J=2.1 Hz, 1H), 7.84-7.72 (m, 2H), 7.51 (s, 1H), 7.34 (dd, J=8.9, 3.1 Hz, 1H), 6.87 (d, J=8.5 Hz, 1H), 6.67 (d, J=8.9 Hz, 1H), 4.69 (s, 2H), 4.43 (t, J=5.2 Hz, 2H), 4.23 (t, J=5.2 Hz, 2H), 3.93 (s, 3H), 3.78 (s, 3H), 3.71 (t, J=5.7 Hz, 2H), 2.60 (t, J=5.7 Hz, 2H). Tr (METCR1600)=3.36 min m/z (ES$^+$) (M+H)$^+$ 410.
Method 31
Scheme for Method 31

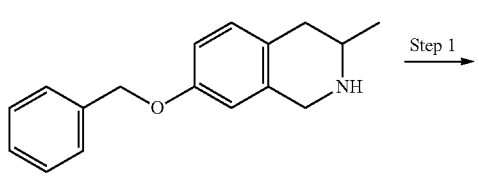

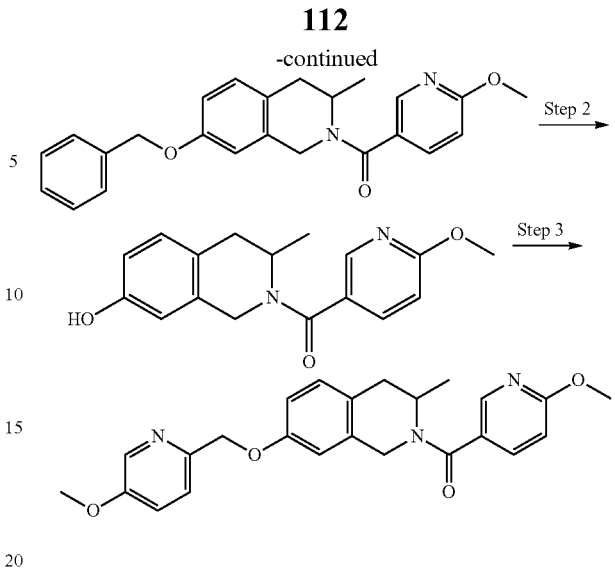

Example 31: 7-[(5-Methoxypyridin-2-yl)methoxy]-2-(6-methoxypyridine-3-carbonyl)-3-methyl-1,2,3,4-tetrahydroisoquinoline

7-(Benzyloxy)-2-(6-Methoxypyridine-3-carbonyl)-3-methyl-1,2,3,4-tetrahydroisoquinoline To a mixture of HATU (745 mg, 1.96 mmol) and 6-methoxypyridine-3-carboxylic acid (200 mg, 1.31 mmol) in DMF (6 mL) was added DIPEA (680 µL, 3.92 mmol) at 0° C. The reaction was left stirring at rt for 30 minutes. 7-(Benzyloxy)-3-methyl-1,2,3,4-tetrahydroisoquinoline (347 mg, 1.37 mmol) was added. The reaction was stirred at rt overnight. The reaction was quenched with water (50 mL) and the aqueous phase extracted with EtOAc (3×20 mL). The combined organic layers were washed with brine, dried over Na$_2$SO$_4$, filtered and concentrated in vacuo and the residue was purified by column chromatography (silica, eluting with 0-50% EtOAc in heptane) to give the title compound. $^1$H NMR (250 MHz, DMSO-d$_6$) δ 8.25 (dd, J=2.4, 0.6 Hz, 1H), 7.75 (dd, J=8.5, 2.4 Hz, 1H), 7.47-7.25 (m, 5H), 7.12-7.05 (m, 1H), 6.91-6.83 (m, 3H), 5.07 (s, 2H), 4.88 (d, J=17.2 Hz, 1H), 4.59-4.44 (m, 1H), 4.36 (d, J=17.4 Hz, 1H), 3.93 (s, 3H), 2.60 (d, J=2.4 Hz, 1H), 1.12 (d, J=6.7 Hz, 3H). Tr (METCR1410)=1.27 min m/z (ES$^+$) (M+H)$^+$ 389.

2-(6-Methoxypyridine-3-carbonyl)-3-methyl-1,2,3,4-tetrahydroisoquinolin-7-ol To a solution of 7-(benzyloxy)-2-(6-methoxypyridine-3-carbonyl)-3-methyl-1,2,3,4-tetrahydroisoquinoline (200 mg, 0.51 mmol) in EtOH (5 mL) was added Pd/C (10 mg, 0.10 mmol) and the reaction mixture stirred under a hydrogen atmosphere at rt overnight. The reaction was filtered through a pad of Celite, and the material washed with MeOH thoroughly. The filtrate was concentrated under reduced pressure to give the title compound. $^1$H NMR (250 MHz, 353K, DMSO-d$_6$) δ 8.24 (d, J=2.4 Hz, 1H), 7.74 (dd, J=8.5, 2.4 Hz, 1H), 6.95 (d, J=8.1 Hz, 1H), 6.87 (d, J=8.5 Hz, 1H), 6.63 (dd, J=8.1, 2.5 Hz, 1H), 6.55 (s, 1H), 4.80 (d, J=17.0 Hz, 1H), 4.49 (s, 1H), 4.30 (d, J=17.2 Hz, 1H), 3.93 (s, 3H), 1.11 (d, J=6.7 Hz, 3H). Tr (METCR1410)=1.01 min, (ES$^+$) (M+H)$^+$ 299.

7-[(5-Methoxypyridin-2-yl)methoxy]-2-(6-methoxy-pyridine-3-carbonyl)-3-methyl-1,2,3,4-tetrahydroisoquinoline A mixture of 2-(6-methoxypyridine-3-carbonyl)-3-methyl-1,2,3,4-tetrahydroisoquinolin-7-ol (145 mg, 0.49 mmol), (5-methoxypyridin-2-yl)methanol (74 mg, 0.54 mmol) and CMBP (141 mg, 0.58 mmol) in toluene (5 mL) in a sealed tube was stirred at 100° C. for 3 hours. The reaction was cooled to rt, and the solvent was removed in vacuo and the residue purified by low pH prep HPLC followed by column chromatography (silica, eluting with 20-100% EtOAc in heptane) to give the title compound.

$^1$H NMR (250 MHz, 353K, DMSO-A) δ 8.25 (t, J=2.4 Hz, 2H), 7.75 (dd, J=8.5, 2.4 Hz, 1H), 7.49-7.34 (m, 2H), 7.08 (d, J=9.1 Hz, 1H), 6.92-6.81 (m, 3H), 5.07 (s, 2H), 4.87 (d, J=17.3 Hz, 1H), 4.52 (m, 1H), 4.36 (d, J=17.3 Hz, 1H), 3.93 (s, 3H), 3.84 (s, 3H), 3.01 (m, 1H), 2.59 (m, 1H), 1.12 (d, J=6.7 Hz, 3H). Tr (METCR1600)=4.26 min m/z (ES$^+$) (M+H)$^+$ 420.2.

Method 32

Scheme for Method 32

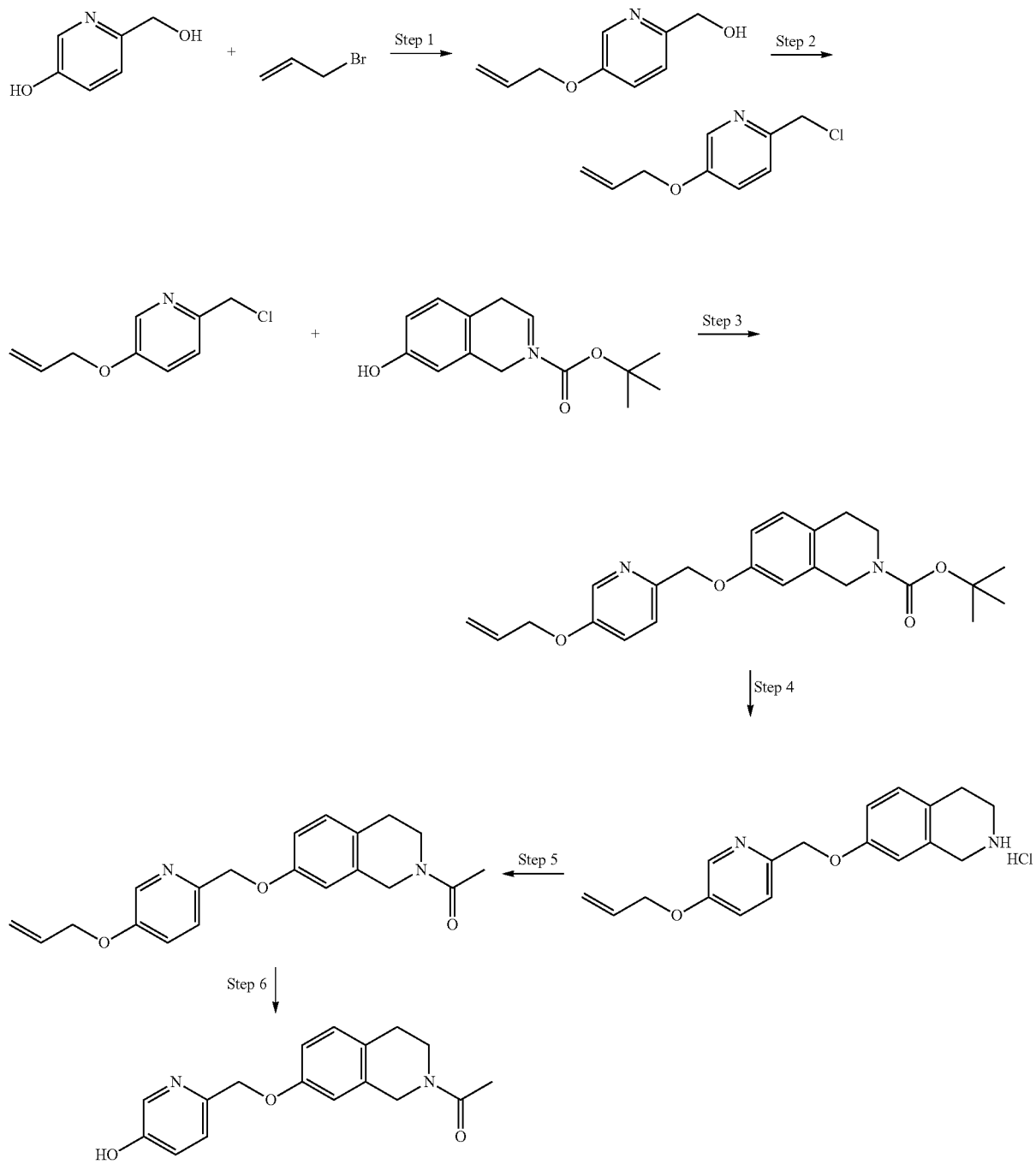

Example 32: 1-{7-[(5-Hydroxypyridin-2-yl)methoxy]-1,2,3,4-tetrahydroisoquinolin-2-yl}ethan-1-one (5-Allyloxy-2-pyridyl)methanol 6-(Hydroxymethyl)pyridin-3-ol (5.0 g, 40 mmol) was suspended in acetone (80 mL) and an aqueous solution of potassium carbonate (7.7 g, 56 mmol) in 10 mL of water was added. The reaction mixture was heated to 60° C. for 1 hour and 3-bromoprop-1-ene (4.3 mL, 50 mmol) in acetone (20 mL) was added drop-wise over 30 minutes via dropping funnel and the reaction heated at 60° C. for a further 2 hours. The solution was allowed to cool to rt and the pH adjusted to 7 with 6 M HCl. The volatiles were removed under reduced pressure and the resulting solution partitioned between EtOAc (50 mL) and water (20 mL). The aqueous layer was extracted with EtOAc (2×20 mL). The combined organics were separated, dried over MgSO$_4$ and concentrated under reduced pressure to afford the title compound. $^1$H NMR (250 MHz, Chloroform-d) δ 8.26 (d, J=2.6 Hz, 1H), 7.25-7.20 (m, 1H), 7.17 (d, J=8.5 Hz, 1H), 6.04 (ddt, J=17.2, 10.5, 5.3 Hz, 1H), 5.53-5.24 (m, 2H), 4.70 (s, 2H), 4.59 (dt, J=5.3, 1.4 Hz, 2H), 3.32 (s, 1H). Tr (METCR0990)= 1.29 min, (ES$^+$) (M+H)$^+$ 166.2, 100%.

5-Allyloxy-2-(chloromethyl)pyridine

To a solution of (5-allyloxy-2-pyridyl)methanol (0.50 g, 3.0 mmol) in DCM (40 mL) at 0° C. was added thionyl chloride (0.44 mL, 6.1 mmol) and the reaction mixture was stirred at rt under a nitrogen atmosphere for 2.5 hours. The reaction mixture was concentrated under reduced pressure and the residue was co-distilled with DCM (3×20 mL) to give the title compound, which was used immediately in the next step with no analysis taken.

tert-Butyl 7-[(5-allyloxy-2-pyridyl)methoxy]-3,4-dihydro-1H-isoquinoline-2-carboxylate tert-Butyl 7-hydroxy-3,4-dihydro-1H-isoquinoline-2-carboxylate (0.80 g, 3.2 mmol), KI (0.24 g, 1.5 mmol) and Cs$_2$CO$_3$ (2.1 g, 6.4 mmol) were dissolved in DML (20 mL) and the reaction mixture stirred at rt for 15 minutes. 5-Allyloxy-2-(chloromethyl)pyridine (549-4) (0.59 g, 3.2 mmol) was added and the reaction mixture stirred overnight at rt. DML was removed under reduced pressure and water (20 mL) was added to the reaction mixture and extracted with EtOAc (3×20 mL). The combined organic layers were washed with brine (20 mL) and dried over Na$_2$SO$_4$, filtered and concentrated to give the crude product. The product was purified by column chromatography (silica, eluting with 0-20% EtOAc in heptane) to give the title compound. $^1$H NMR (500 MHz, DMSO-J6) δ 8.30-8.27 (m, 1H), 7.45-7.40 (m, 2H), 7.05 (d, J=8.4 Hz, 1H), 6.86-6.79 (m, 2H), 6.09-5.99 (m, 1H), 5.44-5.38 (m, 1H), 5.28 (dd, J=10.5, 1.4 Hz, 1H), 5.06 (s, 2H), 4.67-4.63 (m, 2H), 4.44 (s, 2H), 3.51 (t, J=5.9 Hz, 2H), 2.68 (t, J=5.8 Hz, 2H), 1.42 (s, 9H).

7-[(5-Allyloxy-2-pyridyl)methoxy]-1,2,3,4-tetrahydroisoquinoline hydrochloride tert-Butyl 7-[(5-allyloxy-2-pyridyl)methoxy]-3,4-dihydro-1H-isoquinoline-2-carboxylate (0.30 g, 0.76 mmol) was suspended in 4 M HCl in dioxane (17 mL, 68 mmol), sonicated and then stirred at rt for 2 hours. The reaction mixture was concentrated under reduced pressure to give the title compound. $^1$H NMR (500 MHz, DMSO-d6) δ 9.30 (s, 2H), 8.34 (d, J=2.1 Hz, 1H), 7.57-7.48 (m, 2H), 7.14 (d, J=8.4 Hz, 1H), 6.96-6.86 (m, 2H), 6.04 (ddt, J=17.2, 10.5, 5.3 Hz, 1H), 5.46-5.36 (m, 1H), 5.30 (dd, J=10.6, 1.5 Hz, 1H), 5.12 (s, 2H), 4.71-4.66 (m, 2H), 4.20 (t, J=4.6 Hz, 2H), 3.36-3.30 (m, 2H), 2.92 (t, J=6.2 Hz, 2H).

1-[7-[(5-Allyloxy-2-pyridyl)methoxy]-3,4-dihydro-1H-isoquinolin-2-yl]ethanone Acetic acid (0.054 g, 0.90 mmol) and HATU (0.34 mg, 0.90 mmol) were dissolved in DMF (25 mL) and DIPEA (0.24 mL, 1.4 mmol) was added. 7-[(5-Allyloxy-2-pyridyl)methoxy]-1,2,3,4-tetrahydroisoquinoline hydrochloride (0.30 g, 0.90 mmol) was suspended in DMF (25 mL). DIPEA (0.24 mL, 1.4 mmol) was added and the reaction was stirred at rt for 6 hours. The solvent was removed under reduced pressure and the residue dissolved in water (20 mL) and extracted into DCM (3×25 mL). The organic layers were combined, dried over MgSO$_4$ and concentrated in vacuo. The residue was purified by column chromatography (silica, eluting with 0-10% MeOH in DCM) followed by further column chromatography purification (silica, eluting with 50-100% EtOAc in heptane) to give the title compound. $^1$H NMR (500 MHz, DMSO-d$_6$) δ 8.31-8.25 (m, 1H), 7.47-7.39 (m, 2H), 7.07 (d, J=8.3 Hz, 1H), 6.87-6.80 (m, 2H), 6.10-5.98 (m, 1H), 5.46-5.38 (m, 1H), 5.29 (d, J=10.5 Hz, 1H), 5.09-5.04 (m, 2H), 4.65 (d, J=4.5 Hz, 2H), 4.56 (d, J=23.8 Hz, 2H), 3.61 (t, J=5.9 Hz, 2H), 2.81-2.63 (m, 2H), 2.14-1.97 (m, 3H).

1-{7-[(5-Hydroxypyridin-2-yl)methoxy]-1,2,3,4-tetrahydroisoquinolin-2-yl}ethan-1-one A solution of 1-[7-[(5-allyloxy-2-pyridyl)methoxy]-3,4-dihydro-1H-isoquinolin-2-yl]ethanone (549-9) (0.20 g, 0.59 mmol) in DMF (20 mL) was de-gassed for 10 minutes. 1,3-Dimethylbarbituric acid (0.19 g, 1.2 mmol) and Pd(PPh$_3$)$_4$ (48 mg, 0.041 mmol) were added and the reaction mixture stirred at rt for 3 hours. The reaction mixture was concentrated under reduced pressure and the product purified by column chromatography (silica, eluting with 50-100% EtOAc in heptane, followed by 0-5% MeOH in DCM). The resultant material was further purified by high pH prep HPLC followed by column chromatography (silica, eluting with 0-5% MeOH in DCM) to give the title compound.
$^1$H NMR (250 MHz, 353 K, DMSO-d$_6$) δ 8.12 (d, J=2.8 Hz, 1H), 7.32 (d, J=8.5 Hz, 1H), 7.17 (dd, J=8.4, 2.8 Hz, 1H), 7.07 (d, J=8.3 Hz, 1H), 6.88-6.76 (m, 2H), 5.02 (s, 2H), 4.56 (s, 2H), 3.64 (t, J=6.0 Hz, 2H), 2.82-2.71 (m, 2H), 2.07 (s, 3H). Tr (MET-uHPLC-AB-101)=1.59 min, (ES$^+$) (M+H)$^+$ 299.1.

Method 33

Scheme for Method 33

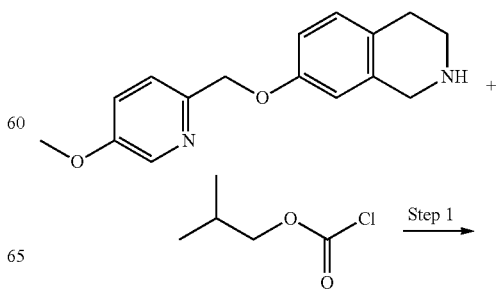

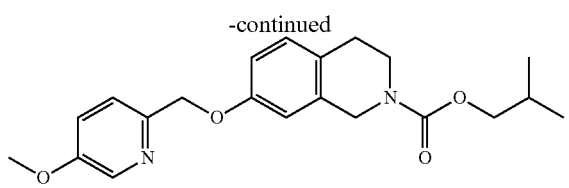
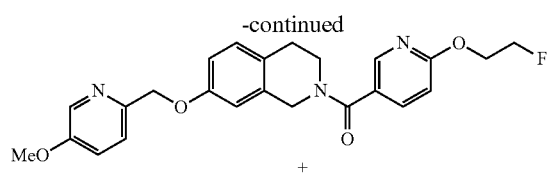

Example 33: 2-Methylpropyl 7-[(5-methoxypyridin-2-yl)methoxy]-1,2,3,4-tetrahydroisoquinoline-2-carboxylate To a solution of 7-[(5-methoxy-2-pyridyl)methoxy]-1,2,3,4-tetrahydroisoquinoline; hydrochloride (100 mg, 0.33 mmol, as prepared by method 1) in DCM (10 mL) was added DIPEA (0.16 mL, 0.98 mmol) followed by 2-methylpropyl carbonochloridate (47 µL, 0.36 mmol) under a nitrogen atmosphere. The reaction was stirred at rt for 1 hour. The reaction mixture was diluted with DCM (10 mL) and washed with 1 M HCl (20 mL). The organic layer was dried over $Na_2SO_4$, filtered and concentrated in vacuo. The residue was purified by basic prep HPLC to give the title compound.

$^1$H NMR (250 MHz, 353 K, DMSO-$d_6$) δ 8.45-8.04 (m, 1H), 7.72-7.25 (m, 2H), 7.07 (d, J=8.1 Hz, 1H), 6.93-6.57 (m, 2H), 5.08 (s, 2H), 4.51 (s, 2H), 4.07-3.72 (m, 5H), 3.60 (t, J=6.0 Hz, 2H), 2.74 (t, J=6.0 Hz, 2H), 2.11-1.75 (m, 1H), 0.92 (d, J=6.7 Hz, 6H). Tr (MET-uHPLC-AB-101)=3.70 min, (ES$^+$) (M+H)$^+$ 371.

Method 34

Scheme for Method 34

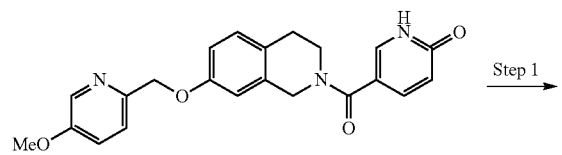

Example 34: (6-(2-Fluoroethoxy)pyridin-3-yl)(7-((5-methoxypyridin-2-yl)methoxy)-3,4-dihydroisoquinolin-2(1H)-yl)methanone A mixture of 5-(7-((5-methoxypyridin-2-yl)methoxy)-1,2,3,4-tetrahydroisoquinoline-2-carbonyl)pyridin-2(1H)-one (0.200 g, 0.511 mmol, prepared by method 1), 1-bromo-2-fluoroethane (0.078 g, 0.61 mmol), potassium carbonate (0.706 g, 5.11 mmol) and N,N-dimethylformamide (30.0 mL) was stirred at ambient temperature for 16 h. After this time, ethyl acetate (20 mL) was added, and the mixture was washed with water (3×20 mL). The organic layer was dried over sodium sulfate, filtered, and the filtrate was concentrated in vacuo. The residue obtained was purified by chromatography (silica gel; dichloromethane to 95:5 dichloromethane/methanol; gradient elution) to give the title compound.

$^1$H NMR (500 MHz, DMSO-$d_6$) δ 8.30-8.27 (m, 2H), 7.84 (dd, J=8.5, 2.0 Hz, 1H), 7.42 (br s, 2H), 7.08 (d, J=8.5 Hz, 1H), 6.96-6.83 (m, 3H), 5.06 (br s, 2H), 4.82-4.81 (m, 1H), 4.73-4.59 (m, 4H), 4.54 (t, J=4.0 Hz, 1H), 3.83-3.60 (m, 5H), 2.79 (t, J=6.0 Hz, 2H); $^{19}$F NMR (282 MHz, DMSO-$d_6$) δ -222.7; Tr (MET-AMRI001)=12.83 min, (ESI) m/z 438 [M+H]$^+$.

The following compound was similarly prepared:

| Example | Structure | Mol. Weight | LCMS data |
|---|---|---|---|
| 34.1 | 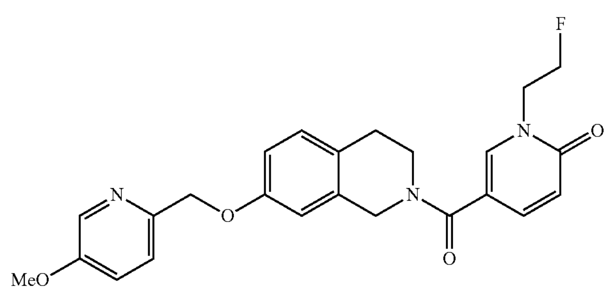 [SMILES: COc1ccc(COc2ccc3c(c2)CN(C(=O)c2ccc(=O)n(CCF)c2)CC3)nc1] | 437.47 | Tr (MET-AMRI001) = 11.13 min m/z (ES$^+$) (M + H)$^+$ 438 |

Method 35
Scheme for Method 35

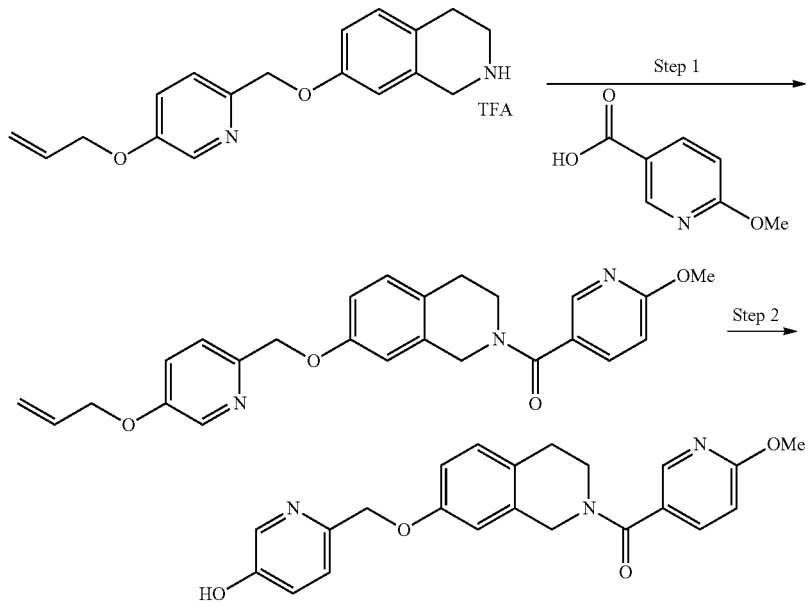

Example 35: (7-((5-(Allyloxy)pyridin-2-yl)methoxy)-3,4-dihydroisoquinolin-2(1H)-yl)(6-methoxypyridin-3-yl)methanone A mixture of 7-((5-(allyloxy)pyridin-2-yl)methoxy)-1,2,3,4-tetrahydroisoquinoline trifluoroacetate (0.172 g, 0.580 mmol, prepared by method 40) and 6-methoxynicotinic acid (0.089 g, 0.58 mmol) in dichloromethane (8.7 mL) was cooled to 0° C. and treated with pyridine (0.234 mL, 2.90 mmol) and 1-(3-dimethylaminopropyl)-3-ethylcarbodiimide hydrochloride (0.167 g, 0.871 mmol). The mixture was stirred at 0° C. for 10 min and at rt for 1 h. After this time, the mixture was concentrated in vacuo. The residue obtained was purified by chromatography (silica gel; dichloromethane to 95:5 dichloromethane/methanol; gradient elution) to give the title compound: $^1$H NMR (300 MHz, DMSO-$d_6$) δ 8.32 (d, J=1.8 Hz, 1H), 8.29 (s, 1H), 7.82 (dd, J=8.7, 2.4 Hz, 1H), 7.43 (br s, 2H), 7.09 (d, J=8.4 Hz, 1H), 6.92-6.83 (m, 3H), 6.11-5.98 (m, 1H), 5.41 (dd, J=17.1, 1.5 Hz, 1H), 5.29 (dd, J=10.5, 1.5 Hz, 1H), 5.05 (br s, 2H), 4.66-4.65 (m, 4H), 3.91 (s, 3H), 3.80-3.60 (m, 2H), 2.79 (t, J=5.7 Hz, 2H); $T_r$ (MET-AMRI001)=13.52 min, (ESI) m/z 432 [M+H]$^+$.

Example 35.1: (7-((5-Hydroxypyridin-2-yl)methoxy)-3,4-dihydroisoquinolin-2(1H)-yl)(6-methoxypyridin-3-yl)methanone 1,3-Dimethylbarbituric acid (0.124 g, 0.797 mmol) and tetrakis(triphenylphosphine)-palladium(0) (0.023 g, 0.020 mmol) were added to a solution of (7-((5-(allyloxy)pyridin-2-yl)methoxy)-3,4-dihydroisoquinolin-2(1H)-yl)(6-methoxypyridin-3-yl)methanone (0.172 g, 0.399 mmol) in methanol (14.4 mL), and the mixture was stirred at rt for 4.5 h. After this time, the mixture was concentrated in vacuo. The residue obtained was combined with dichloromethane (20 mL) and saturated aqueous sodium bicarbonate (20 mL). The layers were separated, and the aqueous layer was extracted with dichloromethane (2×30 mL). The combined organic layers were dried over sodium sulfate, filtered, and the filtrate was concentrated in vacuo. The residue obtained was purified by chromatography (silica gel; dichloromethane to 95:5 dichloromethane/methanol; gradient elution). The product was lyophilized from acetonitrile (5 mL) and water (5 mL) to give the title compound.

$^1$H NMR (500 MHz, DMSO-$d_6$) δ 9.92 (s, 1H), 8.31 (d, J=2.0 Hz, 1H), 8.10 (br s, 1H), 7.81 (dd, J=8.5, 2.0 Hz, 1H), 7.31 (br s, 1H), 7.17 (d, J=6.5 Hz, 1H), 7.08 (d, J=8.0 Hz, 1H), 6.90-6.82 (m, 3H), 5.00 (br s, 2H), 4.67 (br s, 2H), 3.91 (s, 3H), 3.76-3.60 (m, 2H), 2.79 (t, J=5.5 Hz, 2H); $T_r$ (MET-AMRI-001)=11.62 min, (ESI) m/z 392 [M+H]$^+$.

Method 36
Scheme for Method 36

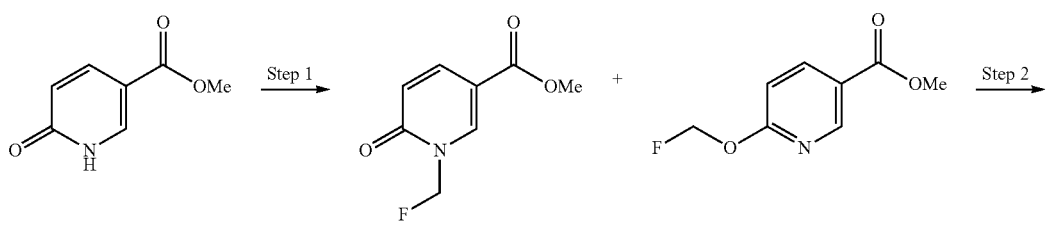

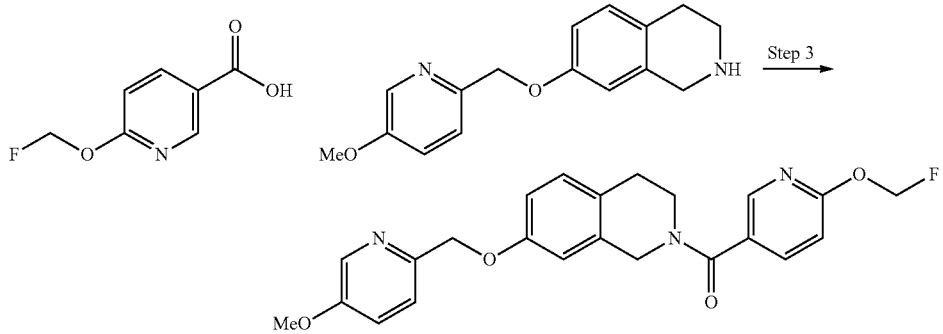

Example 36: (6-(Fluoromethoxy)pyridin-3-yl)(7-((5-methoxypyridin-2-yl)methoxy)-3,4-dihydroisoquinolin-2(1H)-yl)methanone Methyl 6-(fluoromethoxy)nicotinate A mixture of methyl 6-oxo-1,6-dihydropyridine-3-carboxylate (0.200 g, 1.30 mmol), fluoromethyl 4-methylbenzenesulfonate (0.400 g, 1.96 mmol) and potassium carbonate (1.81 g, 13.1 mmol) in N,N-dimethylformamide (4.9 mL) was stirred at 50° C. for 16 h. After this time, ethyl acetate (20 mL) was added, and the mixture was washed with water (3×20 mL). The organic layer was dried over sodium sulfate, filtered, and the filtrate was concentrated in vacuo. The residue obtained was purified by chromatography (silica gel; dichloromethane to 95:5 dichloromethane/methanol; gradient elution) to give the title compound: $^1$H NMR (300 MHz, DMSO-d$_6$) δ 8.81 (dd, J=2.4, 0.6 Hz, 1H), 8.32 (dd, J=8.4, 2.4 Hz, 1H), 7.13 (dd, J=8.4, 0.6 Hz, 1H), 6.15 (d, J=52.2 Hz, 2H), 3.87 (s, 3H).

6-(Fluoromethoxy)nicotinic acid

A solution of methyl 6-(fluoromethoxy)nicotinate (0.082 g, 0.44 mmol) in tetrahydrofuran (3.7 mL) was treated with a solution of lithium hydroxide monohydrate (0.019 g, 0.44 mmol) in water (3.7 mL), and the mixture was stirred at ambient temperature for 1 h. After this time, the volatiles were removed in vacuo, and water (40 mL) was added. The aqueous mixture was washed with dichloromethane (3×75 mL), and the pH adjusted to 3 with 2.0 N hydrochloric acid, added dropwise. The solid that formed was collected by filtration, washed with water (20 mL) and dried in vacuo to afford a first crop of the title compound, 0.031 g (41%). The filtrate was extracted with dichloromethane (3×10 mL), and the combined organic layers were concentrated in vacuo to afford a second crop of the title compound: $^1$H NMR (300 MHz, DMSO-d$_6$) δ 13.30 (br s, 1H), 8.78-8.77 (m, 1H), 8.28 (dd, J=8.4, 2.4 Hz, 1H), 7.11-7.08 (m, 1H), 6.14 (d, J=52.2 Hz, 2H).

(6-(Fluoromethoxy)pyridin-3-yl)(7-((5-methoxypyridin-2-yl)methoxy)-3,4-dihydroisoquinolin-2(1H)-yl)methanone Pyridine (0.060 mL, 0.74 mmol) and 1-(3-dimethylaminopropyl)-3-ethylcarbodiimide hydrochloride (0.043 g, 0.22 mmol) were added to a mixture of 7-((5-methoxypyridin-2-yl)methoxy)-1,2,3,4-tetrahydroisoquinoline (0.040 g, 0.15 mmol, prepared by Method 1) and 6-(fluoromethoxy)-nicotinic acid (0.035 g, 0.21 mmol) in dichloromethane (4.0 mL) at 0° C., and the mixture was stirred at 0° C. for 10 minutes and at ambient temperature for 16 h. After this time, the solvent was removed in vacuo. The residue obtained was purified by chromatography (silica gel; dichloromethane to 95:5 dichloromethane/methanol; gradient elution) to give the title compound.

$^1$H NMR (300 MHz, DMSO-d$_6$) δ 8.38 (d, J=1.8 Hz, 1H), 8.28 (s, 1H), 7.96 (d, J=8.4 Hz, 1H), 7.42 (br s, 2H), 7.10-7.07 (m, 2H), 6.96-6.83 (m, 2H), 6.13 (d, J=52.5 Hz, 2H), 5.08 (br s, 2H), 4.72-4.61 (m, 2H), 3.83-3.57 (m, 5H), 2.79 (br s, 2H); $^{19}$F NMR (282 MHz, DMSO-d$_6$) δ −154.7; T$_r$ (MET-AMRI001)=12.91 min, (ESI) m/z 424 [M+H]$^+$.

Method 37

Scheme for Method 37

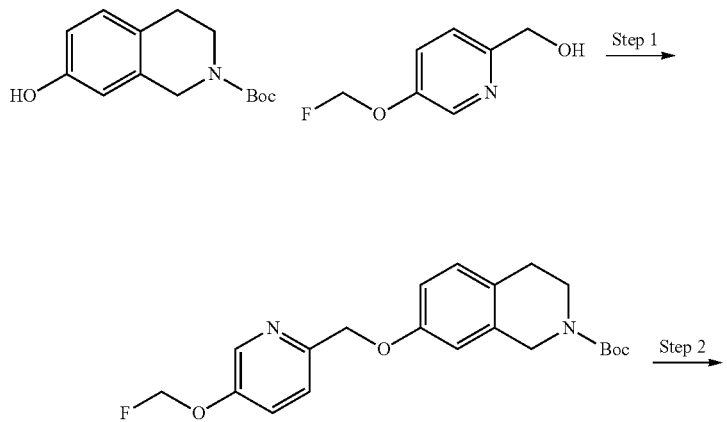

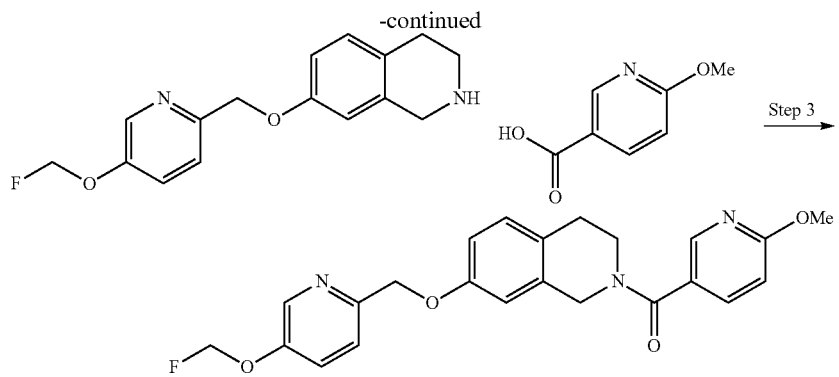

Example 37: (7-((5-(Fluoromethoxy)pyridin-2-yl)methoxy)-3,4-dihydroisoquino-lin-2(1H)-yl)(6-methoxypyridin-3-yl)methanone tert-Butyl 7-((5-(fluoromethoxy)pyridin-2-yl)methoxy)-3,4-dihydro-isoquinoline-2(1H)-carboxylate A mixture of tert-butyl 7-hydroxy-3,4-dihydroisoquinoline-2(1H)-carboxylate (0.136 g, 0.547 mmol), (5-(fluoromethoxy)pyridin-2-yl)methanol (0.043 g, 0.28 mmol) and toluene (5.8 mL) was treated with (tributylphosphoranylidene)acetonitrile (0.165 g, 0.684 mmol), and the mixture was heated at 100° C. for 16 h. After this time, the solvent was removed in vacuo, and the residue obtained was purified by chromatography (silica gel; dichloro-methane to 95:5 dichloromethane/methanol; gradient elution) to give the title compound: $^1$H NMR (300 MHz, DMSO-$d_6$) δ 8.42 (d, J=3.0 Hz, 1H), 7.62 (dd, J=8.4, 2.7 Hz, 1H), 7.52 (d, J=8.4 Hz, 1H), 7.06 (d, J=8.1 Hz, 1H), 6.86-6.80 (m, 2H), 5.93 (d, J=53.7 Hz, 2H), 5.11 (s, 2H), 4.45 (s, 2H), 3.52 (t, J=6.0 Hz, 2H), 2.68 (t, J=6.0 Hz, 2H), 1.42 (s, 9H).

7-((5-(Fluoromethoxy)pyridin-2-yl)methoxy)-1,2,3,4-tetrahydroiso-quinoline

A solution of tert-butyl 7-((5-(fluoromethoxy)pyridin-2-yl)methoxy)-3,4-dihydroisoquin-oline-2(1H)-carboxylate (0.037 g, 0.095 mmol) in dichloromethane (0.3 mL) was treated with trifluoroacetic acid (0.37 mL, 4.9 mmol), and the mixture was stirred at rt for 3 h. After this time, the solvent was removed in vacuo, and the residue obtained was dissolved in dichloromethane (10 mL) and washed with saturated aqueous sodium bicarbonate (20 mL). The aqueous layer was extracted with dichloromethane (10 mL). The combined organic layers were dried over sodium sulfate, filtered, and the filtrate was concentrated in vacuo to give the title compound, which was taked directly to the next step.

(7-((5-(Fluoromethoxy)pyridin-2-yl)methoxy)-3,4-dihydroisoquino-lin-2(1H)-yl)(6-methoxypyridin-3-yl)methanone Pyridine (0.038 mL, 5.3 mmol) and 1-(3-dimethylaminopropyl)-3-ethylcarbodiimide hydrochloride (0.027 g, 0.14 mmol) were added to a mixture of 7-((5-(fluoromethoxy)-pyridin-2-yl)methoxy)-1,2,3,4-tetrahydroisoquinoline (0.027 g, 0.094 mmol) and 6-methoxynicotinic acid (0.020 g, 0.13 mmol) in dichloromethane (2.5 mL) at 0° C., and the mixture was stirred at 0° C. for 10 minutes and at ambient temperature for 16 h. After this time, the solvent was removed in vacuo. The residue obtained was purified by chromatography (silica gel; dichloromethane to 95:5 dichloromethane/methanol; gradient elution) to give the title compound.

$^1$H NMR (500 MHz, DMSO-$d_6$) δ 8.41 (s, 1H), 8.31 (d, J=2.0 Hz, 1H), 7.81 (dd, J=8.5, 2.0 Hz, 1H), 7.61 (d, J=6.5 Hz, 1H), 7.53 (br s, 1H), 7.09 (d, J=8.5 Hz, 1H), 6.94-6.84 (m, 3H), 5.92 (d, J=53.5 Hz, 2H), 5.11 (br s, 2H), 4.68 (br s, 2H), 3.91-3.59 (m, 5H), 2.79 (t, J=5.5 Hz, 2H); $^{19}$F NMR (282 MHz, DMSO-$d_6$) δ −151.4; $T_r$ (MET-AMRI001)= 13.93 min, MS (ESI) m/z 424 [M+H]$^+$.

Method 38

Scheme for Method 38

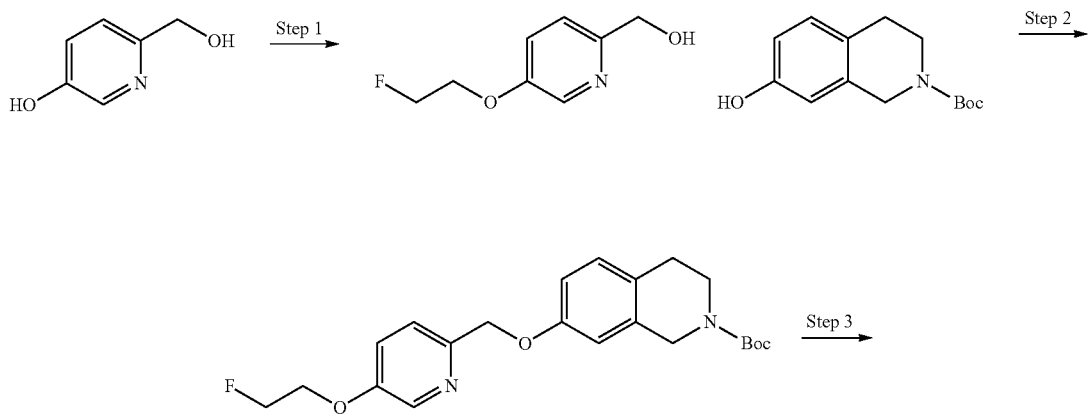

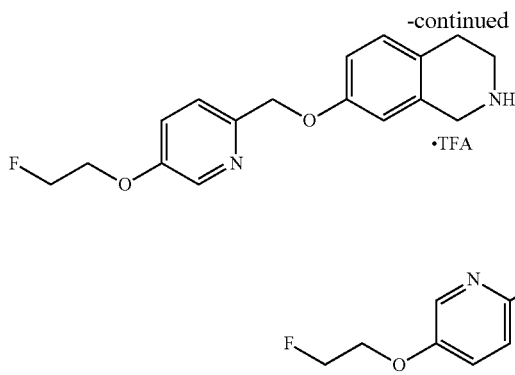
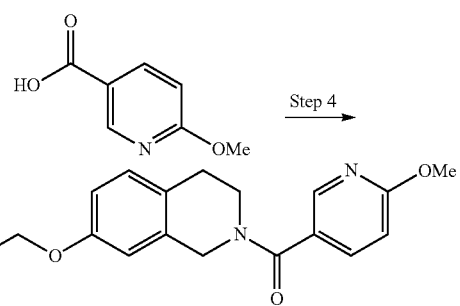

Example 38: (7-((5-(2-Fluoroethoxy)pyridin-2-yl)methoxy)-3,4-dihydroisoquino-lin-2(1H)-yl)(6-methoxypyridin-3-yl)methanone (5-(2-Fluoroethoxy)pyridin-2-yl)methanol A mixture of 6-(hydroxymethyl)pyridin-3-ol (0.250 g, 2.00 mmol), 1-bromo-2-fluoro-ethane (0.304 g, 2.40 mmol), potassium carbonate (2.76 g, 20.0 mmol) and N,N-dimethylformamide (15.6 mL) was stirred at ambient temperature for 16 h. After this time, ethyl acetate (20 mL) was added, and the mixture was washed with water (3×20 mL). The organic layer was dried over sodium sulfate, filtered, and the filtrate was concentrated in vacuo. The residue obtained was purified by chromatography (silica gel; dichloromethane to 95:5 dichloromethane/methanol; gradient elution) to give the title compound: $^1$H NMR (300 MHz, DMSO-$d_6$) δ 8.22 (d, J=2.1 Hz, 1H), 7.45-7.37 (m, 2H), 5.31 (t, J=6.0 Hz, 1H), 4.86-4.82 (m, 1H), 4.69-4.66 (m, 1H), 4.49 (d, J=5.7 Hz, 2H), 4.37-4.34 (m, 1H), 4.27-4.24 (m, 1H).

tert-Butyl 7-((5-(2-Fluoroethoxy)pyridin-2-yl)methoxy)-3,4-dihydro-isoquinoline-2(1H)-carboxylate A mixture of butyl 7-hydroxy-3,4-dihydroisoquinoline-2(1H)-carboxylate (0.318 g, 1.27 mmol) and (5-(2-fluoroethoxy)pyridin-2-yl)methanol (0.109 g, 0.637 mmol) in toluene (22.2 mL) was treated with (tributylphosphoranylidene)acetonitrile (0.384 g, 1.59 mmol), and the mixture was heated at 100° C. for 3 h. After this time, the mixture was concentrated in vacuo. The residue obtained was purified by chromatography (silica gel; dichloromethane to 95:5 dichloromethane/methanol; gradient elution) to give the title compound: $^1$H NMR (300 MHz, DMSO-$d_6$) δ 8.32 (s, 1H), 7.45 (d, J=1.5 Hz, 2H), 7.06 (d, J=8.4 Hz, 1H), 6.84-6.81 (m, 2H), 5.07 (s, 2H), 4.84 (t, J=3.9 Hz, 1H), 4.68 (t, J=3.9 Hz, 1H), 4.48-4.37 (m, 3H), 4.28 (t, J=3.9 Hz, 1H), 3.52 (t, J=5.7 Hz, 2H), 2.68 (t, J=5.4 Hz, 2H), 1.42 (s, 9H).

7-((5-(2-Fluoroethoxy)pyridin-2-yl)methoxy)-1,2,3,4-tetrahydroiso-quinoline trifluoroacetate A mixture of tert-butyl 7-((5-(2-fluoroethoxy)pyridin-2-yl)methoxy)-3,4-dihydroisoquin-oline-2(1H)-carboxylate (0.135 g, 0.335 mmol) in methylene chloride (1.3 mL) was treated with trifluoroacetic acid (1.31 mL, 17.1 mmol), and the mixture was stirred at ambient temperature for 1 h. After this time, the mixture was concentrated in vacuo to give the title compound: MS (ESI) m/z 303 [M+H]$^+$.

(7-((5-(2-Fluoroethoxy)pyridin-2-yl)methoxy)-3,4-dihydroisoquino-lin-2(1H)-yl)(6-methoxypyridin-3-yl)methanone Pyridine (0.133 mL, 1.65 mmol) and 1-(3-dimethylaminopropyl)-3-ethylcarbodiimide hydrochloride (0.095 g, 0.50 mmol) were added to a mixture of 7-((5-(2-fluoroethoxy)-pyridin-2-yl)methoxy)-1,2,3,4-tetrahydroisoquinoline trifluoroacetate (0.100 g, 0.240 mmol) and 6-methoxynicotinic acid (0.051 g, 0.33 mmol) in dichloromethane (5.0 mL) at 0° C., and the mixture was stirred at 0° C. for 10 minutes and at ambient temperature for 16 h. After this time, the mixture was concentrated in vacuo. The residue obtained was purified by chromatography (silica gel; dichloromethane to 95:5 methylene chloride/methanol; gradient elution). The product was lyophilized from acetonitrile (5 mL) and water (5 mL) to give the title compound.

$^1$H NMR (500 MHz, DMSO-$d_6$) δ 8.31 (d, J=1.5 Hz, 2H), 7.81 (dd, J=8.5, 2.0 Hz, 1H), 7.45 (s, 2H), 7.08 (d, J=8.5 Hz, 1H), 6.93-6.83 (m, 3H), 5.07 (br s, 2H), 4.80 (t, J=4.0 Hz, 1H), 4.72-4.67 (m, 3H), 4.36 (t, J=4.0 Hz, 1H), 4.30 (t, J=4.0 Hz, 1H), 4.29 (s, 3H), 3.91-3.60 (m, 2H), 2.79 (t, J=5.5 Hz, 2H); $^{19}$F NMR (282 MHz, DMSO-$d_6$) δ −222.3; $T_r$ (MET-AMRI001)=12.87 min, MS (ESI) m/z 438 [M+H]$^+$.

Method 39

Scheme for Method 39

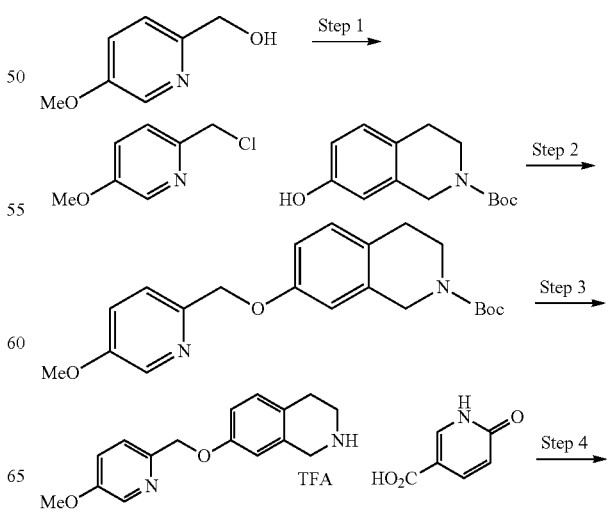

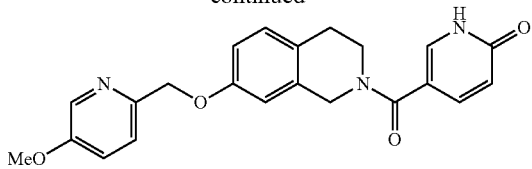

Example 39: 5-(7-((5-Methoxypyridin-2-yl)methoxy)-1,2,3,4-tetrahydroisoquinoline-2-carbonyl)pyridin-2(1H)-one

2-(Chloromethyl)-5-methoxypyridine

A solution of (5-methoxypyridin-2-yl)methanol (0.100 g, 0.719 mmol) in dichloromethane (5.0 mL) at 0° C. was treated with thionyl chloride (0.105 mL, 1.44 mmol), and the mixture was stirred at 0° C. for 1 h. After this time, the solution was poured into water (10 mL). The layers were separated, and the aqueous layer was extracted with dichloromethane (2×25 mL). The organic layers were combined, dried over sodium sulfate, filtered and the filtrate was concentrated in vacuo to give the title compound: $^1$H NMR (300 MHz, CDCl$_3$) δ 8.28-8.27 (m, 1H), 7.38 (d, J=8.7 Hz, 1H), 7.21 (dd, J=8.7, 3.0 Hz, 1H), 4.65 (s, 2H), 3.87 (s, 3H).

tert-Butyl 7-((5-methoxypyridin-2-yl)methoxy)-3,4-dihydroisoquino-line-2(1H)-carboxylate A solution of tert-butyl 7-hydroxy-3,4-dihydroisoquinoline-2(1H)-carboxylate (0.830 g, 3.33 mmol) in N,N-dimethylformamide (24.2 mL) was treated with cesium carbonate (5.42 g, 16.6 mmol), 2-(chloromethyl)-5-methoxypyridine (0.682 g, 4.33 mmol) and potassium iodide (0.055 g, 0.33 mmol), and the mixture was stirred at ambient temperature for 16 h. After this time, the solution was diluted with ethyl acetate (100 mL) and washed with water (3×100 mL). The organic layer was dried over sodium sulfate, filtered, and the filtrate was concentrated in vacuo. The residue obtained was purified by chromatography (silica gel; dichloromethane to 95:5 dichloromethane/methanol; gradient elution) to give the title compound: $^1$H NMR (300 MHz, CDCl$_3$) δ 8.29 (d, J=2.7 Hz, 1H), 7.42 (d, J=8.7 Hz, 1H), 7.22 (dd, J=8.7, 3.0 Hz, 1H), 7.03 (d, J=8.4 Hz, 1H), 6.81 (dd, J=8.4, 2.4 Hz, 1H), 6.72 (d, J=2.4 Hz, 1H), 5.12 (s, 2H), 4.52 (s, 2H), 3.87 (s, 3H), 3.62 (br s, 2H), 2.77-2.74 (m, 2H), 1.49 (s, 9H).

7-((5-Methoxypyridin-2-yl)methoxy)-1,2,3,4-tetrahydroisoquinoline trifluoroacetate A solution of tert-butyl 7-((5-methoxypyridin-2-yl)methoxy)-3,4-dihydroisoquinoline-2(1H)-carboxylate (0.500 g, 1.35 mmol) in dichloromethane (5.3 mL) was treated with trifluoroacetic acid (5.29 mL, 68.7 mmol), and the mixture was stirred at ambient temperature for 1 h. After this time, the solution was concentrated in vacuo to give the title compound, which was used without further purification.

5-(7-((5-Methoxypyridin-2-yl)methoxy)-1,2,3,4-tetrahydroisoquinoline-2-carbonyl)pyridin-2(1H)-one A solution of 7-((5-methoxypyridin-2-yl)methoxy)-1,2,3,4-tetrahydroisoquinoline trifluoroacetate (0.365 g, 1.35 mmol) in dichloromethane (20.3 mL) at 0° C. was treated with 6-oxo-1,6-dihydropyridine-3-carboxylic acid (0.188 g, 1.35 mmol), followed by pyridine (0.544 mL, 6.75 mmol) and 1-(3-dimethylaminopropyl)-3-ethylcarbodiimide hydrochloride (0.388 g, 2.03 mmol). The solution was stirred at 0° C. for 10 minutes and at ambient temperature for 1 hour. After this time, the solution was concentrated in vacuo, and the residue obtained was purified by chromatography (silica gel; dichloromethane to 95:5 dichloromethane/methanol; gradient elution) to give the title compound.

$^1$H NMR (500 MHz, CDCl$_3$) δ 12.22 (br s, 1H), 8.29 (d, J=3.0 Hz, 1H), 7.66 (d, J=2.5 Hz, 1H), 7.61 (dd, J=9.5, 2.5 Hz, 1H), 7.40 (d, J=8.5 Hz, 1H), 7.22 (dd, J=8.0, 2.0 Hz, 1H), 7.07 (d, J=8.5 Hz, 1H), 6.85 (dd, J=8.5, 2.5 Hz, 1H), 6.72 (br s, 1H), 6.61 (d, J=9.5 Hz, 1H), 5.12 (s, 2H), 4.70 (s, 2H), 3.04 (s, 3H), 3.79 (br s, 2H), 2.87 (t, J=5.5 Hz, 2H); T$_r$ (MET-AMRI001)=10.32, (ESI) m/z 392 [M+H]$^+$.

Method 40

Scheme for Method 40

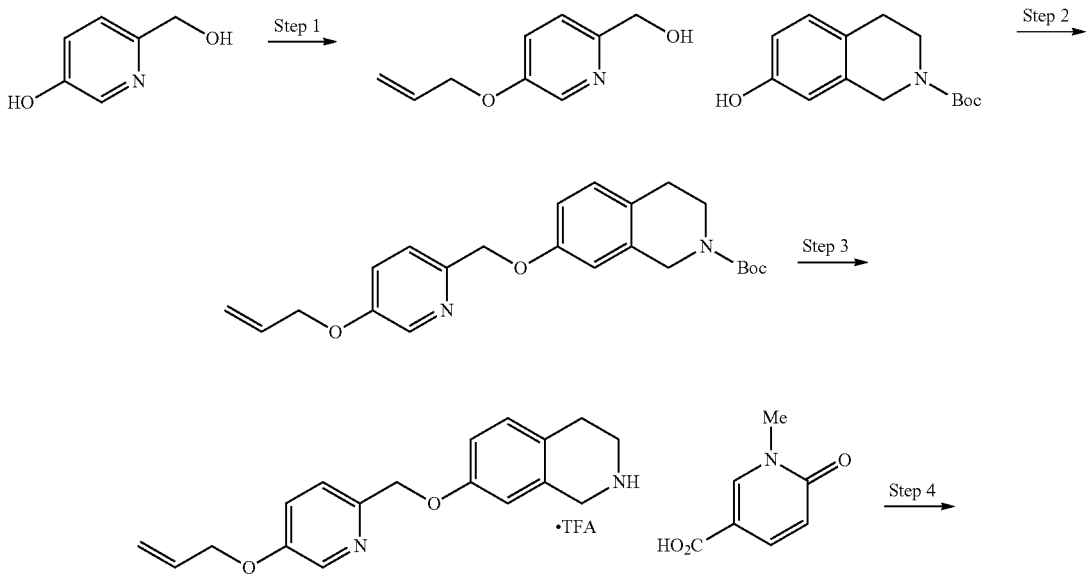

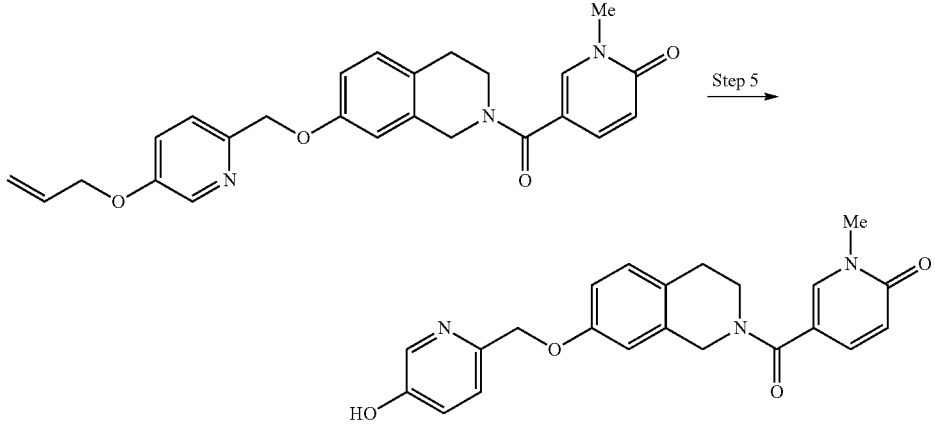

Example 40: 5-(7-((5-Hydroxypyridin-2-yl)methoxy)-1,2,3,4-tetrahydroisoquinoline-2-carbonyl)-1-methylpyridin-2(1H)-one (5-(Allyloxy)pyridin-2-yl)methanol A solution of 6-(hydroxymethyl)pyridin-3-ol (0.100 g, 0.799 mmol) and allyl bromide (0.080 mL, 0.92 mmol) in acetone (3.0 mL) was treated dropwise with a solution of potassium carbonate (0.166 g, 1.19 mmol) in water (3.0 mL), and the solution was heated at 60° C. for 2 h. After this time, the solution was cooled to ambient temperature and extracted with tert-butyl methyl ether (3×40 mL). The combined organic layers were dried over sodium sulfate, filtered, and the filtrate was concentrated in vacuo to give the title compound: $^1$H NMR (300 MHz, CDCl$_3$) δ 8.27 (d, J=2.4 Hz, 1H), 7.25-7.16 (m, 2H), 6.11-5.98 (m, 1H), 5.47-5.45 (m, 1H), 5.41-5.30 (m, 1H), 4.70 (s, 2H), 4.61-4.58 (m, 2H), 3.39 (br s, 1H).

tert-Butyl 7-((5-(allyloxy)pyridin-2-yl)methoxy)-3,4-dihydroisoquino-line-2(1H)-carboxylate A solution of tert-butyl 7-hydroxy-3,4-dihydroisoquinoline-2(1H)-carboxylate (0.815 g, 3.27 mmol) and (5-(allyloxy)pyridin-2-yl)methanol (0.270 g, 1.63 mmol) in toluene (57.0 mL) was treated with (tributylphosphoranylidene)acetonitrile (0.986 g, 4.09 mmol), and the mixture was heated at 100° C. for 3 h. After this time, the solution was concentrated in vacuo, and the residue obtained was purified by chromatography (silica gel; dichloromethane to 95:5 dichloromethane/methanol; gradient elution) to give the title compound: $^1$H NMR (300 MHz, CDCl$_3$) δ 8.30 (d, J=2.7 Hz, 1H), 7.41 (d, J=8.7 Hz, 1H), 7.23 (dd, J=8.4, 2.7 Hz, 1H), 7.03 (d, J=8.4 Hz, 1H), 6.81 (dd, J=8.4, 2.4 Hz, 1H), 6.72 (d, J=2.4 Hz, 1H), 6.11-5.98 (m, 1H), 5.47-5.40 (m, 1H), 5.36-5.31 (m, 1H), 5.12 (s, 2H), 4.59 (dt, J=3.6, 1.5 Hz, 2H), 4.52 (br s, 2H), 3.62 (t, J=5.1 Hz, 2H), 2.75 (t, J=5.7 Hz, 2H), 1.49 (s, 9H).

7-((5-(Allyloxy)pyridin-2-yl)methoxy)-1,2,3,4-tetrahydroisoquinoline trifluoroacetate A solution of tert-butyl 7-((5-(allyloxy)pyridin-2-yl)methoxy)-3,4-dihydroisoquinoline-2(1H)-carboxylate (0.270 g, 0.681 mmol) in dichloromethane (2.7 mL) was treated with trifluoroacetic acid (2.67 mL, 34.7 mmol), and the mixture was stirred at ambient temperature for 1 hour. After this time, the solution was concentrated in vacuo to give the title compound, which was used without further purification.

5-(7-((5-(Allyloxy)pyridin-2-yl)methoxy)-1,2,3,4-tetrahydroisoquino-line-2-carbonyl)-1-methylpyridin-2(1H)-one A solution of 7-((5-(allyloxy)pyridin-2-yl)methoxy)-1,2,3,4-tetrahydroisoquinoline trifluoroacetate (0.177 g, 0.597 mmol) in dichloromethane (9.0 mL) at 0° C. was treated with 1-methyl-6-oxo-1,6-dihydropyridine-3-carboxylic acid (0.091 g, 0.59 mmol) followed by pyridine (0.241 mL, 2.99 mmol) and 1-(3-dimethylaminopropyl)-3-ethylcarbodiimide hydrochloride (0.172 g, 0.896 mmol). The suspension was stirred at 0° C. for 10 minutes and at ambient temperature for 1 h. After this time, the solvent was removed in vacuo, and the residue obtained was purified by chromatography (silica gel; dichloromethane to 95:5 dichloromethane/methanol; gradient elution) to give the title compound: $^1$H NMR (300 MHz, CDCl$_3$) δ 8.31 (d, J=2.7 Hz, 1H), 7.73 (d, J=2.4 Hz, 1H), 7.46-7.39 (m, 2H), 7.23 (dd, J=8.4, 2.7 Hz, 1H), 7.08 (d, J=8.4 Hz, 1H), 6.85 (dd, J=8.4, 2.7 Hz, 1H), 6.72 (br s, 1H), 6.57 (d, J=9.3 Hz, 1H), 6.11-5.98 (m, 1H), 5.47-5.40 (m, 1H), 5.36-5.30 (m, 1H), 5.11 (s, 2H), 4.69 (br s, 2H), 4.59 (dt, J=3.9, 1.5 Hz, 2H), 3.78 (t, J=5.4 Hz, 2H), 3.58 (s, 3H), 2.88 (t, J=6.0 Hz, 2H).

5-(7-((5-Hydroxypyridin-2-yl)methoxy)-1,2,3,4-tetrahydroisoquinoline-2-carbonyl)-1-methylpyridin-2(1H)-one A suspension of 5-(7-((5-(allyloxy)pyridin-2-yl)methoxy)-1,2,3,4-tetrahydroisoquinoline-2-carbonyl)-1-methylpyridin-2(1H)-one (0.225 g, 0.521 mmol) in methanol (18.8 mL) was treated with 1,3-dimethylbarbituric acid (0.163 g, 1.04 mmol) and tetrakis(triphenyl-phosphine)palladium(0) (0.030 g, 0.026 mmol), and the mixture was stirred at ambient temperature for 4.5 h. After this time, the solution was concentrated in vacuo, and the residue obtained was diluted with dichloromethane (20 mL). The solution was washed with saturated aqueous sodium bicarbonate (20 mL), and the aqueous layer was extracted with dichloromethane (2×30 mL). The combined organic solution was dried over sodium sulfate, filtered, and the filtrate was concentrated in vacuo. The residue obtained was purified by chromatography (silica gel; dichloromethane to 95:5 dichloromethane/methanol; gradient elution). The product was lyophilized from acetonitrile (5 mL) and water (5 mL) to give the title compound.

$^1$H NMR (500 MHz, DMSO-$d_6$) δ 9.93 (s, 1H), 8.10 (d, J=2.5 Hz, 1H), 8.04 (d, J=2.5 Hz, 1H), 7.53 (dd, J=9.5, 5.5 Hz, 1H), 7.32 (d, J=8.5 Hz, 1H), 7.17 (dd, J=8.5, 3.0 Hz, 1H), 7.08 (d, J=8.5 Hz, 1H), 6.87 (s, 1H), 6.83 (dd, J=8.5, 3.0 Hz, 1H), 6.41 (d, J=9.5 Hz, 1H), 5.00 (s, 2H), 4.65 (s, 2H), 3.69 (t, J=6.0 Hz, 2H), 3.46 (s, 3H), 2.79 (t, J=5.5 Hz, 2H); $T_r$=(MET-AMRI001)=10.06 min, (ESI) m/z 392 [M+H]$^+$.

Method 41

Scheme for Method 41

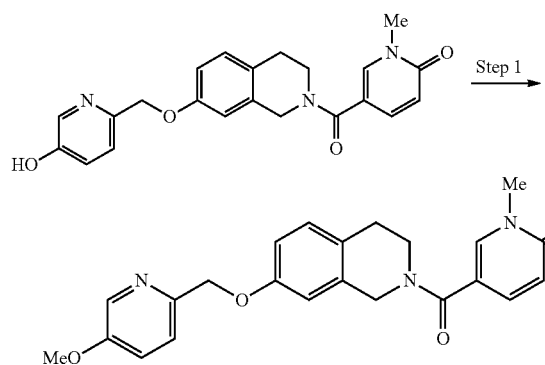

Example 41: 5-(7-((5-Methoxypyridin-2-yl)methoxy)-1,2,3,4-tetrahydroisoquin-oline-2-carbonyl)-1-methylpyridin-2(1H)-one A mixture of 5-(7-((5-hydroxypyridin-2-yl)methoxy)-1,2,3,4-tetrahydroisoquinoline-2-carbonyl)-1-methylpyridin-2(1H)-one (0.094 g, 0.24 mmol, prepared by Method 40) and potassium carbonate (0.332 g, 2.40 mmol) in N,N-dimethylformamide (14.1 mL) was treated with methyl 4-nitrobenzenesulfonate (0.063 g, 0.29 mmol), and the mixture was stirred at ambient temperature for 16 h. After this time, the mixture was diluted with ethyl acetate (20 mL) and washed with water (3×50 mL). The organic layer was dried over sodium sulfate, filtered, and the filtrate was concentrated in vacuo. The residue obtained was purified by chromatography (silica gel; dichloromethane to 95:5 dichloromethane/methanol; gradient elution). The product was lyophilized from acetonitrile (5 mL) and water (5 mL) to give the title compound.

$^1$H NMR (500 MHz, DMSO-$d_6$) δ 8.27 (d, J=2.5 Hz, 1H), 8.04 (d, J=2.5 Hz, 1H), 7.53 (dd, J=9.0, 2.5 Hz, 1H), 7.45-7.40 (m, 2H), 7.08 (d, J=8.5 Hz, 1H), 6.88 (s, 1H), 6.84 (dd, J=8.5, 2.5 Hz, 1H), 6.41 (d, J=9.0 Hz, 1H), 5.06 (s, 2H), 4.65 (s, 2H), 3.83 (s, 3H), 3.69 (t, J=5.5 Hz, 2H), 3.47 (s, 3H), 2.79 (t, J=5.5 Hz, 2H); $T_r$ (MET-AMRI001)=10.53, (ESI) m/z 406 [M+H]$^+$.

Biological Assays

Q46 Radioligand Binding Assay

For radioligand binding assays (RBA) MBP-HTT(1-89) Q46-His(6×) ("Exonl-Q46") protein was generated based on a previous publication (Scherzinger et al. Cell, Vol. 90, 549-558, Aug. 8, 1997). For experiments 30 μM MBP-Exonl-Q46 was incubated with 150 μg/mL thrombin in assay buffer (150 mM NaCl, 50 mM Tris pH 8.0) and 2 mM CaCl$_2$ for 16 hours at 37° C. Aggregated Exonl-Q46 was pelleted by centrifugation for 5 minutes at 13,000 rpm in a bench top centrifuge and re-dissolved in the same volume of assay buffer. Test compounds were prepared by titration in DMSO at 11 concentrations from 63 μM to 2 nM. For the RBA, Q46 protein aggregates and test compounds were pre-incubated in assay buffer for 20 minutes at room temperature, in 100 μL/well in a 96-well plate (pp, round bottom). Then, ligand was added in 50 μL/well and incubated for 60 minutes at 37° C. Final assay concentrations were 1 μM to 30 μM test compound, 1 μM Exonl-Q46 protein (equivalent monomer concentration) and 0.3 nM ligand [$^3$H$_3$-methyl]-5-((5-methoxypyridin-2-yl)methoxy)-2-(pyrazin-2-yl)benzo[d]oxazole. Samples were transferred onto GF/B filter plates and washed 2× with 200 μL PBS using a Filtermate Harvester. After drying filter plates for 1 hour at 55° C., the back of the plates were sealed with foil and 30 μL/well scintillation fluid (Packard MicroScint 40) added, incubated for 15 minutes in the dark and counted in a MicroBeta reader. For analysis, replicate data from independent assay plates were normalized towards 0% and 100% inhibition using control wells of vehicle (0% inhibition) and 1 μM unlabelled [$^3$H$_3$-methyl]-5-((5-methoxypyridin-2-yl)methoxy)-2-(pyrazin-2-yl)benzo[d]oxazole (100% inhibition). IC$_{50}$ values were determined with a sigmoidal inhibition model with four variables (top, bottom, slope, IC$_{50}$) in a global fit using the normalized replicate data.

The results for various example compounds were as provided in the table below:

| Example | Q46_RBA EC50_(uM) | Q46_RBA EC50_(uM) |
|---|---|---|
| 1 | 0.001237 | +++ |
| 1.1 | 0.007745 | +++ |
| 1.2 | 0.0489 | +++ |
| 1.3 | 0.04645 | +++ |
| 1.4 | 0.00848 | +++ |
| 1.5 | 0.005595 | +++ |
| 1.6 | 0.333 | ++ |
| 1.7 | 0.0965 | +++ |
| 1.8 | 0.001195 | +++ |
| 1.9 | 0.0278 | +++ |
| 1.10 | 0.005005 | +++ |
| 1.11 | 0.005203 | +++ |
| 1.12 | 0.0341 | +++ |
| 1.13 | 0.0875 | +++ |
| 1.14 | 0.0018 | +++ |
| 1.15 | 0.951 | + |
| 1.16 | 0.005732 | +++ |
| 1.17 | 0.00254 | +++ |
| 1.18 | 0.065 | +++ |
| 1.19 | 0.005445 | +++ |
| 1.20 | 0.00424 | +++ |
| 1.21 | 0.0163 | +++ |
| 1.22 | 0.002103 | +++ |
| 1.23 | 0.023 | +++ |
| 1.24 | 0.007865 | +++ |
| 1.25 | 0.002905 | +++ |
| 1.26 | 0.001785 | +++ |
| 1.27 | 0.05235 | +++ |
| 1.28 | 0.02935 | +++ |
| 1.29 | 0.271 | ++ |
| 1.30 | 1 | + |
| 2 | 0.09853 | +++ |
| 3 | 0.00126 | +++ |
| 4 | 0.07325 | +++ |
| 4.1 | 1 | + |
| 4.2 | 0.006915 | +++ |
| 4.3 | 0.003665 | +++ |
| 4.4 | 1 | + |
| 5 | 1 | + |
| 5.1 | 0.001646 | +++ |

| Example | Q46_RBA EC50_(uM) | Q46_RBA EC50_(uM) |
| --- | --- | --- |
| 6 | 0.002215 | +++ |
| 6.1 | 0.002645 | +++ |
| 6.2 | 0.00197 | +++ |
| 6.3 | 0.00786 | +++ |
| 7 | 0.1369 | ++ |
| 8 | 0.001792 | +++ |
| 8.1 | 0.001705 | +++ |
| 8.2 | 0.002025 | +++ |
| 9 | 0.0145 | +++ |
| 10 | 0.1859 | ++ |
| 11 | 0.001296 | +++ |
| 12 | 0.001725 | +++ |
| 13 | 1 | + |
| 15 | 0.05675 | +++ |
| 16 | 0.0395 | +++ |
| 17 | 0.333 | ++ |
| 18 | 0.3895 | ++ |
| 19 | 0.03745 | +++ |
| 20 | 1 | + |
| 24 | 0.002058 | +++ |
| 24.1 | 0.003007 | +++ |
| 24.2 | 0.01314 | +++ |
| 24.3 | 0.004445 | +++ |
| 24.4 | 0.043 | +++ |
| 25 | 0.153 | ++ |
| 26 | 0.0393 | +++ |
| 26.1 | 1 | + |
| 27 | 0.003188 | +++ |
| 27.1 | 0.01335 | +++ |
| 27.2 | 0.26 | ++ |
| 28 | 0.002185 | +++ |
| 29 | 0.161 | ++ |
| 29.1 | 0.086 | +++ |
| 30 | 0.704 | + |
| 31 | 0.108 | ++ |
| 32 | 0.191 | ++ |
| 33 | 0.03645 | +++ |
| 34 | 0.002485 | +++ |
| 34.1 | 0.005125 | +++ |
| 35 | 0.001046 | +++ |
| 35.1 | 0.008435 | +++ |
| 36 | 0.001955 | +++ |
| 37 | 0.0026 | +++ |
| 38 | 0.001247 | +++ |
| 39 | 0.01195 | +++ |
| 40 | 0.333 | ++ |
| 41 | 0.0235 | +++ |

Symbol: +++, <100 nM; ++, 100-500 nM, +, >500 nM

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention.

The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed:

1. A compound of Formula (I):

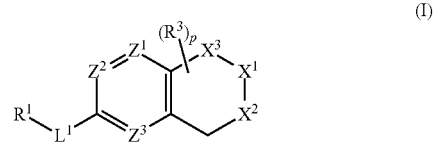

or an isotopically labeled analog, pharmaceutically acceptable salt, solvate, stereoisomer, or mixture of stereoisomers thereof, wherein:
$Z^1$ and $Z^2$ are each independently CH, or one of $Z^1$ and $Z^2$ is N and the other is CH;
$Z^3$ is N or CH;
$L^1$ is —O—$C_{1-4}$ alkylene;
one of $X^1$ and $X^2$ is N-$L^2$-$R^2$ and the other is $CH_2$;
$X^3$ is $CH_2$ or —O—$CH_2$—;
$L^2$ is —C(=O)—;
$R^1$ is heteroaryl optionally substituted with one or two substituents independently selected from hydroxy, alkyl, alkoxy, haloalkoxy, and —N($R^4$)$_2$;
$R^2$ is aryl, heteroaryl, heterocycloalkyl, or heterocycloalkenyl, each of which is substituted with one or two substituents independently selected from halogen, haloalkyl, hydroxy, alkyl, alkoxy, haloalkoxy, heteroaryl, and —N($R^4$)$_2$;
wherein when $R^2$ is substituted with alkyl, the alkyl is optionally substituted with alkenyl or alkoxy;
wherein when $R^2$ is substituted with alkoxy, the alkoxy is optionally substituted with alkenyl or alkoxy;
p is 0, 1, or 2;
each $R^3$ is independently $C_{1-4}$ alkyl; and
each $R^4$ is independently H or $C_{1-4}$alkyl.

2. The compound of claim 1, of Formula (IIa):

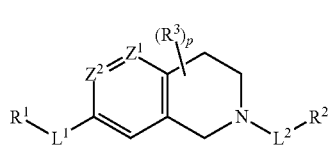

or an isotopically labeled analog, pharmaceutically acceptable salt, solvate, stereoisomer, or mixture of stereoisomers thereof.

3. The compound of claim 1, of Formula (IIb):

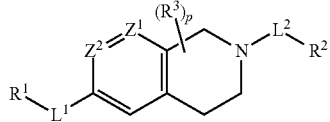

or an isotopically labeled analog, pharmaceutically acceptable salt, solvate, stereoisomer, or mixture of stereoisomers thereof.

4. The compound of claim 1, of Formula (IIIa):

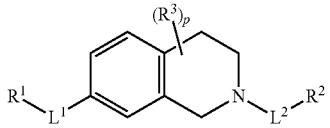

or an isotopically labeled analog, pharmaceutically acceptable salt, solvate, stereoisomer, or mixture of stereoisomers thereof.

5. The compound of claim 1, of Formula (IIIb):

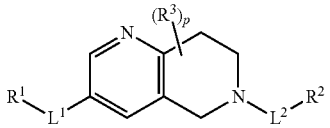

or an isotopically labeled analog, pharmaceutically acceptable salt, solvate, stereoisomer, or mixture of stereoisomers thereof.

6. The compound of claim 1, of Formula (IIIc):

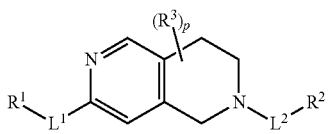

or an isotopically labeled analog, pharmaceutically acceptable salt, solvate, stereoisomer, or mixture of stereoisomers thereof.

7. The compound of claim 1, wherein $R^1$ is pyridinyl optionally substituted with one or two substituents independently selected from hydroxy, alkyl, alkoxy, and haloalkoxy.

8. The compound of claim 1, wherein $R^1$ is pyridinyl optionally substituted with methoxy.

9. The compound of claim 1, wherein $R^1$ is

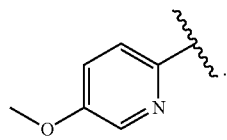

10. The compound of claim 1, wherein -$L^1$-$R^1$ is

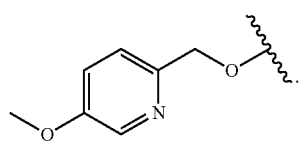 [SMILES: *OCc1ccc(OC)cn1]

11. The compound of claim 1, wherein $Z^1$ and $Z^2$ are each independently CH.

12. The compound of claim 1, wherein one of $Z^1$ and $Z^2$ is N and the other is CH.

13. The compound of claim 12, wherein $Z^1$ is N and $Z^2$ is CH.

14. The compound of claim 12, wherein $Z^2$ is N and $Z^1$ is CH.

15. The compound of claim 1, wherein $R^2$ is a substituted heteroaryl.

16. The compound of claim 1, wherein $R^2$ is a substituted 6-membered heteroaryl ring containing one or two N.

17. The compound of claim 1, wherein $R^2$ is selected from

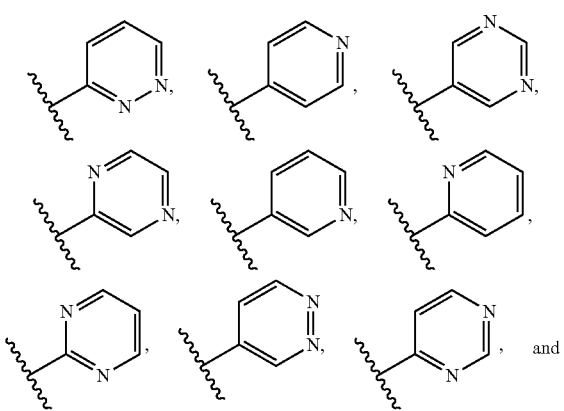

and each of which is substituted with one or two substituents independently selected from hydroxy, alkyl optionally substituted with alkoxy, haloalkyl, alkoxy optionally substituted with alkenyl or alkoxy, haloalkoxy, —N($R^4$)$_2$, and heteroaryl.

18. The compound of claim 1, wherein $R^2$ is a substituted heterocycloalkyl or heterocycloalkenyl.

19. The compound of claim 18, wherein R² is selected from

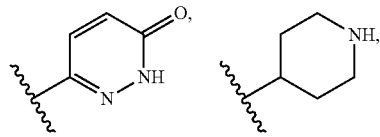

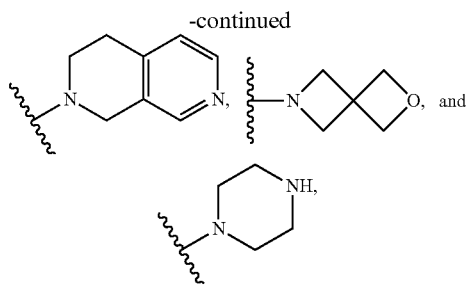

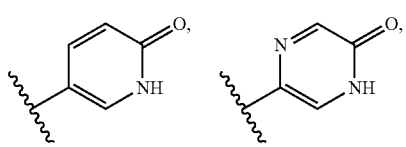

each of which is substituted with one or two substituents independently selected from hydroxy, alkyl optionally substituted with alkoxy, haloalkyl, alkoxy optionally substituted with alkenyl or alkoxy, haloalkoxy, —N(R⁴)₂, and heteroaryl.

20. The compound of claim 1, wherein $Z^3$ is CH.
21. The compound of claim 1, wherein $X^3$ is $CH_2$.
22. A compound selected from

| Example | Structure |
|---|---|
| 1 | 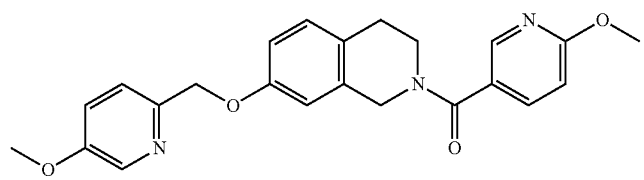 |
| 1.1 | 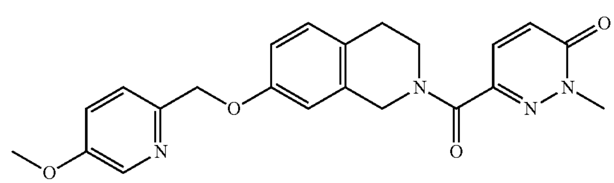 |
| 1.2 | 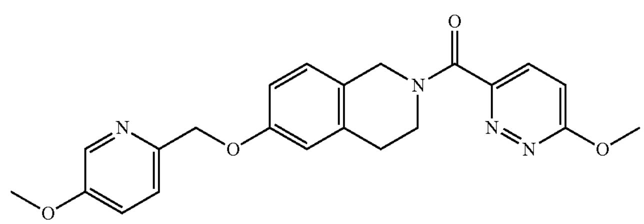 |
| 1.3 | 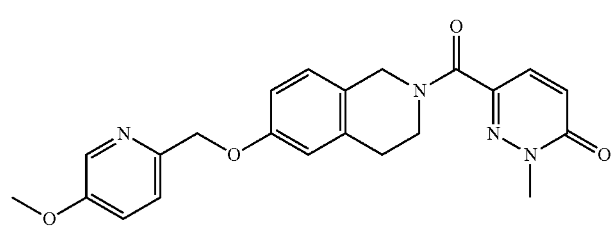 [SMILES: COc1ccc(COc2ccc3c(c2)CCN(C(=O)c2ccc(=O)n(C)n2)C3)nc1] |
| 1.4 | 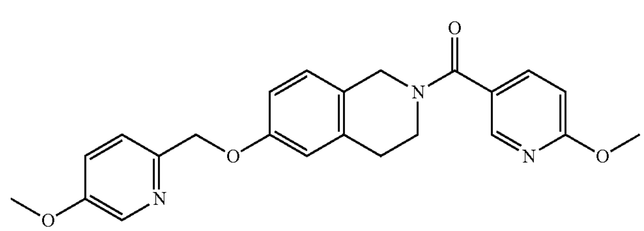 |

| Example | Structure |
|---|---|
| 1.5 | 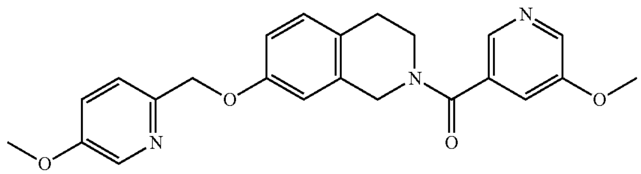 |
| 1.6 | 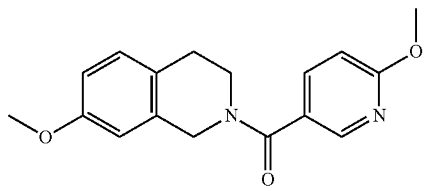 |
| 1.8 | 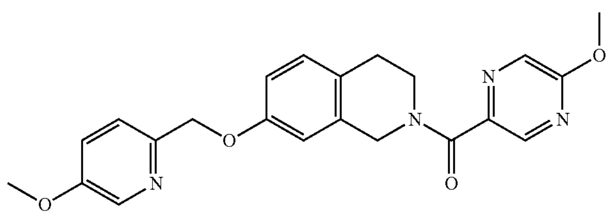 |
| 1.10 | 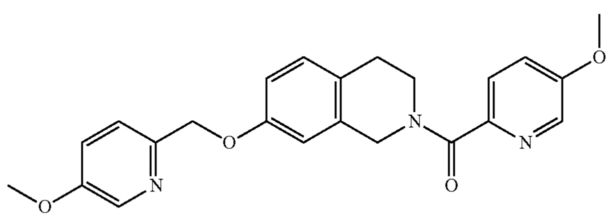 |
| 1.11 | 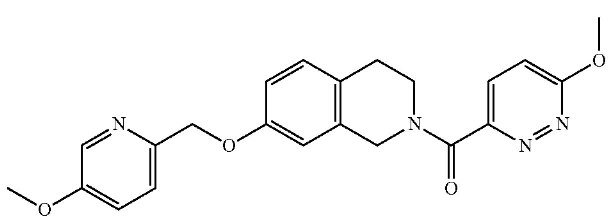 |
| 1.12 | 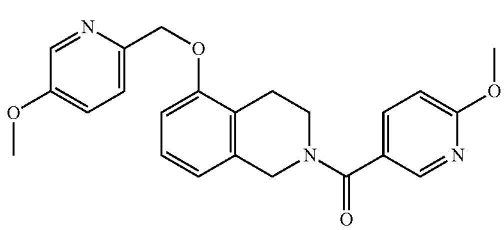 [SMILES: COc1ccc(COc2cccc3c2CCN(C(=O)c2ccc(OC)nc2)C3)nc1] |

-continued

| Example | Structure |
|---|---|
| 1.13 | 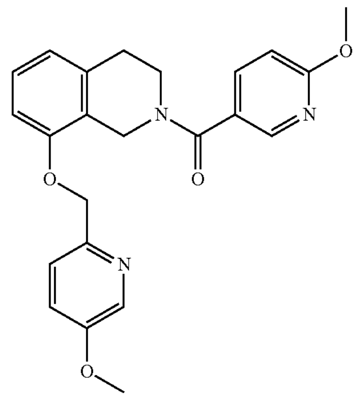 [SMILES: COc1ccc(COc2cccc3c2CN(C(=O)c2ccc(OC)nc2)CC3)nc1] |
| 1.14 | 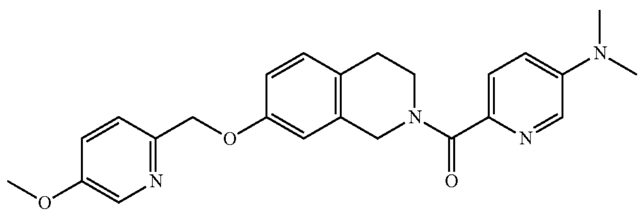 |
| 1.15 | 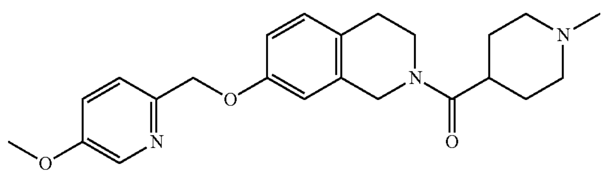 |
| 1.16 | 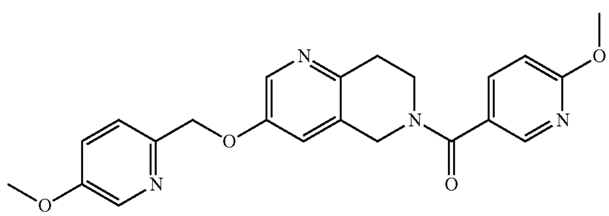 |
| 1.17 | 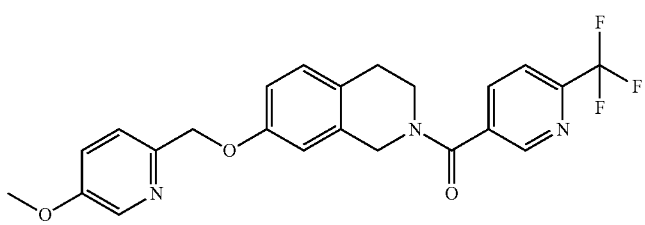 [SMILES: COc1ccc(COc2ccc3c(c2)CN(C(=O)c2ccc(C(F)(F)F)nc2)CC3)nc1] |
| 1.18 | 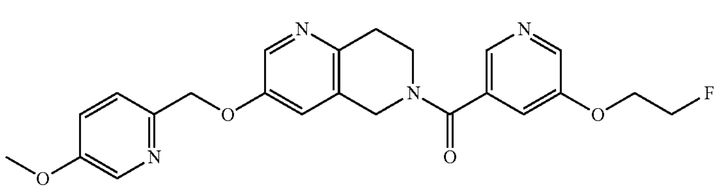 [SMILES: COc1ccc(COc2cnc3c(c2)CN(C(=O)c2cncc(OCCF)c2)CC3)nc1] |
| 1.19 | 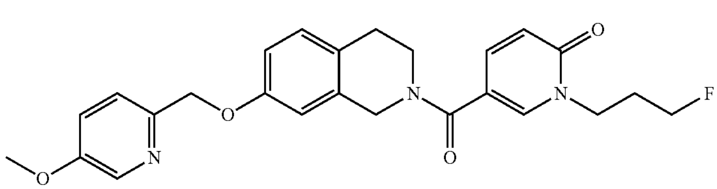 [SMILES: COc1ccc(COc2ccc3c(c2)CN(C(=O)c2ccc(=O)n(CCCF)c2)CC3)nc1] |

-continued
| Example | Structure |
|---|---|
| 1.20 | 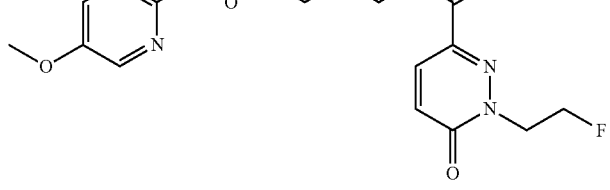 |
| 1.21 | 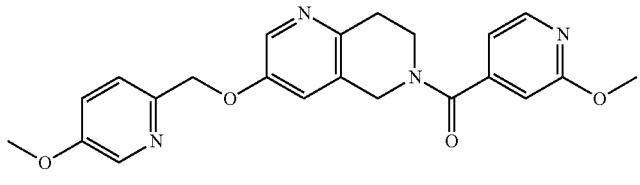 |
| 1.22 | 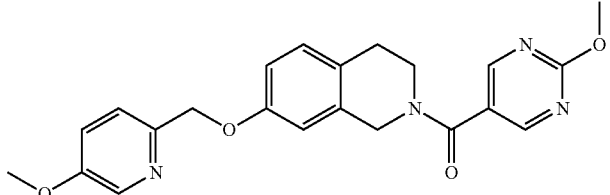 |
| 1.23 | 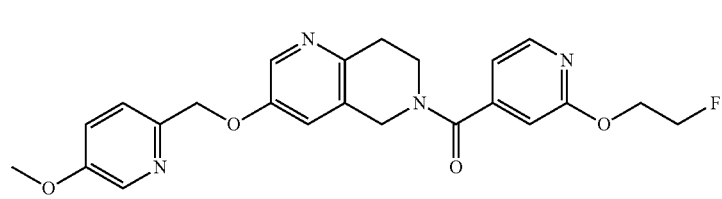 [SMILES: COc1ccc(COc2cnc3c(c2)CN(C(=O)c2ccnc(OCCF)c2)CC3)nc1] |
| 1.24 | 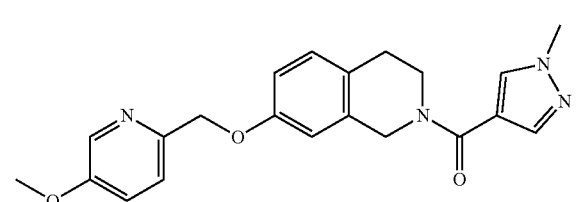 |
| 1.25 | 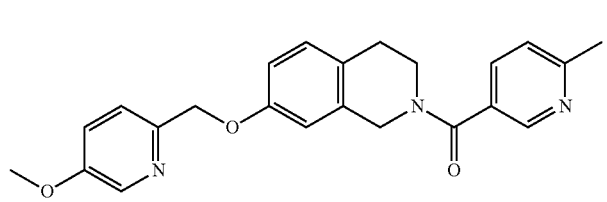 |
| 1.26 | 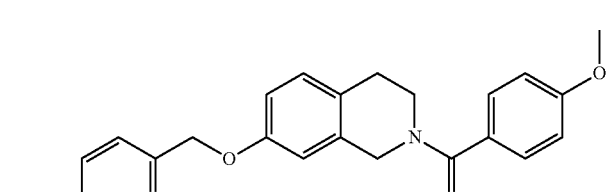 |

| Example | Structure |
|---|---|
| 1.27 | 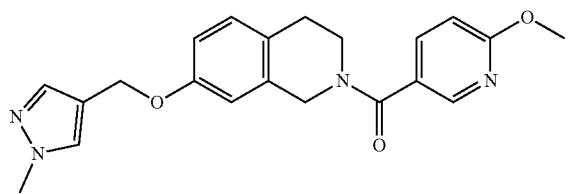 [SMILES: COc1ccc(C(=O)N2CCc3ccc(OCc4cnn(C)c4)cc3C2)cn1] |
| 1.28 | 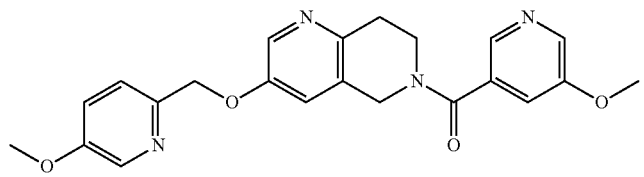 |
| 1.29 | 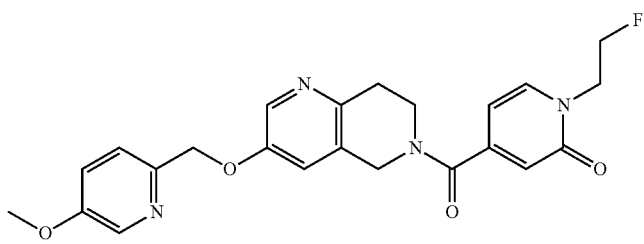 [SMILES: COc1ccc(COc2cnc3c(c2)CN(C(=O)c2ccn(CCF)c(=O)c2)CC3)nc1] |
| 4.3 | 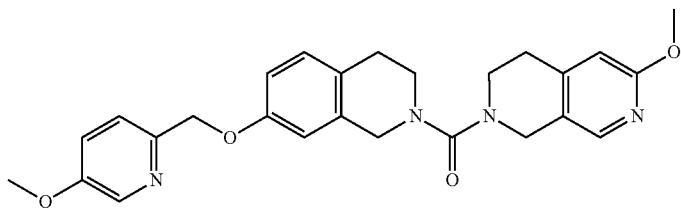 |
| 9 | 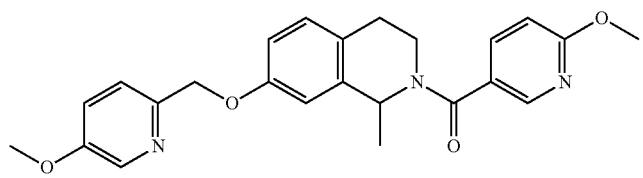 |
| 15 | 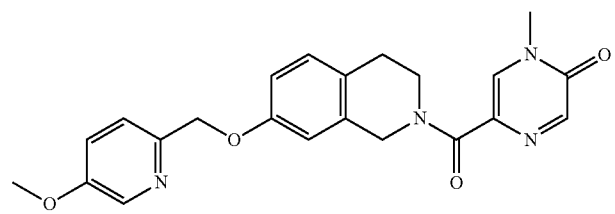 |
| 16 | 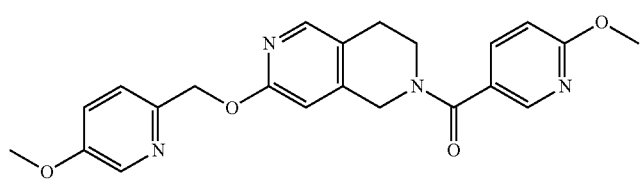 |

-continued
| Example | Structure |
|---|---|
| 20 | 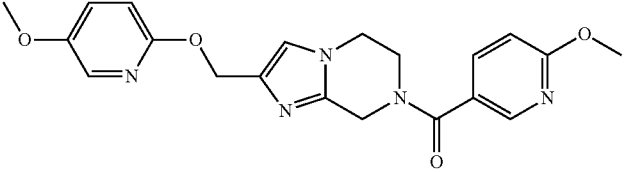 |
| 24 | 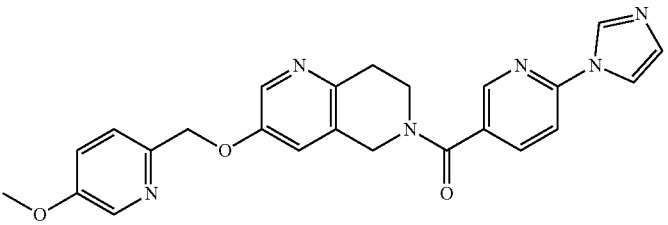 [SMILES: COc1ccc(COc2cnc3c(c2)CN(C(=O)c2ccc(-n4ccnc4)nc2)CC3)nc1] |
| 24.1 | 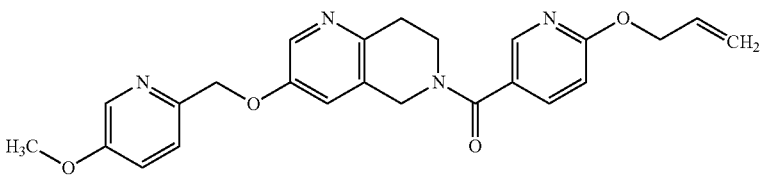 [SMILES: C=CCOc1ccc(C(=O)N2CCc3ncc(OCc4ccc(OC)cn4)cc3C2)cn1] |
| 24.2 | 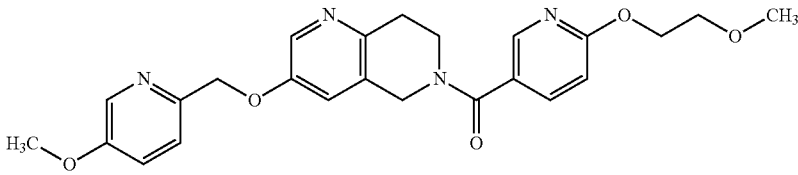 |
| 24.3 | 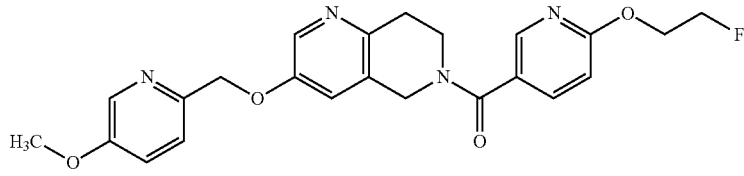 [SMILES: COc1ccc(COc2cnc3c(c2)CN(C(=O)c2ccc(OCCF)nc2)CC3)nc1] |
| 24.4 | 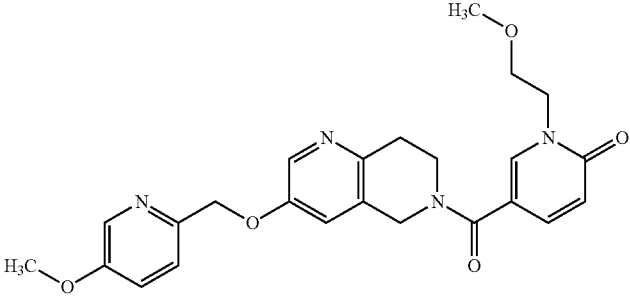 [SMILES: COCCn1cc(C(=O)N2CCc3ncc(OCc4ccc(OC)cn4)cc3C2)ccc1=O] |
| 25 | 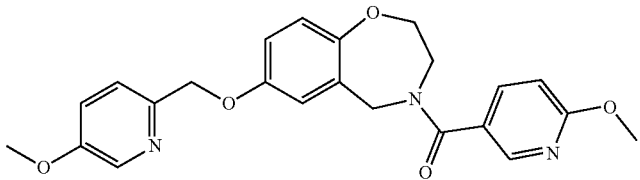 |

-continued

| Example | Structure |
|---|---|
| 26 | 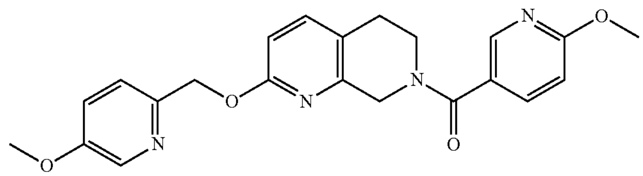 |
| 28 | 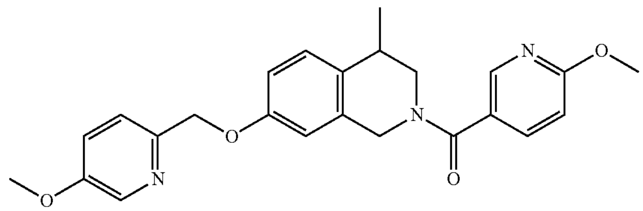 |
| 31 | 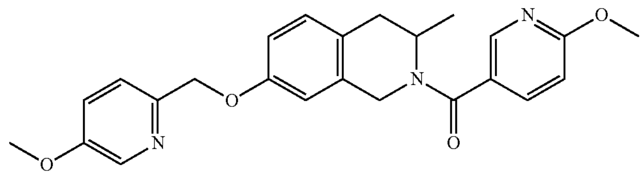 |
| 34 | 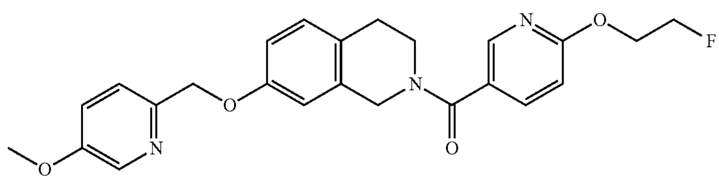 [SMILES: COc1ccc(COc2ccc3c(c2)CN(C(=O)c2ccc(OCCF)nc2)CC3)nc1] |
| 34.1 | 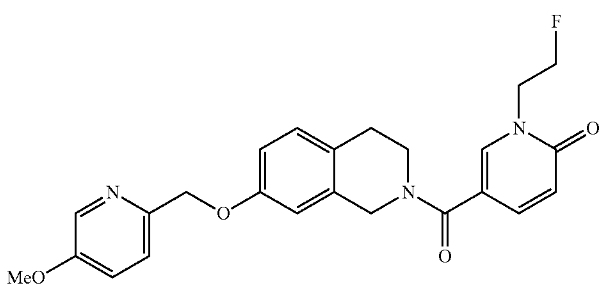 [SMILES: COc1ccc(COc2ccc3c(c2)CN(C(=O)c2ccc(=O)n(CCF)c2)CC3)nc1] |
| 35 | 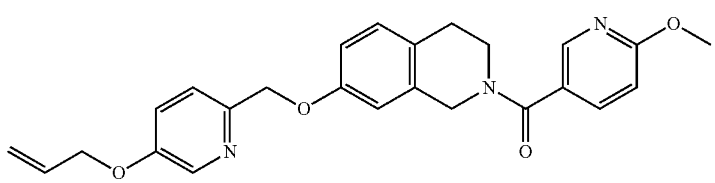 [SMILES: C=CCOc1ccc(COc2ccc3c(c2)CN(C(=O)c2ccc(OC)nc2)CC3)nc1] |
| 35.1 | 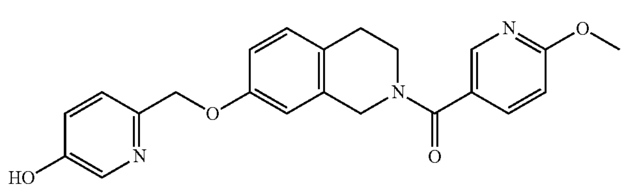 [SMILES: COc1ccc(C(=O)N2CCc3ccc(OCc4ccc(O)cn4)cc3C2)cn1] |
| 36 | 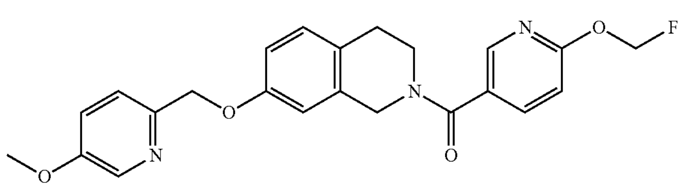 [SMILES: COc1ccc(COc2ccc3c(c2)CN(C(=O)c2ccc(OCF)nc2)CC3)nc1] |

| Example | Structure |
|---------|-----------|
| 37 | *(structure)* |
| 38 | *(structure)* |
| 40 | *(structure)* and |
| 41 | *(structure)* | or an isotopically labeled analog, pharmaceutically acceptable salt, solvate, stereoisomer, or mixture of stereoisomers thereof.

23. The compound of claim 1, wherein the compound is labeled with one or more positron-emitting radionuclides.

24. The compound of claim 23, wherein the compound contains one or more positron-emitting radionuclides selected from $^{11}$C, $^{13}$N, $^{15}$O, and $^{18}$F.

25. An imaging agent comprising the compound of claim 23, or an isotopically labeled analog, pharmaceutically acceptable salt, solvate, stereoisomer, or mixture of stereoisomers thereof.

26. A method of generating diagnostic images in an individual comprising administering an effective amount of an imaging agent of claim 25 to an individual, and generating an image of a body part or body area of the individual.

27. The method of claim 26, wherein generating an image of a body part or body area of the individual comprises generating an image to detect the presence or absence of huntingtin protein (HTT protein) in the image; and detecting the presence or absence of a pathologic process.

28. The method of claim 27, wherein the HTT protein is found in basal ganglia.

29. The method of claim 27, wherein the pathologic process is a neurodegenerative disease.

30. The method of claim 29, wherein the neurodegenerative disease is selected from Alzheimer's disease, amyotrophic lateral sclerosis, Huntington's disease, Parkinson's disease, Prion disease and spinocerebellar ataxias.

31. The method of claim 30, wherein the neurodegenerative disease is Huntington's disease (HD).

32. The method of claim 26, wherein the effective amount of the imaging agent comprises from about 0.1 to about 20 mCi.

33. The method of claim 32, wherein the effective amount of the imaging agent comprises about 10 mCi.

34. The method of claim 26, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof.

35. The method of claim 34, wherein generating an image comprises PET imaging.

36. The method of claim 27, wherein the HTT protein is present as aggregates thereof.

37. The method of claim 27, wherein the HTT protein is mutant.

38. The method of claim 27, wherein the body part or body area is selected from head, spinal cord, limb, thorax, or abdomen.

39. The method of claim 27, wherein the body part or body area is brain.

* * * * *